(12) United States Patent
Ingram et al.

(10) Patent No.: US 7,026,152 B2
(45) Date of Patent: Apr. 11, 2006

(54) METHODS AND COMPOSITIONS FOR SIMULTANEOUS SACCHARIFICATION AND FERMENTATION

(75) Inventors: Lonnie O'Neal Ingram, Gainesville, FL (US); Shengde Zhou, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 228 days.

(21) Appl. No.: 09/885,297

(22) Filed: Jun. 19, 2001

(65) Prior Publication Data

US 2002/0159990 A1 Oct. 31, 2002

Related U.S. Application Data

(60) Provisional application No. 60/219,913, filed on Jul. 21, 2000, and provisional application No. 60/214,137, filed on Jun. 26, 2000.

(51) Int. Cl.
*C12P 21/06* (2006.01)
*C12N 9/00* (2006.01)
*C12N 9/24* (2006.01)
*C12N 9/44* (2006.01)
*C07H 21/04* (2006.01)

(52) U.S. Cl. .............. 435/210; 435/4; 435/6; 435/69.1; 435/183; 435/200; 435/252.3; 435/252.33; 435/320; 435/325; 536/23.2; 536/23.4; 536/23.74; 530/350

(58) Field of Classification Search .......... 435/41, 435/69.1, 161, 162–165, 440, 471, 183, 200, 435/209, 243, 252.3, 252.33, 320.1, 262, 435/274, 4, 6, 210; 536/23.2, 23.4, 23.7, 536/23.74; 530/350

See application file for complete search history.

(56) References Cited

U.S. PATENT DOCUMENTS

| 3,990,944 | A | 11/1976 | Gauss et al. | 195/33 |
|---|---|---|---|---|
| 5,000,000 | A | 3/1991 | Ingram et al. | 435/161 |
| 5,028,539 | A | 7/1991 | Ingram et al. | 435/161 |
| 5,162,516 | A | 11/1992 | Ingram et al. | 536/27 |
| 5,424,202 | A | 6/1995 | Ingram et al. | 435/161 |
| 5,482,846 | A | 1/1996 | Ingram et al. | 435/161 |
| 5,487,989 | A | 1/1996 | Fowler et al. | 435/165 |
| 5,554,520 | A | 9/1996 | Fowler et al. | 435/165 |
| 5,821,093 | A | 10/1998 | Ingram et al. | 435/161 |

FOREIGN PATENT DOCUMENTS

| WO | WO 98/45425 A1 | 10/1998 |
|---|---|---|
| WO | WO 00/71729 A3 | 11/2000 |
| WO | WO 00/71729 A2 | 11/2000 |

OTHER PUBLICATIONS

Riedel et al. FEMS Microbiology Lett., 1997, vol. 147:239–243.*
Zhou et al. J. Industrial Microbiol. Biotechnol., 1999, vol. 22:600–607.*
Liebl et al. Microbiology, 1996, vol. 142(9) :2533–2542.*
Riedel et al. (Mol. Microbiol., 1998, vol. 28(4):767–775).*
Asghari et al. (1996) Ethanol production from hemicellulose hydrolysates of agricultural residues using genetically engineered *Escherichia coli* strain KO11. *J. Ind. Microbiol.* 16:42–47.
Barbosa et al. (1992) Expression of the *Zymomonas mobilis* alcohol dehydrogenase II (adhB) and pyruvate decarboxylase (pdc) genes in Bacillus. *Current Microbiol.* 28:279–282.
Barras et al. (1994) Extracellular enzymes and pathogenesis of soft–rot Erwinia. *Annu. Rev. Phytopathol.* 32:201–234.
Beall et al. (1991) Parametric studies of ethanol production from xylose and other sugars by recombinant *Escherichia coli*. *Biotechnol. Bioeng.* 38:296–303.
Beall et al. (1992) Conversion of hydrolysates of corn cobs and hulls into ethanol by recombinant *Escherichia coli* B containing integrated genes for ethanol production. *Biotechnol. Lett.* 14:857–862.
Beall, et al. (1993) Genetic engineering of soft–rot bacteria for ethanol production from lignocellulose. *J. Indust. Microbiol.* 11:151–155.
Boyer, M.–H. et al. (1987) Isolation of the gene encoding the major endoglucanase of erwinia chrysanthemi homology between cel genes of two strains of erwinia–chrysanthemi. *FEMS Microbiol. Lett.* 41(3):351–6.
Boyer, M.–H. et al. (1987) Characterization of a new endoglucanase from *Erwinia chrysanthemi*. *Eur. J. Biochem.* 162(2):311–6.
Brooks et al. (1995) Conversion of mixed waste office paper to ehtanol by genetically engineered *Klebsiella oxytoca* strain P2. *Biotechnol. Progress.* 11:619–625.
Burchhardt et al. (1992) Conversion of xylan to ethanol by ethanologenic strains of *Escherichia coli* and *Klebsiella oxytoca*. *Appl. Environ. Microbiol.* 58:1128–1133.
Cho, K.M. et al. (1999) Novel SSF process for ethanol production from microcrystalline cellulose using the ō–integrated recombinant yeast, *Saccharomyces cerevisiae* L2612ōGC. *J. Microbiol. Biotechnol.* 9:340–345.

(Continued)

*Primary Examiner*—Manjunath N. Rao
(74) *Attorney, Agent, or Firm*—Edwards & Angell, LLP; Peter C. Lauro, Esq.

(57) ABSTRACT

The invention provides compositions and methods for the synergistic degradation of oligosaccharides by endoglucanases. The invention further provides recombinant host cells containing one or more genes encoding endoglucanses which are capable of the synergistic degradation of oligosaccharides. Preferred host cells of the invention are ethanologenic and capable of carrying out simultaneous saccharification and fermentation resulting in the production of ethanol from complex cellulose substrates.

16 Claims, 18 Drawing Sheets

OTHER PUBLICATIONS

Conway, T. et al. (1987) Cloning and sequencing of the alcohol dehydrogenase II gene from *Zymomonas mobilis*. *J. Bacteriol*. 169(6):2591–7.

Conway et al. (1987) Gene expression in *Zymomonas mobilis*: promoter structure and identification of membrane anchor sequences forming functional lacZ' fusion proteins. *J. Bacteriol*. 169:2327–2336.

Doran et al. (1993) Fermentation of crystalline cellulose to ethanol by *Klebsiella oxytoca* containing chromosomally integrated *Zymomonas mobilis* genes. *Biotechnol. Progress*. 9:533–538.

Doran et al. (1994) Saccharification and fermentation of sugar cane bagasse by *Klebsiella oxytoca* P2 containing chromosomally integrated genes encoding the *Zymomonas mobilis* ethanol pathway. *Biotechnol. Bioeng*. 44:240–247.

Fierobe, H.-P. et al. (1993) Purification and characterization of endoglucanase C from *Clostridium cellulolyticum*. Catalytic comparison with endoglucanase A. *Eur. J. Biochem*. 217(2):557–65.

Figurski et al. (1979) Replication of an origin–containing derivative of plasmid RK2 dependent on a plasmid function provided in trans. *Proc. Natl. Acad. Sci. USA*. 76:1648–1652.

Grohmann et al. (1994) Fermentation of galacturonic acid and other sugars in orange peel hydrolysates by the ethanologenic strain of *Escherichia coli*. *Biotechnol. Lett*. 16:281–286.

Guimaraes et al. (1992) Ethanol production from starch by recombinant *Escherichia coli* containing integrated genes for ethanol production and plasmid genes for saccharification. *Biotechnol. Lett*. 14:415–420.

Guimaraes et al. (1992) Fermentation of sweet whey by ethanologenic *Escherichia coli*. *Biotechnol. Bioeng*. 40:41–45.

Guiseppi, A. et al. (1991) Sequence analysis of the cellulase–encoding celY gene of *Erwinia chrysanthemi*: a possible case of interspecies gene transfer. *Gene*. 106(1):109–14.

Hahn–Hägerdal et al. (1994) An interlaboratory comparison of the performance of ethanol–producing micro–organisms in a xylose–rich acid hydrolysate. *Appl. Microbiol. Biotechnol*. 41:62–72.

He et al. (1991) Cloned *Erwinia chrysanthemi* out genes enable *Escherichia coli* to selectively secrete a diverse family of heterologous proteins to its milieu. *Proc. Natl. Acad. Sci. U.S.A*. 88(3):1079–83.

Hueck et al. (1998) Type III protein secretion systems in bacterial pathogens of animals and plants. *Microbiol. Mol. Biol. Rev*. 62(2):379–433.

Ingram et al. (1987) Genetic engineering of ethanol production in *Escherichia coli*. *Appl. Environ. Microbiol*. 53(10):2420–5.

Ingram et al. (1988) Expression of different levels of ethanologenic enzymes from zymomonas mobilis in recombinant strains of *Escherichia coli*. *Appl. Environ. Microbiol*. 54:397–404.

Ingram, et al. (1999) Enteric bacterial catalysts for fuel ethanol production. *Biotechnol. Prog*. 15:855–866.

Kuhnert, P. et al. (1997) Detection system for *Escherichia coli*–specific virulence genes: absence of virulence determinants in B and C strains. *Appl. Environ. Microbiol*. 63(2):703–9.

Lai et al. (1996)Cloning of cellobiose phosphoenolpyrivate–dependent phosphotransferase genes: Functional expression in recombinant *Escherichia coli* and identification of a putative binding region for disaccharides. *Appl. Environ. Microbiol*. 63:355–363.

Lindeberg et al. (1992) Analysis of eight out genes in a cluster required for pectic enzyme secretion by *Erwinia chrysanthemi*: sequence comparison with secretion genes from other gram–negative bacteria. *J. Bacteriol*. 174(22):7385–97.

Lindeberg et al. (1996) Complementation of deletion mutations in a cloned functional cluster of *Erwinia chrysanthemi* out genes with *Erwinia carotovora* out homologues reveals OutC and OutD as candidate gatekeepers of species–specific secretion of proteins via the type II pathway. *Mol. Microbiol*. 20(1):175–90.

Lynd et al. (1991) Fuel ethanol from cellulosic biomass. *Science* 251:1318–1323.

Martinez–Morales, F. et al. (1999) Chromosomal integration of heterologous DNA in *Escherichia coli* with precise removal of markers and replicons used during construction. *J. Bacteriol*. 181(22):7143–8.

Moniruzzaman et al. (1996) Ethanol production from afex pretreated corn fiber by recombinant bacteria. *Biotechnol. Lett*. 18:985–990.

Moniruzzaman, M. et al. (1997) Extracellular melibiose and fructose are intermediates in raffinose catabolism during fermentation to ethanol by engineered enteric bacteria. *J. Bacteriol*. 179(6):1880–6.

Moniruzzaman et al. (1998) Ethanol production from dilute acid hydrolysate of rice hulls using genetically engineered *Escherichia coli*. *Biotechnol. Lett*. 20:943–947.

Murata et al. (1990) Characterization of transposon insertion out– mutants of *Erwinia carotovora* subsp. *carotovora* defective in enzyme export and of a DNA segment that complements out mutations in *E. carotovora* subsp. *carotovora*, *E. carotovora* subsp. *atroseptica*, and *Erwinia chrysanthemi*. *J. Bacteriol*. 172:2970–2978.

Ohta, K. et al. (1991) Genetic improvement of *Escherichia coli* for ethanol production: chromosomal integration of *Zymomonas mobilis* genes encoding pyruvate decarboxylase and alcohol dehydrogenase II. *Appl. Environ. Microbiol*. 57(4):893–900.

Okamoto et al. (1994) Cloning of the *Acetobacter xylinum* cellulase gene and its expression in *Escherichia coli* and *Zymomonas mobilis*. *Appl. Microbiol. Biotechnol*. 42(4):563–8.

Osman, et al. (1985) Mechanism of ethanol inhibition of fermentation in *Zymomonas mobilis* CP4. *J. Bact*. 164:173–180.

Nidetzky, et al. (1995) *Synergistic interaction of cellulases from Trichoderma reesei during cellulose degradation* p. 90–112.

Pósfai, G. et al. (1997) Versatile insertion plasmids for targeted genome manipulations in bacteria: isolation, deletion, and rescue of the pathogenicity island LEE of the *Escherichia coli* O157:H7 genome. *J. Bacteriol*. 179(13):4426–8.

Poulsen, O.M. et al. (1992) Degradation of microcrystalline cellulose synergism between different endoglucanases of cellulomonas–sp atcc 21399. *Biotech. Bioeng*. 39(1):121–23.

Pugsley et al. (1993) The complete general secretory pathway in gram–negative bacteria. *Microbiol. Rev.* 57(1):50–108.

Riedel, K. et al. (1997) Synergistic interaction of the *Clostridium stercorarium* cellulases avicelase I (CelZ) and avicelase II (CelY) in the degradation of microcrystalline cellulose. *FEMS Microbiol. Lett.* 147:239–243.

Saito et al. (1990) Expression of a thermostable cellulase gene from a thermophilic anaerobe in *Saccharomyces cerevisiae. J. Ferment. Bioeng.* 69:282–286.

Sheehan, J., (1994) Bioconversion for production of renewable transportation fuels in the United States. *Amer. Chem. Soc.* pp 1–52.

Su et al. (1993) Simultaneous expression of genes encoding endoglucanase and β–glucosidase in *Zymomonas mobilis. Biotechnol. Lett.* 15:979–984.

Tomme, et al. (1995) Cellulose hydrolysis by bacteria and fungi. *Adv. Microb. Physiol.* 37:1–81.

Wood et al. (1988) Methods for measuring cellulase activities. *Methods in Enzymology* 160:87–112.

Wood, et al. (1992) Ethanol production from cellobiose, amorphous cellulose, and crystalline cellulose by recombinant *Klebsiella oxytoca* containing chromosomally integrated *Zymomonas mobilis* genes for ethanol production and plasmids expressing thermostable cellulase genes from *Clostridium thermocellum. Appl. Environ. Microbiol.* 58(7):2103–10.

Wood et al. (1997) Production of recombinant bacterial endoglucanase as a co–product with ethanol during fermentation using derivatives of *Escherichia coli* KO11. *Biotech. Bioeng.* 55:547–555.

Woodward, J. (1991) Synergism in cellulase systems. *Bioresource Technol.* 36:67–75.

Wyman, C.E. et al. (1995) Economic fundamentals of ethanol production from lignocellulosic biomass. *Amer. Chem. Soc. Symp.* 618:272–290.

Yomano et al. (1998) Isolation and characterization of ethanol–tolerant mutants of *Escherichia coli* KO11 for fuel ethanol production. *J. Ind. Microbiol. Biotechnol.* 20(2):132–8.

Zhou, S. et al. (1999) Enhancement of expression and apparent secretion of *Erwinia chrysanthemi* endoglucanae (encoded by celZ) in *Escherichia coli* B. B. *Appl. Environ. Microbiol.* 65:2439–2445.

Zhou, S. et al. (1999) Engineering endoglucanase–secreting strains of ethanologenic *Klebsiella oxytoca* P2. *J. Indust. Microbiol. Biotechnol.* 22:600–607.

Zhou, S. et al. (2000) Synergistic hydrolysis of carboxymethyl cellulose and acid–swollen cellulose by two endoglucanases (CelZ and CelY) from *Erwinia chrysanthemi. J. Bacteriol.* 182:5676–5682.

Zhou, S. et al. (2001) Gene integration and expression and extracellular secretion of *Erwinia chrysanthemi* endoglucanase CelY (celY) and CelZ (celZ) in ethanologenic *Klebsiella oxytoca* P2. *Appl. Environ. Microbiol.* 67: 6–14.

* cited by examiner

Fig. 5

```
          -35 region                            -10 region           #
1051 CTTTTTCGGC  ATGAGCAACC  AACATTTTCA  AGGTATCATC  CTGATGCGCA 1101 ATATCGGCAT  CGGTTAGCCA  TAACCATTTT  ACCTGTCCGG  CGGCCTTAAT
1151 ACCTTGATCA  GATGGTTCGT  GGTGTTGTTA  CCTTGCCGAA  GGGCACCGGT
1201 AAAAATGTTC  GCGTCGGTGT  TTTCGCCCGT  GGCCCGAAAG  CTGAAGAAGC
1251 TAAAGCTGCT  GGTGCAGAAG  TTGTCGGCGC  AGAAGACCTG  ATGGAAGCCA -35 region                         -10 region
1301 TTCAGGGCGG  CAGCATTGAT  TTCGATCGTG  ATGCCCTTTA  TACTGAAATT

1351 GCCTTGCGCT  GCCATAATGA  AGCAGCCTCC  GGTGTTTTGG  CAGATTTAAG

Shine-Dalgarno
1401 CGCTGCCTGA  TTTTCGTgat  cctctagagt  ctatgaaatg  gagattcatt celZ coding region→
1451 tatgcctctc  tcttattcgg  ataaccatcc  agtcatccgc  aagcttggcc (SEQ ID NO: 1)
``` pLOI2306 (11520 bps)

Fig. 14

| Position (bp) | -35 | -10 | RNA Start | Proposed δ factors | δ factor consensus sequence | |
|---|---|---|---|---|---|---|
| | | | | | -35 | -10 |
| ATATTTTGATTTTCAAGAAAAGCCTGATATCTTCCAACATCTT (SEQ ID NO: 18) | | | T (2) | $\delta^{70}$ | TTGACA | TATAAT |
| GATTGATCCTCTAGAGTCAACCTGCTTGTTACTCGTGATCCCAT (SEQ ID NO: 19) | | | A (4) | $\delta^{70}$ | TTGACA | TATAAT |
| GAGTCAACCTGCTTGTTACTCGTGATCCCATTCACAAGGGCGAA (SEQ ID NO: 20) | | | C (1) | $\delta^{32}$ | CTTGAAA | CCCCAT |
| TTACTCGTGATCCCATTCACAAGGGCGAATTAATTCGCCCTT (SEQ ID NO: 21) | | | C (3) | $\delta^{38}$ | CCGCCT | TATACT |

SEQUENCE LISTING

<160> NUMBER OF SEQ ID NOS: 24

<210> SEQ ID NO 1
<211> LENGTH: 450
<212> TYPE: DNA
<213> ORGANISM: Artificial Sequence
<220> FEATURE:
<223> OTHER INFORMATION: Description of Artificial Sequence: Synthetic
      promoter sequence

<400> SEQUENCE: 1

```
cttttcggc atgagcaacc aacatttca aggtatcatc ctgatgcgca atatcggcat      60
cggttagcca taaccatttt acctgtccgg cggccttaat accttgatca gatggttcgt     120
ggtgttgtta ccttgccgaa gggcaccggt aaaaatgttc gcgtcggtgt tttcgcccgt    180
ggcccgaaag ctgaagaagc taaagctgct ggtgcagaag ttgtcggcgc agaagacctg    240
atggaagcca ttcagggcgg cagcattgat ttcgatcgtg atgccctta tactgaaatt     300 gccttgcgct gccataatga agcagcctcc ggtgttttgg cagatttaag cgctgcctga    360
ttttcgtgat cctctagagt ctatgaaatg gagattcatt tatgcctctc tcttattcgg    420
ataaccatcc agtcatccgc aagcttggcc                                     450
```

<210> SEQ ID NO 2
<211> LENGTH: 1509
<212> TYPE: DNA
<213> ORGANISM: Artificial Sequence
<220> FEATURE:
<223> OTHER INFORMATION: Description of Artificial Sequence: Synthetic expression vector

<400> SEQUENCE: 2

| | |
|---|---:|
| gatcaaccgg caatttatcc acggcatcaa attcgatctg tcttttcccg tatcattggc | 60 |
| aataccggca ttctgattac aggccgtgtt ttgaatgcgg tatgcagttt tgtctatgtc | 120 |
| gcatggacat cccagacatt gggattgaac ctgtttggtg tcatgctttt gattacgact | 180 |
| tttgctaccc tgatttcgga tattacccgt tttcagtcat ggcaaacctt gctgcattac | 240 |
| ggttcaaaag cttttcagga aaaagatttt aaccaatttg atgatgtcct tgccttttgc | 300 |
| atcagagccg atttttttag tgcggcgata gtatgttgg tagggttagg cggtatcttg | 360 |
| attttaggca cttcaagatt gggatggcct gccgaggtca agccagatgc cttgctttgt | 420 |
| atgctgatta tacttttat gaatatcggc tggtccaacc gggatgttgc ggctgtgtaa | 480 |
| ccgctttaaa ctggtcacta tttatgagtt tattacgacc tgcgtcagaa ccggaggttg | 540 |
| tggcattggt tattggcttc atatgccttt ggggtatttt ttgtttatat ggtgcctgac | 600 |
| gcaattcacg cttttttgtca cctgtagtta cgctggcatt tatctctttc accaatatac | 660 |
| ggagcgagca tttccgataa gaaaatatt tcagagaaaa acgcccgttg aagggatgtg | 720 |
| gaaattcact ttaagcgtca gttttaatga atcctagac tccatttttcc agcagggtgg | 780 |
| caccccttgct attggtagct cactgggggc tggggaagcc gctgtctatc gggtcgcgcg | 840 |
| ccagattagt aacggtttat ccaaaccagc acagatgatg atcggctaac atgcatccac | 900 |
| cggcagcacc ggccgttta tgcttgggat tattgatatg ccgaaaagga tacaacatct | 960 |
| ggaagaaaaa gacgaaggcc ggaataagcg cccattctgc aaaattgtta caacttagtc | 1020 |
| gcgccatcag ggaatgaaaa atcaatccgt cttttcggc atgagcaacc acatttttca | 1080 |
| aggtatcatc ctgatgcgca atatcggcat cggttagcca taaccattt acctgtccgg | 1140 |
| cggccttaat accttgatca gatggttcgt ggtgttgtta ccttgccgaa gggcaccggt | 1200 |
| aaaaatgttc gcgtcggtgt tttcgcccgt ggcccgaaag ctgaagaagc taaagctgct | 1260 |
| ggtgcagaag ttgtcggcgc agaagacctg atggaagcca ttcagggcgg cagcattgat | 1320 |
| ttcgatcgtg atgccctta tactgaaatt gccttgcgct gccataatga agcagcctcc | 1380 |
| ggtgttttgg cagatttaag cgctgcctga ttttcgtgat cctctagagt ctatgaaatg | 1440 |
| gagattcatt tatgcctctc tcttattcgg ataaccatcc agtcatccgc aagcttggcc | 1500 |
| gtaatccat | 1509 |

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 3

| | |
|---|---:|
| cgaattcctg ccgaagttta ttagcca | 27 |

<210> SEQ ID NO 4

```
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaggatcctt ccaccagcta tttgttagtg a                                      31

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agaattctgc cagttggttg acgatag                                           27

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caggatcccc tcaagtcact agttaaactg                                        30

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
taatacgact cactataggg                                                   20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cacgacgttg taaaacgac                                                    19

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
taacaatttc acacagga                                                     18

<210> SEQ ID NO 10
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gactggatgg ttatccgaat aagagagagg                                      30

<210> SEQ ID NO 11
<211> LENGTH: 8
<212> TYPE: DNA
<213> ORGANISM: Artificial Sequence
<220> FEATURE:
<223> OTHER INFORMATION: Description of Artificial Sequence: Synthetic
      nucleotide linker

<400> SEQUENCE: 11 ggcgcgcc                                                               8

<210> SEQ ID NO 12
<211> LENGTH: 11544
<212> TYPE: DNA
<213> ORGANISM: Artificial Sequence
<220> FEATURE:
<223> OTHER INFORMATION: Description of Artificial Sequence: Synthetic
      nucleotide vector sequence
<220> FEATURE:
<221> NAME/KEY: CDS
<222> LOCATION: (1452)..(2735)
<220> FEATURE:
<221> NAME/KEY: modified_base
<222> LOCATION: (3282)..(4281)
<223> OTHER INFORMATION: a, c, g, t, unknown, or other
<220> FEATURE:
<221> NAME/KEY: CDS
<222> LOCATION: (4916)..(5776)
<220> FEATURE:
<221> NAME/KEY: CDS
<222> LOCATION: (7061)..(8251)
<220> FEATURE:
<221> NAME/KEY: modified_base
<222> LOCATION: (9476)..(11544)
<223> OTHER INFORMATION: a, c, g, t, unknown, or other

<400> SEQUENCE: 12
gatcaaccgg caatttatcc acggcatcaa attcgatctg tcttttcccg tatcattggc     60
aataccggca ttctgattac aggccgtgtt ttgaatgcgg tatgcagttt tgtctatgtc    120
gcatggacat cccagacatt gggattgaac ctgtttggtg tcatgctttt gattacgact    180
tttgctaccc tgatttcgga tattaccgt  tttcagtcat ggcaaacctt gctgcattac    240
ggttcaaaag cttttcagga aaagatttt  aaccaatttg atgatgtcct tgccttttgc    300
atcagagccg atttttttag tgcggcgata ggtatgttgg tagggttagg cggtatcttg    360
attttaggca cttcaagatt gggatggcct gccgaggtca agccagatgc cttgctttgt    420
atgctgatta ctttttttat gaatatcggc tggtccaacc gggatgttgc ggctgtgtaa    480
ccgctttaaa ctggtcacta tttatgagtt tattacgacc tgcgtcagaa ccggaggttg    540
tggcattggt tattggcttc atatgccttt ggggtatttt ttgtttatat ggtgcctgac    600
gcaattcacg cttttttgtca cctgtagtta cgctggcatt tatctctttc accaatatac    660
ggagcgagca tttccgataa gaaaaatatt tcagagaaaa cgcccgttg  aagggatgtg    720 gaaattcact ttaagcgtca gttttaatga aatcctagac tccatttccc agcagggtgg    780 caccccttgct attggtagct cactgggggc tgggaagcc  gctgtctatc gggtcgcgcg    840
```

-continued

```
ccagattagt aacggtttat ccaaaccagc acagatgatg atcggctaac atgcatccac    900
cggcagcacc ggccgtttta tgcttgggat tattgatatg ccgaaaagga tacaacatct    960
ggaagaaaaa gacgaaggcc ggaataagcg cccattctgc aaaattgtta caacttagtc   1020
gcgccatcag ggaatgaaaa atcaatccgt cttttttcggc atgagcaacc aacattttca   1080
aggtatcatc ctgatgcgca atatcggcat cggttagcca taaccatttt acctgtccgg   1140
cggccttaat accttgatca gatggttcgt ggtgttgtta ccttgccgaa gggcaccggt   1200
aaaaatgttc gcgtcggtgt tttcgcccgt ggcccgaaag ctgaagaagc taaagctgct   1260
ggtgcagaag ttgtcggcgc agaagacctg atggaagcca ttcagggcgg cagcattgat   1320
ttcgatcgtg atgcccttta tactgaaatt gccttgcgct gccataatga agcagcctcc   1380
ggtgttttgg cagatttaag cgctgcctga ttttcgtgat cctctagagt ctatgaaatg   1440
gagattcatt t atg cct ctc tct tat tcg gat aac cat cca gtc atc gat   1490
             Met Pro Leu Ser Tyr Ser Asp Asn His Pro Val Ile Asp
              1               5                  10
```

```
agc caa aaa cac gcc cca cgt aaa aaa ctg ttt cta tct tgt gcc tgt    1538
Ser Gln Lys His Ala Pro Arg Lys Lys Leu Phe Leu Ser Cys Ala Cys
 15              20                  25
```

```
tta gga tta agc ctt gcc tgc ctt tcc agt aat gcc tgg gcg agt gtt    1586
Leu Gly Leu Ser Leu Ala Cys Leu Ser Ser Asn Ala Trp Ala Ser Val
30              35                  40                  45
```

```
gag ccg tta tcc gtt agc ggc aat aaa atc tac gca ggt gaa aaa gcc    1634
Glu Pro Leu Ser Val Ser Gly Asn Lys Ile Tyr Ala Gly Glu Lys Ala
             50                  55                  60
```

```
aaa agt ttt gcc ggc aac agc tta ttc tgg agt aat aat ggt tgg ggt    1682
Lys Ser Phe Ala Gly Asn Ser Leu Phe Trp Ser Asn Asn Gly Trp Gly
         65                  70                  75
```

```
ggg gaa aaa ttc tac aca gcc gat acc gtt gcg tcg ctg aaa aaa gac    1730
Gly Glu Lys Phe Tyr Thr Ala Asp Thr Val Ala Ser Leu Lys Lys Asp
             80                  85                  90
```

```
tgg aaa tcc agc att gtt cgc gcc gct atg ggc gtt cag gaa agc ggt    1778
Trp Lys Ser Ser Ile Val Arg Ala Ala Met Gly Val Gln Glu Ser Gly
     95                 100                 105
```

```
ggt tat ctg cag gac ccg gct ggc aac aag gcc aaa gtt gaa aga gtg    1826
Gly Tyr Leu Gln Asp Pro Ala Gly Asn Lys Ala Lys Val Glu Arg Val
110             115                 120                 125
```

```
gtg gat gcc gca atc gcc aac gat atg tat gtg att att gac tgg cac    1874
Val Asp Ala Ala Ile Ala Asn Asp Met Tyr Val Ile Ile Asp Trp His
                130                 135                 140
```

```
tca cat tct gca gaa aac aat cgc agt gaa gcc att cgc ttc ttc cag    1922
Ser His Ser Ala Glu Asn Asn Arg Ser Glu Ala Ile Arg Phe Phe Gln
            145                 150                 155
```

```
gaa atg gcg cgc aaa tat ggc aac aag ccg aat gtc att tat gaa atc    1970
Glu Met Ala Arg Lys Tyr Gly Asn Lys Pro Asn Val Ile Tyr Glu Ile
        160                 165                 170
```

```
tac aac gag ccg ctt cag gtt tca tgg agc aat acc att aaa cct tat    2018
Tyr Asn Glu Pro Leu Gln Val Ser Trp Ser Asn Thr Ile Lys Pro Tyr
175                 180                 185
```

```
gcc gaa gcc gtg att tcc gcc att cgc gcc att gac ccg gat aac ctg    2066
Ala Glu Ala Val Ile Ser Ala Ile Arg Ala Ile Asp Pro Asp Asn Leu
190                 195                 200                 205
```

```
att att gtc ggt acg ccc agt tgg tcg caa aac gtt gat gaa gcg tcg    2114
Ile Ile Val Gly Thr Pro Ser Trp Ser Gln Asn Val Asp Glu Ala Ser
                210                 215                 220
```

```
cgc gat cca atc aac gcc aag aat atc gcc tat acg ctg cat ttc tac    2162
Arg Asp Pro Ile Asn Ala Lys Asn Ile Ala Tyr Thr Leu His Phe Tyr
            225                 230                 235
```

-continued

| | | |
|---|---|---|
| gcg gga acc cat ggt gag tca tta cgc act aaa gcc cgc cag gcg tta<br>Ala Gly Thr His Gly Glu Ser Leu Arg Thr Lys Ala Arg Gln Ala Leu<br>240 245 250 | 2210 |
| aat aac ggt att gcg ctt ttc gtc acc gag tgg ggc gcc gtt aac gcg<br>Asn Asn Gly Ile Ala Leu Phe Val Thr Glu Trp Gly Ala Val Asn Ala<br>255 260 265 | 2258 |
| gac ggc aat ggc gga gtg aac cag aca gat acc gac gcc tgg gta acg<br>Asp Gly Asn Gly Gly Val Asn Gln Thr Asp Thr Asp Ala Trp Val Thr<br>270 275 280 285 | 2306 |
| ttc atg cgt gac aac aac atc agc aac gca aac tgg gcg tta aat gat<br>Phe Met Arg Asp Asn Asn Ile Ser Asn Ala Asn Trp Ala Leu Asn Asp<br>290 295 300 | 2354 |
| aaa agc gaa ggg gca tca acc tat tat ccg gac tct aaa aac ctg acc<br>Lys Ser Glu Gly Ala Ser Thr Tyr Tyr Pro Asp Ser Lys Asn Leu Thr<br>305 310 315 | 2402 |
| gag tcg ggt aaa ata gta aaa tcg atc att caa agc tgg cca tat aaa<br>Glu Ser Gly Lys Ile Val Lys Ser Ile Ile Gln Ser Trp Pro Tyr Lys<br>320 325 330 | 2450 |
| gcg ggc agc gcc gcc agt aca aca acc gat cag tca acc gat acc acc<br>Ala Gly Ser Ala Ala Ser Thr Thr Thr Asp Gln Ser Thr Asp Thr Thr<br>335 340 345 | 2498 |
| atg gca cca ccg ttg acg aac cga cca caa ccg aca cac cgg caa acc<br>Met Ala Pro Pro Leu Thr Asn Arg Pro Gln Pro Thr His Arg Gln Thr<br>350 355 360 365 | 2546 |
| gct gat tgc tgc aat gcc aac gtt tac ccc aac tgg gtt agc aaa gac<br>Ala Asp Cys Cys Asn Ala Asn Val Tyr Pro Asn Trp Val Ser Lys Asp<br>370 375 380 | 2594 |
| tgg gcg ggc cgg cag cga ctc ata acg aag cag gcc aat cga tcg tct<br>Trp Ala Gly Arg Gln Arg Leu Ile Thr Lys Gln Ala Asn Arg Ser Ser<br>385 390 395 | 2642 |
| aca aag gga acc tgt ata ccg caa act ggt aca ctt cat ccg ttc cgg<br>Thr Lys Gly Thr Cys Ile Pro Gln Thr Gly Thr Leu His Pro Phe Arg<br>400 405 410 | 2690 |
| gca gcg att cct cct ggg cac agg ttg gta gct gta act aat tga<br>Ala Ala Ile Pro Pro Gly His Arg Leu Val Ala Val Thr Asn<br>415 420 425 | 2735 |
| ttaatctttt cacccccaaa ataacagggc tgcgattgca gcctgatacg caacattcca | 2795 |
| ttacttaatt gcgttcaaaa gcgcccaaat ccggtgcgct gccttgtaac taatatgatt | 2855 |
| tctctttcgt acccgcgtta atcagctttg agttagccga cagacggaac agcgaggttg | 2915 |
| ccggcaacgt gccgtcatta tcacgagata cggtagccag cgaggtgtcc aggctgacga | 2975 |
| atcggacgcg gaagccgctg tccgtatcca tgagttgact cgcatccgca ttactgaccg | 3035 |
| ttgcagaagc agacagagac acgttgttgc ggaagtaatg tttctgtcct gactggacgt | 3095 |
| tgctcccgaa agcataatta atgccgtttt tatatgacgt gttatttatt accgtacgcc | 3155 |
| gccgcgttat tgttctggtc aaaaccttg ctcacgttgc caaacgcgac gcaacgggta | 3215 |
| atgcgatgat tgccgaccgc tggttcctcc cagtttgaac ccgttggcat tgccggcgaa | 3275 |
| cgcgctnnnn nnnnnnnnnn nnnnnnnnnn nnnnnnnnnn nnnnnnnnnn nnnnnnnnnn | 3335 |
| nnnnnnnnnn nnnnnnnnnn nnnnnnnnnn nnnnnnnnnn nnnnnnnnnn nnnnnnnnnn | 3395 |
| nnnnnnnnnn nnnnnnnnnn nnnnnnnnnn nnnnnnnnnn nnnnnnnnnn nnnnnnnnnn | 3455 |
| nnnnnnnnnn nnnnnnnnnn nnnnnnnnnn nnnnnnnnnn nnnnnnnnnn nnnnnnnnnn | 3515 |
| nnnnnnnnnn nnnnnnnnnn nnnnnnnnnn nnnnnnnnnn nnnnnnnnnn nnnnnnnnnn | 3575 |
| nnnnnnnnnn nnnnnnnnnn nnnnnnnnnn nnnnnnnnnn nnnnnnnnnn nnnnnnnnnn | 3635 |

```
nnnnnnnnnn nnnnnnnnnn nnnnnnnnnn nnnnnnnnnn nnnnnnnnnn nnnnnnnnnn    3695
nnnnnnnnnn nnnnnnnnnn nnnnnnnnnn nnnnnnnnnn nnnnnnnnnn nnnnnnnnnn    3755
nnnnnnnnnn nnnnnnnnnn nnnnnnnnnn nnnnnnnnnn nnnnnnnnnn nnnnnnnnnn    3815
nnnnnnnnnn nnnnnnnnnn nnnnnnnnnn nnnnnnnnnn nnnnnnnnnn nnnnnnnnnn    3875
nnnnnnnnnn nnnnnnnnnn nnnnnnnnnn nnnnnnnnnn nnnnnnnnnn nnnnnnnnnn    3935
nnnnnnnnnn nnnnnnnnnn nnnnnnnnnn nnnnnnnnnn nnnnnnnnnn nnnnnnnnnn    3995
nnnnnnnnnn nnnnnnnnnn nnnnnnnnnn nnnnnnnnnn nnnnnnnnnn nnnnnnnnnn    4055
nnnnnnnnnn nnnnnnnnnn nnnnnnnnnn nnnnnnnnnn nnnnnnnnnn nnnnnnnnnn    4115
nnnnnnnnnn nnnnnnnnnn nnnnnnnnnn nnnnnnnnnn nnnnnnnnnn nnnnnnnnnn    4175
nnnnnnnnnn nnnnnnnnnn nnnnnnnnnn nnnnnnnnnn nnnnnnnnnn nnnnnnnnnn    4235
nnnnnnnnnn nnnnnnnnnn nnnnnnnnnn nnnnnnnnnn nnnnnngatc ctctagagtc    4295
gacctgcagg aattcactgg ccgtcgtttt acaacgtcgt gactgggaaa accctggcgt    4355
tacccaactt aatcgccttg cagcacatcc ccctttcgcc agctggcgta atagcgaaga    4415
ggcccgcacc gatcgccctt cccaacagtt gcgcagcctg aatggcgaat ggcgcctgat    4475
gcggtatttt ctccttacgc atctgtgcgg tatttcacac cgcataggcg cgcctatggt    4535
gcactctcag tacaatctgc tctgatgccg catagttaag ccagccccga cacccgccaa    4595
cacccgctga cgcgccctga cgggcttgtc tgctcccggc atccgcttac agacaagctg    4655
tgaccgtctc cggagctgca tgtgtcaga ggttttcacc gtcatcaccg aaacgcgcga    4715
gacgaaaggg cctcgtgata cgcctatttt tataggttaa tgtcatgata ataatggttt    4775
cttagacgtc aggtggcact tttcggggaa atgtgcgcgg aacccctatt tgtttatttt    4835
tctaaataca ttcaaatatg tatccgctca tgagacaata accctgataa atgcttcaat    4895
aatattgaaa aaggaagagt atg agt att caa cat ttc cgt gtc gcc ctt att    4948
              Met Ser Ile Gln His Phe Arg Val Ala Leu Ile
                      430                 435 ccc ttt ttt gcg gca ttt tgc ctt cct gtt ttt gct cac cca gaa acg        4996
Pro Phe Phe Ala Ala Phe Cys Leu Pro Val Phe Ala His Pro Glu Thr
440             445                 450 ctg gtg aaa gta aaa gat gct gaa gat cag ttg ggt gca cga gtg ggt        5044
Leu Val Lys Val Lys Asp Ala Glu Asp Gln Leu Gly Ala Arg Val Gly
455                 460                 465                 470 tac atc gaa ctg gat ctc aac agc ggt aag atc ctt gag agt ttt cgc        5092
Tyr Ile Glu Leu Asp Leu Asn Ser Gly Lys Ile Leu Glu Ser Phe Arg
                475                 480                 485 ccc gaa gaa cgt ttt cca atg atg agc act ttt aaa gtt ctg cta tgt        5140
Pro Glu Glu Arg Phe Pro Met Met Ser Thr Phe Lys Val Leu Leu Cys
            490                 495                 500 ggc gcg gta tta tcc cgt att gac gcc ggg caa gag caa ctc ggt cgc        5188
Gly Ala Val Leu Ser Arg Ile Asp Ala Gly Gln Glu Gln Leu Gly Arg
        505                 510                 515 cgc ata cac tat tct cag aat gac ttg gtt gag tac tca cca gtc aca        5236
Arg Ile His Tyr Ser Gln Asn Asp Leu Val Glu Tyr Ser Pro Val Thr
    520                 525                 530 gaa aag cat ctt acg gat ggc atg aca gta aga gaa tta tgc agt gct        5284
Glu Lys His Leu Thr Asp Gly Met Thr Val Arg Glu Leu Cys Ser Ala
535                 540                 545                 550 gcc ata acc atg agt gat aac act gcg gcc aac tta ctt ctg aca acg        5332
Ala Ile Thr Met Ser Asp Asn Thr Ala Ala Asn Leu Leu Leu Thr Thr
                555                 560                 565 atc gga gga ccg aag gag cta acc gct ttt ttg cac aac atg ggg gat        5380
Ile Gly Gly Pro Lys Glu Leu Thr Ala Phe Leu His Asn Met Gly Asp
```

```
                Ile Gly Gly Pro Lys Glu Leu Thr Ala Phe Leu His Asn Met Gly Asp
                            570                 575                 580 cat gta act cgc ctt gat cgt tgg gaa ccg gag ctg aat gaa gcc ata        5428
His Val Thr Arg Leu Asp Arg Trp Glu Pro Glu Leu Asn Glu Ala Ile
            585                 590                 595 cca aac gac gag cgt gac acc acg atg cct gta gca atg gca aca acg        5476
Pro Asn Asp Glu Arg Asp Thr Thr Met Pro Val Ala Met Ala Thr Thr
600                 605                 610 ttg cgc aaa cta tta act ggc gaa cta ctt act cta gct tcc cgg caa        5524
Leu Arg Lys Leu Leu Thr Gly Glu Leu Leu Thr Leu Ala Ser Arg Gln
615                 620                 625                 630 caa tta ata gac tgg atg gag gcg gat aaa gtt gca gga cca ctt ctg        5572
Gln Leu Ile Asp Trp Met Glu Ala Asp Lys Val Ala Gly Pro Leu Leu
            635                 640                 645 cgc tcg gcc ctt ccg gct ggc tgg ttt att gct gat aaa tct gga gcc        5620
Arg Ser Ala Leu Pro Ala Gly Trp Phe Ile Ala Asp Lys Ser Gly Ala
            650                 655                 660 ggt gag cgt ggg tct cgc ggt atc att gca gca ctg ggg cca gat ggt        5668
Gly Glu Arg Gly Ser Arg Gly Ile Ile Ala Ala Leu Gly Pro Asp Gly
            665                 670                 675 aag ccc tcc cgt atc gta gtt atc tac acg acg ggg agt cag gca act        5716
Lys Pro Ser Arg Ile Val Val Ile Tyr Thr Thr Gly Ser Gln Ala Thr
680                 685                 690 atg gat gaa cga aat aga cag atc gct gag ata ggt gcc tca ctg att        5764
Met Asp Glu Arg Asn Arg Gln Ile Ala Glu Ile Gly Ala Ser Leu Ile
695                 700                 705                 710 aag cat tgg taa ctgtcagacc aagtttactc atatatactt tagattgatt           5816
Lys His Trp taaaacttca ttttttaattt aaaaggatct aggtgaagat cctttttgat aatctcatga    5876
ccaaaatccc ttaacgtgag ttttcgttcc actgagcgtc agacccgta gaaaagatca      5936 aaggatcttc ttgagatcct ttttttctgc gcgtaatctg ctgcttgcaa acaaaaaaac    5996
caccgctacc agcggtggtt tgtttgccgg atcaagagct accaactctt tttccgaagg    6056
taactggctt cagcagagcg cagataccaa atactgtcct tctagtgtag ccgtagttag    6116
gccaccactt caagaactct gtagcaccgc ctacatacct cgctctgcta atcctgttac    6176
cagtggctgc tgccagtggc gataagtcgt gtcttaccgg gttggactca agacgatagt    6236
taccggataa ggcgcagcgg tcgggctgaa cggggggttc gtgcacacag cccagcttgg    6296
agcgaacgac ctacaccgaa ctgagatacc tacagcgtga gctatgagaa agcgccacgc    6356
ttcccgaagg gagaaaggcg acaggtatc cggtaagcgg cagggtcgga acaggagagc     6416
gcacgaggga gcttccaggg ggaaacgcct ggtatcttta tagtcctgtc gggtttcgcc    6476
acctctgact tgagcgtcga ttttttgtgat gctcgtcagg ggggcggagc ctatggaaaa   6536
acgccagcaa cgcggccttt ttacggttcc tggccttttg ctggccttt gctcacatgt     6596 tctttcctgc gttatcccct gattctgtgg ataaccgtat taccgccttt gagtgagctg    6656
ataccgctcg ccgcagccga acgaccgagc gcagcgagtc agtgagcgag gaagcggcgc    6716
gccagcggaa gagcgcccaa tacgcaaacc gcctctcccc gcgcgttggc cgattcatta    6776
atgcagctgg cacgacaggt ttcccgactg gaaagcgggc agtgagcgca acgcaattaa    6836
tgtgagttag ctcactcatt aggcacccca ggctttacac tttatgcttc cggctcgtat    6896
gttgtgtgga attgtgagcg gataacaatt tcacacagga aacagctatg accatgatta    6956
cgccaagctt gcatgccaat tctcatgttt gacagcttat catcgataag ctttaatgcg    7016
gtagtttatc acagttaaat tgctaacgca gtcaggcacc gtgt atg aaa tct aac     7072
```

```
                                     Met Lys Ser Asn
                                                  715 aat gcg ctc atc gtc atc ctc ggc acc gtc acc ctg gat gct gta ggc      7120
Asn Ala Leu Ile Val Ile Leu Gly Thr Val Thr Leu Asp Ala Val Gly
        720                 725                 730 ata ggc ttg gtt atg ccg gta ctg ccg ggc ctc ttg cgg gat atc gtc      7168
Ile Gly Leu Val Met Pro Val Leu Pro Gly Leu Leu Arg Asp Ile Val
735                 740                 745 cat tcc gac agc atc gcc agt cac tat ggc gtg ctg cta gcg cta tat      7216
His Ser Asp Ser Ile Ala Ser His Tyr Gly Val Leu Leu Ala Leu Tyr
750                 755                 760                 765 gcg ttg atg caa ttt cta tgc gca ccc gtt ctc gga gca ctg tcc gac      7264
Ala Leu Met Gln Phe Leu Cys Ala Pro Val Leu Gly Ala Leu Ser Asp
            770                 775                 780 cgc ttt ggc cgc cgc cca gtc ctg ctc gct tcg cta ctt gga gcc act      7312
Arg Phe Gly Arg Arg Pro Val Leu Leu Ala Ser Leu Leu Gly Ala Thr
                785                 790                 795 atc gac tac gcg atc atg gcg acc aca ccc gtc ctg tgg atc ctc tac      7360
Ile Asp Tyr Ala Ile Met Ala Thr Thr Pro Val Leu Trp Ile Leu Tyr
                    800                 805                 810 gcc gga cgc atc gtg gcc ggc atc acc ggc gcc aca ggt gcg gtt gct      7408
Ala Gly Arg Ile Val Ala Gly Ile Thr Gly Ala Thr Gly Ala Val Ala
815                 820                 825 ggc gcc tat atc gcc gac atc acc gat ggg gaa gat cgg gct cgc cac      7456
Gly Ala Tyr Ile Ala Asp Ile Thr Asp Gly Glu Asp Arg Ala Arg His
830                 835                 840                 845 ttc ggg ctc atg agc gct tgt ttc ggc gtg ggt atg gtg gca ggc ccc      7504
Phe Gly Leu Met Ser Ala Cys Phe Gly Val Gly Met Val Ala Gly Pro
            850                 855                 860 gtg gcc ggg gga ctg ttg ggc gcc atc tcc ttg cat gca cca ttc ctt      7552
Val Ala Gly Gly Leu Leu Gly Ala Ile Ser Leu His Ala Pro Phe Leu
                865                 870                 875 gcg gcg gcg gtg ctc aac ggc ctc aac cta cta ctg ggc tgc ttc cta      7600
Ala Ala Ala Val Leu Asn Gly Leu Asn Leu Leu Leu Gly Cys Phe Leu
                    880                 885                 890 atg cag gag tcg cat aag gga gag cgt cga ccg atg ccc ttg aga gcc      7648
Met Gln Glu Ser His Lys Gly Glu Arg Arg Pro Met Pro Leu Arg Ala
895                 900                 905 ttc aac cca gtc agc tcc ttc cgg tgg gcg cgg ggc atg act atc gtc      7696
Phe Asn Pro Val Ser Ser Phe Arg Trp Ala Arg Gly Met Thr Ile Val
910                 915                 920                 925 gcc gca ctt atg act gtc ttc ttt atc atg caa ctc gta gga cag gtg      7744
Ala Ala Leu Met Thr Val Phe Phe Ile Met Gln Leu Val Gly Gln Val
            930                 935                 940 ccg gca gcg ctc tgg gtc att ttc ggc gag gac cgc ttt cgc tgg agc      7792
Pro Ala Ala Leu Trp Val Ile Phe Gly Glu Asp Arg Phe Arg Trp Ser
                945                 950                 955 gcg acg atg atc ggc ctg tcg ctt gcg gta ttc gga atc ttg cac gcc      7840
Ala Thr Met Ile Gly Leu Ser Leu Ala Val Phe Gly Ile Leu His Ala
                    960                 965                 970 ctc gct caa gcc ttc gtc act ggt ccc gcc acc aaa cgt ttc ggc gag      7888
Leu Ala Gln Ala Phe Val Thr Gly Pro Ala Thr Lys Arg Phe Gly Glu
975                 980                 985 aag cag gcc att atc gcc ggc atg gcg gcc gac gcg ctg ggc tac gtc      7936
Lys Gln Ala Ile Ile Ala Gly Met Ala Ala Asp Ala Leu Gly Tyr Val
990                 995                 1000                1005 ttg ctg gcg ttc gcg acg cga ggc tgg atg gcc ttc ccc att atg           7981
Leu Leu Ala Phe Ala Thr Arg Gly Trp Met Ala Phe Pro Ile Met
                1010            1015            1020
```

| | | | | | | | | | | | | | | |
|---|---|---|---|---|---|---|---|---|---|---|---|---|---|---|
| att | ctt | ctc | gct | tcc | ggc | ggc | atc | ggg | atg | ccc | gcg | ttg | cag | gcc |
| Ile | Leu | Leu | Ala | Ser | Gly | Gly | Ile | Gly | Met | Pro | Ala | Leu | Gln | Ala |
| | | | | 1025 | | | | | 1030 | | | | | 1035 |

8026

| | | | | | | | | | | | | | | |
|---|---|---|---|---|---|---|---|---|---|---|---|---|---|---|
| atg | ctg | tcc | agg | cag | gta | gat | gac | gac | cat | cag | gga | cag | ctt | caa |
| Met | Leu | Ser | Arg | Gln | Val | Asp | Asp | Asp | His | Gln | Gly | Gln | Leu | Gln |
| | | | | 1040 | | | | | 1045 | | | | | 1050 |

8071

| | | | | | | | | | | | | | | |
|---|---|---|---|---|---|---|---|---|---|---|---|---|---|---|
| gga | tcg | ctc | gcg | gct | ctt | acc | agc | cta | act | tcg | atc | act | gga | ccg |
| Gly | Ser | Leu | Ala | Ala | Leu | Thr | Ser | Leu | Thr | Ser | Ile | Thr | Gly | Pro |
| | | | | 1055 | | | | | 1060 | | | | | 1065 |

8116

| | | | | | | | | | | | | | | |
|---|---|---|---|---|---|---|---|---|---|---|---|---|---|---|
| ctg | atc | gtc | acg | gcg | att | tat | gcc | gcc | tcg | gcg | agc | aca | tgg | aac |
| Leu | Ile | Val | Thr | Ala | Ile | Tyr | Ala | Ala | Ser | Ala | Ser | Thr | Trp | Asn |
| | | | | 1070 | | | | | 1075 | | | | | 1080 |

8161

| | | | | | | | | | | | | | | |
|---|---|---|---|---|---|---|---|---|---|---|---|---|---|---|
| ggg | ttg | gca | tgg | att | gta | ggc | gcc | gcc | cta | tac | ctt | gtc | tgc | ctc |
| Gly | Leu | Ala | Trp | Ile | Val | Gly | Ala | Ala | Leu | Tyr | Leu | Val | Cys | Leu |
| | | | | 1085 | | | | | 1090 | | | | | 1095 |

8206

| | | | | | | | | | | | |
|---|---|---|---|---|---|---|---|---|---|---|---|
| ccc | gcg | ttg | cgt | cgc | ggt | gca | tgg | agc | cgg | gcc | acc | tcg | acc | tga |
| Pro | Ala | Leu | Arg | Arg | Gly | Ala | Trp | Ser | Arg | Ala | Thr | Ser | Thr | |
| | | | | 1100 | | | | | 1105 | | | | | |

8251

```
atggaagccg gcggcaccctc gctaacggat tcaccactcc aagaattgga gccaatcaat    8311
tcttgcggag aactgtgaat gcgcaaaacca acccttggca gaacatatcc atcgcgtccg    8371
ccatctccag cagccgcacg cggcgcatct cggggtcgac tctagaggat ccccgcaacg    8431
ctgtcagcgc tttccagtta aacggctcca acgtcgccat aggtaattcc tcgcccggcc    8491
atacgatcgg gcaggtgccg ttggctatcg ccgtcgcctg actcatcaca ctatcttccg    8551
ctgcatcgcg aagggttttg accacttctt ccatctctcc gtgcgccgga tgccatgctc    8611
acgtacgcgg cttatcagat agtcgggcag gccgtcgttc cagcccaatg aggggaagct    8671
ggcgtggagc gatgccagca cctgctcctc aacaccgtaa tggccggcgg cgaacaggca    8731
tcggcggta agcgcttcca gcccttttaat catcacgctg cggcacatct tgatagccga    8791
cacgctgcca acgtggttac caccatagcg ggcgttacat ccaagcgtgg tgagtaattc    8851
agcaattgcc tctgcctgtg gtccccccgt caacagcggc gttcggagtg ccctgggggg    8911
gaccggcgcc atcaccgcta catcgacata agcgccgggc ttaaagcatt tggcagcctg    8971
acgcttggtc tgcggggcga cggagttaag gtcaagaaaa tactgcgtgt cggtcatcag    9031
cggtgcagct tgtgaggcga catccagggc ggatcccgcg gtgacggtgg aaaatatgag    9091
ttcggcacct gtcaacgcgt cagccaggga gattgccgcc gcacgcctc cccgatgcgc     9151
cttcgttatc atcgcatcgc gctcaggacc ttgcagcttg caatcccaga cggtgactgg    9211
gttcactttt gccagtgcat ccgcaagaat gccacctgct tcaccataac ctataaacgt    9271
tattgtcgtc ataacagctc cttacgcggc cacacgtcgg ccggaatgca aacgtcgccc    9331
gcgaacagaa gtcgcgccgt acgcagcaga ccgcagcctg ccaactgccc attatcatca    9391
agccggagcg ccacgctgaa ttgggtaccg agctccgaat tgggtaccga gctcgaatta    9451
attcgagctc ggtacccggg gatcnnnnnn nnnnnnnnnn nnnnnnnnnn nnnnnnnnnn    9511
nnnnnnnnnn nnnnnnnnnn nnnnnnnnnn nnnnnnnnnn nnnnnnnnnn nnnnnnnnnn    9571
nnnnnnnnnn nnnnnnnnnn nnnnnnnnnn nnnnnnnnnn nnnnnnnnnn nnnnnnnnnn    9631
nnnnnnnnnn nnnnnnnnnn nnnnnnnnnn nnnnnnnnnn nnnnnnnnnn nnnnnnnnnn    9691
nnnnnnnnnn nnnnnnnnnn nnnnnnnnnn nnnnnnnnnn nnnnnnnnnn nnnnnnnnnn    9751
nnnnnnnnnn nnnnnnnnnn nnnnnnnnnn nnnnnnnnnn nnnnnnnnnn nnnnnnnnnn    9811
nnnnnnnnnn nnnnnnnnnn nnnnnnnnnn nnnnnnnnnn nnnnnnnnnn nnnnnnnnnn    9871
nnnnnnnnnn nnnnnnnnnn nnnnnnnnnn nnnnnnnnnn nnnnnnnnnn nnnnnnnnnn    9931
```

```
nnnnnnnnnn nnnnnnnnnn nnnnnnnnnn nnnnnnnnnn nnnnnnnnnn nnnnnnnnnn      9991
nnnnnnnnnn nnnnnnnnnn nnnnnnnnnn nnnnnnnnnn nnnnnnnnnn nnnnnnnnnn     10051
nnnnnnnnnn nnnnnnnnnn nnnnnnnnnn nnnnnnnnnn nnnnnnnnnn nnnnnnnnnn     10111
nnnnnnnnnn nnnnnnnnnn nnnnnnnnnn nnnnnnnnnn nnnnnnnnnn nnnnnnnnnn     10171
nnnnnnnnnn nnnnnnnnnn nnnnnnnnnn nnnnnnnnnn nnnnnnnnnn nnnnnnnnnn     10231
nnnnnnnnnn nnnnnnnnnn nnnnnnnnnn nnnnnnnnnn nnnnnnnnnn nnnnnnnnnn     10291
nnnnnnnnnn nnnnnnnnnn nnnnnnnnnn nnnnnnnnnn nnnnnnnnnn nnnnnnnnnn     10351
nnnnnnnnnn nnnnnnnnnn nnnnnnnnnn nnnnnnnnnn nnnnnnnnnn nnnnnnnnnn     10411
nnnnnnnnnn nnnnnnnnnn nnnnnnnnnn nnnnnnnnnn nnnnnnnnnn nnnnnnnnnn     10471
nnnnnnnnnn nnnnnnnnnn nnnnnnnnnn nnnnnnnnnn nnnnnnnnnn nnnnnnnnnn     10531
nnnnnnnnnn nnnnnnnnnn nnnnnnnnnn nnnnnnnnnn nnnnnnnnnn nnnnnnnnnn     10591
nnnnnnnnnn nnnnnnnnnn nnnnnnnnnn nnnnnnnnnn nnnnnnnnnn nnnnnnnnnn     10651
nnnnnnnnnn nnnnnnnnnn nnnnnnnnnn nnnnnnnnnn nnnnnnnnnn nnnnnnnnnn     10711
nnnnnnnnnn nnnnnnnnnn nnnnnnnnnn nnnnnnnnnn nnnnnnnnnn nnnnnnnnnn     10771
nnnnnnnnnn nnnnnnnnnn nnnnnnnnnn nnnnnnnnnn nnnnnnnnnn nnnnnnnnnn     10831
nnnnnnnnnn nnnnnnnnnn nnnnnnnnnn nnnnnnnnnn nnnnnnnnnn nnnnnnnnnn     10891
nnnnnnnnnn nnnnnnnnnn nnnnnnnnnn nnnnnnnnnn nnnnnnnnnn nnnnnnnnnn     10951
nnnnnnnnnn nnnnnnnnnn nnnnnnnnnn nnnnnnnnnn nnnnnnnnnn nnnnnnnnnn     11011
nnnnnnnnnn nnnnnnnnnn nnnnnnnnnn nnnnnnnnnn nnnnnnnnnn nnnnnnnnnn     11071
nnnnnnnnnn nnnnnnnnnn nnnnnnnnnn nnnnnnnnnn nnnnnnnnnn nnnnnnnnnn     11131
nnnnnnnnnn nnnnnnnnnn nnnnnnnnnn nnnnnnnnnn nnnnnnnnnn nnnnnnnnnn     11191
nnnnnnnnnn nnnnnnnnnn nnnnnnnnnn nnnnnnnnnn nnnnnnnnnn nnnnnnnnnn     11251
nnnnnnnnnn nnnnnnnnnn nnnnnnnnnn nnnnnnnnnn nnnnnnnnnn nnnnnnnnnn     11311
nnnnnnnnnn nnnnnnnnnn nnnnnnnnnn nnnnnnnnnn nnnnnnnnnn nnnnnnnnnn     11371
nnnnnnnnnn nnnnnnnnnn nnnnnnnnnn nnnnnnnnnn nnnnnnnnnn nnnnnnnnnn     11431
nnnnnnnnnn nnnnnnnnnn nnnnnnnnnn nnnnnnnnnn nnnnnnnnnn nnnnnnnnnn     11491
nnnnnnnnnn nnnnnnnnnn nnnnnnnnnn nnnnnnnnnn nnnnnnnnnn nnn           11544
```

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctgttccgtt accaacac                                                      18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

-continued

```
gtgaatggga tcacgagt                                                  18
```

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
accatcagca tcaacgccca acaacg                                         26
```

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
gactggatgg ttatccgaat aagagagagg                                     30
```

<210> SEQ ID NO 17
<211> LENGTH: 11772
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (144)..(1143)
<223> OTHER INFORMATION: a, c, g, t, unknown, or other
<220> FEATURE:
<221> NAME/KEY: modified_base
<222> LOCATION: (5753)..(7567)
<223> OTHER INFORMATION: a, c, g, t, unknown, or other

<400> SEQUENCE: 17

```
atcgatgaat tgatccgaag ttcctattct ctagaaagta taggaacttc gaattgtcga    60
caagcttgat ctggcttatc gaaattaata cgactcacta tagggagacc ggaattcccc   120
tgcaggtcga ctctagagga tcannnnnnn nnnnnnnnnn nnnnnnnnnn nnnnnnnnnn   180
nnnnnnnnnn nnnnnnnnnn nnnnnnnnnn nnnnnnnnnn nnnnnnnnnn nnnnnnnnnn   240
nnnnnnnnnn nnnnnnnnnn nnnnnnnnnn nnnnnnnnnn nnnnnnnnnn nnnnnnnnnn   300
nnnnnnnnnn nnnnnnnnnn nnnnnnnnnn nnnnnnnnnn nnnnnnnnnn nnnnnnnnnn   360
nnnnnnnnnn nnnnnnnnnn nnnnnnnnnn nnnnnnnnnn nnnnnnnnnn nnnnnnnnnn   420
nnnnnnnnnn nnnnnnnnnn nnnnnnnnnn nnnnnnnnnn nnnnnnnnnn nnnnnnnnnn   480
nnnnnnnnnn nnnnnnnnnn nnnnnnnnnn nnnnnnnnnn nnnnnnnnnn nnnnnnnnnn   540
nnnnnnnnnn nnnnnnnnnn nnnnnnnnnn nnnnnnnnnn nnnnnnnnnn nnnnnnnnnn   600
nnnnnnnnnn nnnnnnnnnn nnnnnnnnnn nnnnnnnnnn nnnnnnnnnn nnnnnnnnnn   660
nnnnnnnnnn nnnnnnnnnn nnnnnnnnnn nnnnnnnnnn nnnnnnnnnn nnnnnnnnnn   720
nnnnnnnnnn nnnnnnnnnn nnnnnnnnnn nnnnnnnnnn nnnnnnnnnn nnnnnnnnnn   780
nnnnnnnnnn nnnnnnnnnn nnnnnnnnnn nnnnnnnnnn nnnnnnnnnn nnnnnnnnnn   840
nnnnnnnnnn nnnnnnnnnn nnnnnnnnnn nnnnnnnnnn nnnnnnnnnn nnnnnnnnnn   900
nnnnnnnnnn nnnnnnnnnn nnnnnnnnnn nnnnnnnnnn nnnnnnnnnn nnnnnnnnnn   960
```

```
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnnnnnn nnnnnnnnnn nnnnnnnnnn   1140
nnnagcgcgt tcgccggcaa tgccaacggg ttcaaactgg aggaaccag cggtcggcaa     1200 tcatcgcatt acccgttgcg tcgcgtttgg caacgtgagc aaaggttttg accagaacaa   1260
taacgcggcg gcgtacggta ataaataaca cgtcatataa aaacggcatt aattatgctt   1320 tcggagcaa cgtccagtca ggacagaaac attacttccg caacaacgtg tctctgtctg    1380
cttctgcaac ggtcagtaat gcggatgcga gtcaactcat ggatacggac agcggcttcc   1440
gcgtccgatt cgtcagcctg gacacctcgc tggctaccgt atctcgtgat aatgacggca   1500
cgttgccggc aacctcgctg ttccgtctgt cggctaactc aaagctgatt aacgcgggta   1560
cgaaagagaa atcatattag ttacaaggca gcgcaccgga tttgggcgct tttgaacgca   1620
attaagtaat ggaatgttgc gtatcaggct gcaatcgcag ccctgttatt tgggggtga    1680 aaagattaat caattagtta cagctaccaa cctgtgccca ggaggaatcg ctgcccggaa   1740
cggatgaagt gtaccagttt gcggtataca ggttcccttt gtagacgatc gattggcctg   1800
cttcgttatg agtcgctgcc ggcccgccca gtctttgcta acccagttgg ggtaaacgtt   1860
ggcattgcag caatcagcgg tttgccggtg tgtcggttgt ggtcggttcg tcaacggtgg   1920
tgccatggtg gtatcggttg actgatcggt tgttgtactg gcggcgctgc ccgctttata   1980
tggccagctt tgaatgatcg atttactat tttacccgac tcggtcaggt ttttagagtc    2040
cggataatag gttgatgccc cttcgctttt atcatttaac gcccagtttg cgttgctgat   2100
gttgttgtca cgcatgaacg ttacccaggc gtcggtatct gtctggttca ctccgccatt   2160
gccgtccgcg ttaacggcgc cccactcggt gacgaaaagc gcaataccgt tatttaacgc   2220
ctggcgggct ttagtgcgta atgactcacc atgggttccc gcgtagaaat gcagcgtata   2280
ggcgatattc ttggcgttga ttggatcgcg cgacgcttca tcaacgtttt gcgaccaact   2340
gggcgtaccg acaataatca ggttatccgg gtcaatggcg cgaatggcgg aaatcacggc   2400
ttcggcataa ggtttaatgg tattgctcca tgaaacctga agcggctcgt tgtagatttc   2460
ataaatgaca ttcggcttgt tgccatattt gcgcgccatt tcctggaaga agcgaatggc   2520
ttcactgcga ttgtttttctg cagaatgtga gtgccagtca taatcacat acatatcgtt   2580 ggcgattgcg gcatccacca ctctttcaac tttggccttg ttgccagccg ggtcctgcag   2640
ataaccaccg ctttcctgaa cgcccatagc ggcgcgaaca atgctggatt tccagtctttt  2700 tttcagcgac gcaacggtat cggctgtgta gaattttttcc ccaccccaac cattattact  2760
ccagaataag ctgttgccgg caaaactttt ggcttttca cctgcgtaga ttttattgcc    2820
gctaacggat aacggctcaa cactcgccca ggcattactg gaaaggcagg caaggcttaa   2880
tcctaaacag gcacaagata gaaacagttt tttacgtggg gcgtgttttt ggctatcgat   2940
gactggatgg ttatccgaat aagagagagg cataaatgaa tctccatttc atagactcta   3000
gaggatcacg aaaatcaggc agcgcttaaa tctgccaaaa caccggaggc tgcttcatta   3060
tggcagcgca aggcaatttc agtataaagg gcatcacgat cgaaatcaat gctgccgccc   3120
tgaatggctt ccatcaggtc ttctgcgccg acaacttctg caccagcagc tttagcttct   3180
tcagctttcg ggccacgggc gaaaacaccg acgcgaacat ttttaccggt gcccttcggc   3240
aaggtaacaa caccacgaac catctgatca aggtattaag gccgccggac aggtaaaatg   3300
gttatggcta accgatgccg atattgcgca tcaggatgat accttgaaaa tgttggttgc   3360
```

```
tcatgccgaa aaagacggat tgattttca ttccctgatg gcgcgactaa gttgtaacaa    3420
ttttgcagaa tgggcgctta ttccggcctt cgtctttttc ttccagatgt tgtatccttt    3480
tcggcatatc aataatccca agcataaaac ggccggtgct gccggtggat gcatgttagc    3540
cgatcatcat ctgtgctggt ttggataaac cgttactaat ctggcgcgcg acccgataga    3600
cagcggcttc cccagccccc agtgagctac aatagcaag ggtgccaccc tgctggaaaa    3660
tggagtctag gatttcatta aaactgacgc ttaaagtgaa tttccacatc ccttcaacgg    3720
gcgtttttct ctgaaatatt tttcttatcg gaaatgctcg ctccgtatat tggtgaaaga    3780
gataaatgcc agcgtaacta caggtgacaa aaagcgtgaa ttgcgtcagg caccatataa    3840
acaaaaaata ccccaaaggc atatgaagcc aataaccaat gccacaacct ccggttctga    3900
cgcaggtcgt aataaactca taaatagtga ccagtttaaa gcggttacac agccgcaaca    3960
tcccggttgg accagccgat attcataaaa agtataatca gcatacaaag caaggcatct    4020
ggcttgacct cggcaggcca tcccaatctt gaagtgccta aaatcaagat accgcctaac    4080
cctaccaaca tacctatcgc cgcactaaaa aaatcggctc tgatgcaaaa ggcaaggaca    4140
tcatcaaatt ggttaaaatc ttttcctga aaagcttttg aaccgtaatg cagcaaggtt    4200
tgccatgact gaaaacgggt aatatccgaa atcagggtag caaaagtcgt aatcaaaagc    4260
atgacaccaa acaggttcaa tcccaatgtc tgggatgtcc atgcgacata acaaaactg    4320 cataccgcat tcaaaacacg gcctgtaatc agaatgccgg tattgccaat gatacgggaa    4380
aagacagatc gaatttgatg ccgtggataa attgccggtt gatcgatccc cgggtaccga    4440
gctcgaattc cgagcttggc gcgcctatgc ggtgtgaaat accgcacaga tgcgtaagga    4500
gaaaataccg catcaggcgc cattcgccat tcaggctgcg caactgttgg gaagggcgat    4560
cggtgcgggc ctcttcgcta ttacgccagc tggcgaaagg gggatgtgct gcaaggcgat    4620
taagttgggt aacgccaggg ttttcccagt cacgacgttg taaaacgacg gccagtgaat    4680
tccatcaacg cttgctgtaa ccaggagcca aagctatgaa tgtaccttt agctactcgt    4740 cacccaccct gagcgttgag gcgttaaagc actctattgc ttataagctg atgtttatca    4800
tcggcaaaga cccggctatc gctaacaagc atgaatggct caacgccacg ctgttcgccg    4860
ttcgcgatcg tatggttgag cgctggctgc gctcaaaccg cgcgcacgtc tctcaggaag    4920
ttcgccaggt ttactacctg tcgatggaat ttttgattgg ccgtacgttg tccaacgcgc    4980
tgttatcgct cggcatttat gaggatgtga acagcgcgct ggaagagatg gggctgaacc    5040
ttgaagaatt aattgatgaa gaaaacgacc cgggcttagg caacggcggt cttggtcgtc    5100
tggcggcctg cttcctcgat tcgcttgcgg cgctgggggtt accgggccgc ggctacggta    5160
ttcgctacga ctacgggatg tttaagcaga atatcgtcga tgggcggcag aaagaatccc    5220
cggattactg gctggaatac ggtaacccgt gggagttcga gcgccataat acgcgctaca    5280
aagtgcgctt cggcggacgc attcagcagg aaggtaaata ctcccgctgg gtggagaccg    5340
aagagattat tgccgaagcc tatgaccaga ttatccctgg cttcgacacc gacgccacca    5400
acacgctgcg cctgtggagc gcccaggcca gcagcgagat taacctcggt aaattcaacc    5460
agggcgacta cttcgcggcg gtggaagata aaaaccattc gagaacgtg tcgcgggtac    5520 tctatccgga tgactcgacc tattcaggac gcgagctgcg cctgcggcag gagtacttcc    5580
tcgtttcggc gacggtgcag gacatcctca gccgccacta ccagctgcat aaaacctacg    5640
ccaacctggc ggacaaaatc gcgattcatc tcaacgacac gaacccggtg ctgtcgattc    5700
```

-continued

```
cggagctgat gcgcctgctg attgacgagc ataagatcag ctgggatgag ggnnnnnnnn    5760
nnnnnnnnnn nnnnnnnnnn nnnnnnnnnn nnnnnnnnnn nnnnnnnnnn nnnnnnnnnn    5820
nnnnnnnnnn nnnnnnnnnn nnnnnnnnnn nnnnnnnnnn nnnnnnnnnn nnnnnnnnnn    5880
nnnnnnnnnn nnnnnnnnnn nnnnnnnnnn nnnnnnnnnn nnnnnnnnnn nnnnnnnnnn    5940
nnnnnnnnnn nnnnnnnnnn nnnnnnnnnn nnnnnnnnnn nnnnnnnnnn nnnnnnnnnn    6000
nnnnnnnnnn nnnnnnnnnn nnnnnnnnnn nnnnnnnnnn nnnnnnnnnn nnnnnnnnnn    6060
nnnnnnnnnn nnnnnnnnnn nnnnnnnnnn nnnnnnnnnn nnnnnnnnnn nnnnnnnnnn    6120
nnnnnnnnnn nnnnnnnnnn nnnnnnnnnn nnnnnnnnnn nnnnnnnnnn nnnnnnnnnn    6180
nnnnnnnnnn nnnnnnnnnn nnnnnnnnnn nnnnnnnnnn nnnnnnnnnn nnnnnnnnnn    6240
nnnnnnnnnn nnnnnnnnnn nnnnnnnnnn nnnnnnnnnn nnnnnnnnnn nnnnnnnnnn    6300
nnnnnnnnnn nnnnnnnnnn nnnnnnnnnn nnnnnnnnnn nnnnnnnnnn nnnnnnnnnn    6360
nnnnnnnnnn nnnnnnnnnn nnnnnnnnnn nnnnnnnnnn nnnnnnnnnn nnnnnnnnnn    6420
nnnnnnnnnn nnnnnnnnnn nnnnnnnnnn nnnnnnnnnn nnnnnnnnnn nnnnnnnnnn    6480
nnnnnnnnnn nnnnnnnnnn nnnnnnnnnn nnnnnnnnnn nnnnnnnnnn nnnnnnnnnn    6540
nnnnnnnnnn nnnnnnnnnn nnnnnnnnnn nnnnnnnnnn nnnnnnnnnn nnnnnnnnnn    6600
nnnnnnnnnn nnnnnnnnnn nnnnnnnnnn nnnnnnnnnn nnnnnnnnnn nnnnnnnnnn    6660
nnnnnnnnnn nnnnnnnnnn nnnnnnnnnn nnnnnnnnnn nnnnnnnnnn nnnnnnnnnn    6720
nnnnnnnnnn nnnnnnnnnn nnnnnnnnnn nnnnnnnnnn nnnnnnnnnn nnnnnnnnnn    6780
nnnnnnnnnn nnnnnnnnnn nnnnnnnnnn nnnnnnnnnn nnnnnnnnnn nnnnnnnnnn    6840
nnnnnnnnnn nnnnnnnnnn nnnnnnnnnn nnnnnnnnnn nnnnnnnnnn nnnnnnnnnn    6900
nnnnnnnnnn nnnnnnnnnn nnnnnnnnnn nnnnnnnnnn nnnnnnnnnn nnnnnnnnnn    6960
nnnnnnnnnn nnnnnnnnnn nnnnnnnnnn nnnnnnnnnn nnnnnnnnnn nnnnnnnnnn    7020
nnnnnnnnnn nnnnnnnnnn nnnnnnnnnn nnnnnnnnnn nnnnnnnnnn nnnnnnnnnn    7080
nnnnnnnnnn nnnnnnnnnn nnnnnnnnnn nnnnnnnnnn nnnnnnnnnn nnnnnnnnnn    7140
nnnnnnnnnn nnnnnnnnnn nnnnnnnnnn nnnnnnnnnn nnnnnnnnnn nnnnnnnnnn    7200
nnnnnnnnnn nnnnnnnnnn nnnnnnnnnn nnnnnnnnnn nnnnnnnnnn nnnnnnnnnn    7260
nnnnnnnnnn nnnnnnnnnn nnnnnnnnnn nnnnnnnnnn nnnnnnnnnn nnnnnnnnnn    7320
nnnnnnnnnn nnnnnnnnnn nnnnnnnnnn nnnnnnnnnn nnnnnnnnnn nnnnnnnnnn    7380
nnnnnnnnnn nnnnnnnnnn nnnnnnnnnn nnnnnnnnnn nnnnnnnnnn nnnnnnnnnn    7440
nnnnnnnnnn nnnnnnnnnn nnnnnnnnnn nnnnnnnnnn nnnnnnnnnn nnnnnnnnnn    7500
nnnnnnnnnn nnnnnnnnnn nnnnnnnnnn nnnnnnnnnn nnnnnnnnnn nnnnnnnnnn    7560
nnnnnnngaa ttcgagctcg gtacccgggg atcgacataa ccgataggtc ctgcattgat    7620
ggactgaaag gtttcgacgg cggttgtgtg ggttttgctt gcccatctgg cggcatgaat    7680
agtgtcattc atgacgatcc agttcgatat tcaacagacc gtctttgtaa tcggcaccga    7740
caattttgat caataaagcg tttgacctga tgcatgaggg taaatccatt cgttcggttg    7800
ttcttttctg attacctgtc ctgttaacct gtggatatag aaggtcggtt caatgagtag    7860
tattctgacg catctgacaa ttggttccaa tgacctgaag aaggcgcgca tcttttatga    7920
tgctgttttg gaaccgttgg gtatcaaact tattcgcgag gtcgaaggac agcgttttgc    7980
ctatggtaaa gacggcgaag aaggacgcat catcattgta aagcctatta atggtgaagc    8040
cgctaccgct ggaaatggta tcactatcgg tttggcagcg ccttctgatg aagctgtcga    8100
```

-continued

```
tgcttttat  aaagcaggct  tggctaatgg  cggtaaggat  gccggagaac  cggggcctcg   8160
tccggctgct  aataattctc  ggggtgccta  tttatatgac  cctgaaggca  ataaaatctg   8220
cgctttcaat  tttaaataag  atttctttgg  tgcagggtta  ttcaaaatag  ccctgcattt   8280
tcagtattat  agcggccatt  atggcttttg  ccttgataaa  aaatttatca  gggctgtttt   8340
tcgtgatgaa  tattttgat  ttttcaagaa  aagcctgata  tcttccaaca  tctttctttg   8400
tatataaatg  gagcgagcta  tggcgcgcgt  aactgtcgaa  gactgtatcg  ataaagttca   8460
taatcgtttc  gatttgatcc  tctagagtca  acctgcttgt  tactcgtgat  cccattcaca   8520
agggcgaatt  aattcgccct  tctgttccgt  taccaacact  tgagccggag  gcataatggg   8580
aaagccaatg  tggcgttgtt  gggcgttgat  gctgatggtg  tggttcagtg  cgtcggctac   8640
ggcggcgaac  ggctgggaaa  tctataaaag  ccgtttcatg  accacggacg  ggcgcattca   8700
ggataccggc  aataagaatg  tcagccacac  cgaaggtcag  ggattcgcca  tgctgatggc   8760
ggtgcattac  gatgaccgca  tcgcgttcga  taacctgtgg  aactggacgc  aaagccacct   8820
gcggaacacg  accagcggct  tgttctactg  gcgttacgat  ccgtcggcgg  ccaatccggt   8880
ggtggataag  aacaacgcct  cggatggcga  tgtgctgatt  gcctgggcgt  tgttaaaagc   8940
gggaaataag  tggcaggaca  accgttacct  gcaggcgtcg  gacagcatcc  agaaagcgat   9000
catcgccagc  aatatcattc  agtttgcggg  ccgcaccgtg  atgttgcccg  cgcctatgg   9060
tttcaacaag  aacagctatg  tgatccttaa  cccgtcgtat  ttcctgttcc  cggcctggcg   9120
cgactttgct  aaccgcagcc  atcttcaggt  gtggcggcaa  ctgattgacg  acagcctgtc   9180
attggtcgga  gaaatgcgtt  tcggtcaggt  cgggctgccg  acggactggg  cggcgctgaa   9240
cgcggatggc  tcgatggcgc  cggcgacggc  ctggccgtcg  cgtttcagtt  acgacgccat   9300
tcgtatcccg  ctgtatttgt  actggtatga  cgccaaaacc  acggcgctgg  tgccgttcca   9360
gctgtactgg  cgtaactatc  cccgcctgac  gacgccggcc  tgggttgatg  tgctgagcag   9420
taacaccgcg  acttacaata  tgcagggcgg  tttgctggcg  gtgcgcgacc  tgacgatggg   9480
caacctcgac  gggctcagcg  atctgccagg  cgcatcggaa  gattactact  cgtcgagcct   9540
gcgcctgctg  gtgatgttgg  cgcgcggtaa  ataaccttat  tcttgcggta  cacatggcga   9600
ggacgatgtc  cttgccattt  tccccacttt  tatccctctg  aatggcgtgt  ttttcacgct   9660
ttgttaacct  gcttgttact  cgtgatccca  ttcacaaggg  cgaattgacc  tgcaggcatg   9720
caagcttggc  gtaatcatgg  tcatagctgt  ttcctgtgtg  aaattgttat  ccgctcacaa   9780
ttccacacaa  catacgagcc  ggaagcataa  agtgtaaagc  ctggggtgcc  taatgagtga   9840
gctaactcac  attaattgcg  ttgcgctcac  tgcccgcttt  ccagtcggga  aacctgtcgt   9900
gccagctgca  ttaatgaatc  ggccaacgcg  cggggagagg  cggtttgcgt  attgggcgct   9960
cttccgctgg  cgcgccaggt  cgactctaga  ggatccccgg  ggaagatctt  ccggaagatc  10020
ttcccgagct  cgaattaatt  ccgcgatgaa  ttgatcccgg  aagttcctat  tctctagaaa  10080
gtataggaac  tcgaattggt  cgacaagcta  gcttgcatgc  aagcttgtat  tctatagtgt  10140
cacctaaatc  gtatgtgtat  gatacataag  gttatgtatt  aattgtagcc  gcgttctaac  10200
gacaatatgt  acaagcctaa  ttgtgtagca  tctggcttac  tgaagcagac  cctatcatct  10260
ctctcgtaaa  ctgccgtcag  agtcggtttg  gttggacgaa  ccttctgagt  ttctggtaac  10320
gccgttccgc  accccggaaa  tggtcagcga  accaatcagc  agggtcatcg  ctagcccatg  10380
gctaattctg  tcagccgtta  agtgttcctg  tgtcactgaa  aattgctttg  agaggctcta  10440
```

```
agggcttctc agtgcgttac atccctggct tgttgtccac aaccgttaaa ccttaaaagc    10500
tttaaaagcc ttatatattc ttttttttct tataaaactt aaaaccttag aggctattta    10560
agttgctgat ttatattaat tttattgttc aaacatgaga gcttagtacg tgaaacatga    10620
gagcttagta cgttagccat gagagcttag tacgttagcc atgagggttt agttcgttaa    10680
acatgagagc ttagtacgtt aaacatgaga gcttagtacg tgaaacatga gagcttagta    10740
cgtactatca acaggttgaa ctgcggatct tgcggccgca aaaattaaaa atgaagtttt    10800
gacggtatcg aacccagag tcccgctcag aagaactcgt caagaaggcg atagaaggcg    10860
atgcgctgcg aatcgggagc ggcgataccg taaagcacga ggaagcggtc agcccattcg    10920
ccgccaagct cttcagcaat atcacgggta gccaacgcta tgtcctgata gcggtccgcc    10980
acacccagcc ggccacagtc gatgaatcca gaaaagcggc catttccac catgatattc    11040 ggcaagcagg catcgccatg ggtcacgacg agatcctcgc cgtcgggcat ccgcgccttg    11100
agcctggcga acagttcggc tggcgcgagc ccctgatgct cttcgtccag atcatcctga    11160
tcgacaagac cggcttccat ccgagtacgt gctcgctcga tgcgatgttt cgcttggtgg    11220
tcgaatgggc aggtagccgg atcaagcgta tgcagccgcc gcattgcatc agccatgatg    11280
gatactttct cggcaggagc aaggtgagat gacaggagat cctgccccgg cacttcgccc    11340
aatagcagcc agtcccttcc cgcttcagtg acaacgtcga gcacagctgc gcaaggaacg    11400
cccgtcgtgg ccagccacga tagccgcgct gcctcgtctt ggagttcatt cagggcaccg    11460
gacaggtcgg tcttgacaaa aagaaccggg cgcccctgcg ctgacagccg gaacacggcg    11520
gcatcagagc agccgattgt ctgttgtgcc cagtcatagc cgaatagcct ctccacccaa    11580
gcggccggag aacctgcgtg caatccatct tgttcaatca tgcgaaacga tcctcatcct    11640
gtctcttgat ccactagatt attgaagcat ttatcagggt tattgtctca tgagcggata    11700
catatttgaa tgtatttaga aaataaaca aataggggtt ccgcgcacat ttccccgaaa    11760
agtgccacct gc                                                         11772

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
atatttttga tttttcaaga aaagcctgat atcttccaac atctt                  45

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gatttgatcc tctagagtca acctgcttgt tactcgtgat cccat                  45

<210> SEQ ID NO 20
<211> LENGTH: 44
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 20
gagtcaacct gcttgttact cgtgatccca ttcacaaggg cgaa         44

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttactcgtga tcccattcac aagggcgaat taattcgccc tt           42

<210> SEQ ID NO 22
<211> LENGTH: 427
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 22

Met Pro Leu Ser Tyr Ser Asp Asn His Pro Val Ile Asp Ser Gln Lys
1               5                   10                  15

His Ala Pro Arg Lys Lys Leu Phe Leu Ser Cys Ala Cys Leu Gly Leu
            20                  25                  30

Ser Leu Ala Cys Leu Ser Ser Asn Ala Trp Ala Ser Val Glu Pro Leu
        35                  40                  45

Ser Val Ser Gly Asn Lys Ile Tyr Ala Gly Glu Lys Ala Lys Ser Phe
    50                  55                  60

Ala Gly Asn Ser Leu Phe Trp Ser Asn Gly Trp Gly Glu Lys
65                  70                  75                  80

Phe Tyr Thr Ala Asp Thr Val Ala Ser Leu Lys Lys Asp Trp Lys Ser
                85                  90                  95

Ser Ile Val Arg Ala Ala Met Gly Val Gln Glu Ser Gly Gly Tyr Leu
            100                 105                 110

Gln Asp Pro Ala Gly Asn Lys Ala Lys Val Glu Arg Val Val Asp Ala
        115                 120                 125

Ala Ile Ala Asn Asp Met Tyr Val Ile Ile Asp Trp His Ser His Ser
    130                 135                 140

Ala Glu Asn Asn Arg Ser Glu Ala Ile Arg Phe Phe Gln Glu Met Ala
145                 150                 155                 160

Arg Lys Tyr Gly Asn Lys Pro Asn Val Ile Tyr Glu Ile Tyr Asn Glu
                165                 170                 175

Pro Leu Gln Val Ser Trp Ser Asn Thr Ile Lys Pro Tyr Ala Glu Ala
            180                 185                 190

Val Ile Ser Ala Ile Arg Ala Ile Asp Pro Asp Asn Leu Ile Ile Val
        195                 200                 205

Gly Thr Pro Ser Trp Ser Gln Asn Val Asp Glu Ala Ser Arg Asp Pro
    210                 215                 220

Ile Asn Ala Lys Asn Ile Ala Tyr Thr Leu His Phe Tyr Ala Gly Thr
225                 230                 235                 240

His Gly Glu Ser Leu Arg Thr Lys Ala Arg Gln Ala Leu Asn Asn Gly
                245                 250                 255

Ile Ala Leu Phe Val Thr Glu Trp Gly Ala Val Asn Ala Asp Gly Asn

```
                       260                 265                 270
Gly Gly Val Asn Gln Thr Asp Thr Asp Ala Trp Val Thr Phe Met Arg
            275                 280                 285

Asp Asn Asn Ile Ser Asn Ala Asn Trp Ala Leu Asn Asp Lys Ser Glu
    290                 295                 300

Gly Ala Ser Thr Tyr Tyr Pro Asp Ser Lys Asn Leu Thr Glu Ser Gly
305                 310                 315                 320

Lys Ile Val Lys Ser Ile Ile Gln Ser Trp Pro Tyr Lys Ala Gly Ser
                325                 330                 335

Ala Ala Ser Thr Thr Thr Asp Gln Ser Thr Asp Thr Thr Met Ala Pro
            340                 345                 350

Pro Leu Thr Asn Arg Pro Gln Pro Thr His Arg Gln Thr Ala Asp Cys
            355                 360                 365

Cys Asn Ala Asn Val Tyr Pro Asn Trp Val Ser Lys Asp Trp Ala Gly
    370                 375                 380

Arg Gln Arg Leu Ile Thr Lys Gln Ala Asn Arg Ser Ser Thr Lys Gly
385                 390                 395                 400

Thr Cys Ile Pro Gln Thr Gly Thr Leu His Pro Phe Arg Ala Ala Ile
                405                 410                 415

Pro Pro Gly His Arg Leu Val Ala Val Thr Asn
            420                 425

<210> SEQ ID NO 23
<211> LENGTH: 286
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 23

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190
```

```
Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
        210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
            245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```

<210> SEQ ID NO 24
<211> LENGTH: 396
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 24

```
Met Lys Ser Asn Asn Ala Leu Ile Val Ile Leu Gly Thr Val Thr Leu
1               5                   10                  15

Asp Ala Val Gly Ile Gly Leu Val Met Pro Val Leu Pro Gly Leu Leu
            20                  25                  30

Arg Asp Ile Val His Ser Asp Ser Ile Ala Ser His Tyr Gly Val Leu
        35                  40                  45

Leu Ala Leu Tyr Ala Leu Met Gln Phe Leu Cys Ala Pro Val Leu Gly
    50                  55                  60

Ala Leu Ser Asp Arg Phe Gly Arg Arg Pro Val Leu Leu Ala Ser Leu
65                  70                  75                  80

Leu Gly Ala Thr Ile Asp Tyr Ala Ile Met Ala Thr Thr Pro Val Leu
            85                  90                  95

Trp Ile Leu Tyr Ala Gly Arg Ile Val Ala Gly Ile Thr Gly Ala Thr
        100                 105                 110

Gly Ala Val Ala Gly Ala Tyr Ile Ala Asp Ile Thr Asp Gly Glu Asp
        115                 120                 125

Arg Ala Arg His Phe Gly Leu Met Ser Ala Cys Phe Gly Val Gly Met
        130                 135                 140

Val Ala Gly Pro Val Ala Gly Gly Leu Leu Gly Ala Ile Ser Leu His
145                 150                 155                 160

Ala Pro Phe Leu Ala Ala Ala Val Leu Asn Gly Leu Asn Leu Leu Leu
            165                 170                 175

Gly Cys Phe Leu Met Gln Glu Ser His Lys Gly Glu Arg Arg Pro Met
        180                 185                 190

Pro Leu Arg Ala Phe Asn Pro Val Ser Ser Phe Arg Trp Ala Arg Gly
        195                 200                 205

Met Thr Ile Val Ala Ala Leu Met Thr Val Phe Phe Ile Met Gln Leu
        210                 215                 220

Val Gly Gln Val Pro Ala Ala Leu Trp Val Ile Phe Gly Glu Asp Arg
225                 230                 235                 240

Phe Arg Trp Ser Ala Thr Met Ile Gly Leu Ser Leu Ala Val Phe Gly
            245                 250                 255

Ile Leu His Ala Leu Ala Gln Ala Phe Val Thr Gly Pro Ala Thr Lys
        260                 265                 270
```

-continued

```
Arg Phe Gly Glu Lys Gln Ala Ile Ile Ala Gly Met Ala Ala Asp Ala
            275                 280                 285

Leu Gly Tyr Val Leu Leu Ala Phe Ala Thr Arg Gly Trp Met Ala Phe
        290                 295                 300

Pro Ile Met Ile Leu Leu Ala Ser Gly Gly Ile Gly Met Pro Ala Leu
305                 310                 315                 320

Gln Ala Met Leu Ser Arg Gln Val Asp Asp His Gln Gly Gln Leu
                325                 330                 335

Gln Gly Ser Leu Ala Ala Leu Thr Ser Leu Thr Ser Ile Thr Gly Pro
            340                 345                 350

Leu Ile Val Thr Ala Ile Tyr Ala Ala Ser Ala Ser Thr Trp Asn Gly
        355                 360                 365

Leu Ala Trp Ile Val Gly Ala Ala Leu Tyr Leu Val Cys Leu Pro Ala
        370                 375                 380

Leu Arg Arg Gly Ala Trp Ser Arg Ala Thr Ser Thr
385                 390                 395
```

US 7,026,152 B2

METHODS AND COMPOSITIONS FOR SIMULTANEOUS SACCHARIFICATION AND FERMENTATION

RELATED INFORMATION

This application claims priority to U.S. provisional application No. 60/214,137, entitled "Synergistic Hydrolysis of Carboxymethyl Cellulose and Acid Swollen Cellulose by Two Endoglucanases (EGZ and EGY)," filed Jun. 26, 2000, and U.S. provisional application No. 60/219,913, entitled "Methods and Compositions for Simultaneous Saccharification and Fermentation," filed Jul. 21, 2000, both of which are incorporated herein in their entirety by this reference. The contents of all patents, patent applications, and references cited throughout this specification are hereby incorporated by reference in their entireties.

GOVERNMENT SPONSORED RESEARCH

This work was supported, in part, by grants from the U.S. Department of Agriculture, National Research Initiative (98-35504-6177 and 98-35505-6976), the U.S. Department of Energy, Office of Basic Energy Science (FG02-96ER20222), and the Florida Agricultural Experiment Station, University of Florida.

BACKGROUND OF THE INVENTION

Many environmental and societal benefits would result from the replacement of petroleum-based automotive fuels with renewable fuels obtained from plant materials (Lynd et al., (1991) *Science* 251:1318–1323; Olson et al., (1996) *Enzyme Microb. Technol.* 18:1–17; Wyman et al., (1995) *Amer. Chem. Soc. Symp.* 618:272–290). Each year, the United States burns over 120 billion gallons of automotive fuel, roughly equivalent to the total amount of imported petroleum. The development of ethanol as a renewable alternative fuel has the potential to eliminate United States dependence on imported oil, improve the environment, and provide new employment (Sheehan, (1994) ACS Symposium Series No. 566, ACS Press, pp 1–53).

In theory, the solution to the problem of imported oil for automotive fuel appears quite simple. Rather than using petroleum, a finite resource, ethanol, a renewable resource, can be produced efficiently by the fermentation of plant material. Indeed, Brazil has demonstrated the feasibility of producing ethanol and the use of ethanol as a primary automotive fuel for more than 20 years. Similarly, the United States produces over 1.2 billion gallons of fuel ethanol each year. Currently, fuel ethanol is produced from corn starch or cane syrup utilizing either *Saccharomyces cerevisiae* or *Zymomonas mobilis* (*Z. mobilis*). However, neither of these sugar sources can supply the volumes needed to realize a replacement of petroleum-based automotive fuels. In addition, both cane sugar and corn starch are relatively expensive starting materials, which have competing uses as food products.

Moreover, these sugar substrates represent only a fraction of the total carbohydrates in plants. Indeed, the majority of the carbohydrates in plants are in the form of lignocellulose, a complex structural polymer containing cellulose, hemicellulose, pectin, and lignin. Lignocellulose is found in, for example, the stems, leaves, hulls, husks, and cobs of plants. Hydrolysis of these polymers releases a mixture of neutral sugars including glucose, xylose, mannose, galactose, and arabinose. No known natural organism can rapidly and efficiently metabolize all of these sugars into ethanol.

Nonetheless, in an effort to exploit this substrate source, the Gulf Oil Company developed a method for the production of ethanol from cellulose using a yeast-based process termed simultaneous saccharification and fermentation (SSF) (Gauss et al. (1976) U.S. Pat. No. 3,990,944). Fungal cellulase preparations and yeasts were added to a slurry of the cellulosic substrate in a single vessel. Ethanol was produced concurrently during cellulose hydrolysis. However, Gulf's SSF process has some shortcomings. For example, fungal cellulases have been considered, thus far, to be too expensive for use in large scale bioethanol processes (Himmel et al., (1997) Amer. Chem. Soc. pp. 2–45; Ingram et al., (1987) *Appl. Environ. Microbiol.* 53:2420–2425; Okamoto et al., (1994) *Appl. Microbiol. Biotechnol.* 42:563–568; Philippidis, G., (1994) Amer. Chem. Soc. pp. 188–217; Saito et al., (1990) *J. Ferment. Bioeng.* 69:282–286; Sheehan, J., (1994) Amer. Chem. Soc. pp 1–52; Su et al., (1993) *Biotechnol. Lett.* 15:979–984).

SUMMARY OF THE INVENTION

The development of inexpensive enzymatic methods for cellulose hydrolysis has great potential for improving the efficiency of substrate utilization and the economics of the saccharification and fermentation process. Accordingly, developing enzymes and, preferably, biocatalysts that produce such enzymes which can be used for the efficient depolymerization of a complex sugars and subsequent rapid fermentation of the sugar into alcohol, would be of great benefit.

Certain microbes, such as *Erwinia chrysanthemi*, produce a number of hydrolase and lyase enzymes, which are very effective in the degrading of plant tissues containing complex sugars. In particular, this organism produces two different endoglucanase activities (comprising EGY and EGZ) which have been discovered to function, when used in particular amounts, as highly effective enzyme compositions for degrading complex sugars. These enzymes may be used as crude extracts having a desired mixture of endoglucanase activity or, preferably, may be used as purified compositions.

Moreover, a biocatalyst, preferably a recombinant bacterium, more preferably a ethanologenic bacterium, can be engineered to express one or more of these enzymatic activities in particular amounts sufficient for degrading complex sugars. Such a biocatalyst is suitable for the efficient degradation of complex sugars and subsequent fermentation into alcohol by a process known as simultaneous saccharification and fermentation (SSF). An advantage of the above endoglucanase compositions or biocatalysts is that the need for additional fungal cellulases for degrading the complex sugars is reduced or eliminated.

The present invention provides endoglucanase activities for carrying out the degrading of a complex sugar and more preferably, the use of endoglucanase activities in particular ratios for optimal degrading of a complex sugar.

In addition, the invention provides recombinant host cells engineered for optimal expression and secretion of endoglucanase activities suitable for degrading complex sugars. Specifically exemplified are recombinant enteric bacteria, *Escherichia* and *Klebsiella*, which express an endoglucanase under the transcriptional control of a surrogate promoter for optimal expression. In addition, also exemplified is a recombinant enteric bacterium that expresses two different endoglucanases celY and celZ, where each is under the transcriptional control of a surrogate promoter for optimal expression in a particular ratio.

The invention provides for the further modification of these hosts to include a secretory protein/s that allow for the increased production and/or secretion of the endoglucanases from the cell. In a preferred embodiment, the invention provides for the further modification of these hosts to include exogenous ethanologenic genes derived from an efficient ethanol producer, such as *Zymomonas mobilis*.

Accordingly, these hosts are capable of expressing high levels of proteins that may be used alone or in combination with other enzymes or recombinant hosts for the efficient production of alcohol from complex sugars.

More particularly, in a first aspect, the invention provides a composition for degrading an oligosaccharide containing, a first endoglucanase having a first degrading activity, and a second endoglucanase having a second degrading activity, where the first and second degrading activities are present in a ratio such that the degrading of the oligosaccharide by the first and second endoglucanases is synergized.

In a second aspect, the invention provides a method for degrading an oligosaccharide comprising, contacting an oligosaccharide with a first endoglucanase having a first degrading activity and a second endoglucanase having a second degrading activity, where the first and second degrading activities are present in a ratio such that the degrading of the oligosaccharide by the first and second endoglucanases is synergized.

In one embodiment of the above aspects, the contacting of the oligosaccharide with the first endoglucanase and the second endoglucanase is performed in any order or concurrently.

In one embodiment of the above aspects, the first endoglucanase or the second endoglucanase, or both the first and the second endoglucanases, are derived from a cell extract. The cell extract is derived from a bacterial cell, e.g., a bacterial cell that has been recombinantly engineered to express the first endoglucanase or the second endoglucanase, or both the first and the second endoglucanases. In a related embodiment, the bacterial cell is selected from the family Enterobacteriaceae, and preferably, is either *Escherichia* or *Klebsiella*, and more preferably contains a first endoglucanase that is encoded by celZ and a second endoglucanase that is encoded by celY, and where celZ and celY are derived from *Erwinia*.

In another embodiment of the above aspects, the first endoglucanase is EGZ and the second endoglucanase is EGY, preferably in a ratio ranging from about 1:1 to, more preferably, about 9:1 to about 19:1.

In still another embodiment of the above aspects, the first endoglucanase or the second endoglucanase, or both the first and the second endoglucanase, are purified.

In even another embodiment of the above aspects, the degrading of an oligosaccharide is synergized by a factor ranging from about 1.1 to about 2.0, and preferably by about 1.8.

In yet another embodiment of the above aspects, the composition contains an additional enzyme, e.g., an endoglucanase, exoglucanase, cellobiohydrolase, β-glucosidase, endo-1,4-β-xylanase, α-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase, or a combination thereof.

In a related embodiment of the above aspects, the additional enzyme is a glucanase derived from a fungus, preferably *T. longibranchiatum*.

In another related embodiment of the above aspects, the additional enzyme is an ethanologenic enzyme, preferably an ethanologenic enzyme such as pyruvate decarboxylase or alcohol dehydrogenase.

In another embodiment of the above aspects, the first endoglucanase and the second endoglucanase are packaged separately.

In another embodiment of the above aspects, the composition is used for simultaneous saccharification and fermentation.

In still another embodiment of the above aspects, the oligosaccharide is a cellooligosaccharide, lignocellulose, hemicellulose, cellulose, pectin, or any combination thereof.

In still another embodiment of the above aspects, the composition or method is, respectively, used or conducted in an aqueous solution.

In a third aspect, the invention provides a recombinant host cell suitable for degrading an oligosaccharide containing a first heterologous polynucleotide segment encoding a first endoglucanase having a first degrading activity, where the segment is under the transcriptional control of a surrogate promoter; and a second heterologous polynucleotide segment encoding a second endoglucanase having a second degrading activity, where the segment is under the transcriptional control of a surrogate promoter, and where the first endoglucanase and the second endoglucanase are expressed so that the first and the second degrading activities are present in a ratio such that the degrading of the oligosaccharide by the first and second endoglucanases is synergized.

In one embodiment, the first endoglucanase or the second endoglucanase, or both the first and the second endoglucanases are secreted. In a related embodiment, the first endoglucanase or the second endoglucanase, or both the first and the second endoglucanases, are derived from a cell extract. The cell extract is derived from a bacterial cell, e.g., a bacterial cell that has been recombinantly engineered to express the first endoglucanase or the second endoglucanase, or both the first and the second endoglucanases. In a related embodiment, the bacterial cell is selected from the family Enterobacteriaceae, and preferably, is either *Escherichia* or *Klebsiella*, and more preferably *E. coli* B, *E. coli* DH5α, or *Klebsiella oxytoca*.

In yet another embodiment, the recombinant host expresses an additional enzyme, e.g., an endoglucanase, exoglucanase, cellobiohydrolase, β-glucosidase, endo-1,4-β-xylanase, α-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase, or a combination thereof.

In one embodiment, the first endoglucanase is encoded by celZ and the second endoglucanase is encoded by celY, and where celZ and celY are derived from *Erwinia*.

In a related embodiment of the above aspects, the additional enzyme is a glucanase derived from a fungus, preferably *T. longibranchiatum*.

In another related embodiment, the first endoglucanase is EGZ and the second endoglucanase is EGY.

In another related embodiment, the additional enzyme is a secretory enzyme, preferably a pul or out gene product.

In another related embodiment of the above aspects, the host cell is ethanologenic, e.g., *E. coli* KO4 (ATCC 55123), *E. coli* KO11 (ATCC 55124), *E. coli* KO12 (ATCC 55125) and *E. coli* LY01 (ATCC 11303) *K. oxytoca* M5A1, and *K. axytoca* P2 (ATCC 55307).

In a fourth aspect, the invention provides a method for enhancing the degradation of an oligosaccharide by contacting an oligosaccharide with a host cell containing, a first heterologous polynucleotide segment encoding a first endoglucanase having a first degrading activity, where the segment is under the transcriptional control of a surrogate promoter; and a second heterologous polynucleotide segment containing a sequence encoding a second endoglucanase having a second degrading activity, where the segment is under the transcriptional control of a surrogate promoter. The method further provides that the first endoglucanase and the second endoglucanase are expressed so that the first and the second degrading activities are present in a ratio such that the degrading of the oligosaccharide by the first and second endoglucanases is synergized and thereby enhanced.

In one embodiment of the above aspect, the first endoglucanase or the second endoglucanase or both the first and the second endoglucanases are secreted.

In another embodiment, the host cell of the above method is ethanologenic.

In another embodiment, the method is conducted in an aqueous solution.

In even another embodiment, the method is used for simultaneous saccharification and fermentation.

In yet another embodiment, the method includes degrading an oligosaccharide selected from the group consisting of cellooligosaccharide, lignocellulose, hemicellulose, cellulose, pectin, or any combination thereof.

In a fifth aspect, the invention provides a method of making a recombinant host cell suitable for degrading an oligosaccharide by introducing into the host cell a first heterologous polynucleotide segment encoding a first endoglucanase having a first degrading activity, where the segment is under the transcriptional control of a surrogate promoter; and a second heterologous polynucleotide segment containing a sequence encoding a second endoglucanase having a second degrading activity, where the segment is under the transcriptional control of a surrogate promoter. The method further provides that the first and second endoglucanases are expressed such that the first and the second degrading activities are present in a ratio such that the degrading of the oligosaccharide by the first and second endoglucanases is synergized.

In one embodiment of the above aspect, the first endoglucanase or the second endoglucanase or both the first and second endoglucanases are secreted.

In another embodiment, the host cell is ethanologenic.

In even another embodiment, the first endoglucanase is encoded by celZ and the second endoglucanase is encoded by celY, and celZ and celY are derived from *Erwinia*.

In still another embodiment, the surrogate promoter of the first heterologous polynucleotide segment or the second heterologous polynucleotide segment or both the first and second polynucleotide segments, contains a polynucleotide fragment derived from *Zymomonas mobilis*.

In yet another embodiment, the recombinant host cell is suitable for simultaneous saccharification and fermentation, and preferably, is ethanologenic.

In a sixth aspect, the invention provides a method for making a recombinant host cell integrant by introducing into the host cell a vector containing the polynucleotide sequence of pLOI2352 (SEQ ID NO: 17) and identifying a host cell having the vector stably integrated.

In a seventh aspect, the invention provides a method for expressing a endoglucanase in a host cell by introducing into the host cell a vector containing the polynucleotide sequence of pLOI2306 (SEQ ID NO: 12) and identifying a host cell expressing the endoglucanase.

In an eighth aspect, the invention provides a method for producing ethanol from an oligosaccharide source by contacting the oligosaccharide source with a ethanologenic host cell containing a first heterologous polynucleotide segment encoding a first endoglucanase having a first degrading activity, where the segment is under the transcriptional control of a surrogate promoter; and a second heterologous polynucleotide segment encoding a second endoglucanase having a second degrading activity, where the segment is under the transcriptional control of a surrogate promoter. The method further provides that the first and second endoglucanases are expressed so that the first and the second degrading activities are present in a ratio such that the degrading of the oligosaccharide by the first and second endoglucanases is synergized resulting in a degraded oligosaccharide that is fermented into ethanol.

In one embodiment, the first endoglucanase is encoded by celZ and the second endoglucanase is encoded by celY gene, and celZ and celY are derived from *Erwinia*.

In another embodiment, the host cell further contains a heterologous polynucleotide segment encoding at least one pul gene or out gene.

In even another embodiment, the host cell is selected from the family Enterobacteriaceae, preferably *Escherichia* or *Klebsiella*, more preferably *E. coli* KO4 (ATCC 55123), *E. coli* KO11 (ATCC 55124), *E. coli* KO12 (ATCC 55125), LY01 (ATCC 11303), *K. oxytoca* M5A1, or *K. oxytoca* P2 (ATCC 55307).

In another embodiment, the method is conducted in an aqueous solution.

In still another embodiment, the oligosaccharide is selected from the group consisting of cellooligosaccharide, lignocellulose, hemicellulose, cellulose, pectin, and any combination thereof.

In another embodiment, the heterologous polynucleotide segment is, or derived from, pLOI2352 (SEQ ID NO: 17).

In yet another embodiment, the first endoglucanase is EGZ and the second endoglucanase is EGY.

In another embodiment, the surrogate promoter of the first polynucleotide segment or the second polynucleotide segment, or both the first and the second polynucleotide segments contains a polynucleotide fragment derived from *Zymomonas mobilis*.

In ninth aspect, the invention provides a vector containing the polynucleotide sequence of a plasmid, or fragment thereof, of pLOI2311, pLOI1620, pLOI2316, pLOI2317, pLOI2318, pLOI2319, pLOI2320, pLOI2323, pLOI2342, pLOI2348, pLOI2349, pLOI2350, pLOI2352, pLOI2353, pLOI2354, pLOI2355, pLOI2356, pLOI2357, pLOI2358, or pLOI2359.

In a tenth aspect, the invention provides a host cell containing a vector having the polynucleotide sequence of a plasmid, of fragment thereof, of pLOI2311, pLOI1620, pLOI2316, pLOI2317, pLOI2318, pLOI2319, pLOI2320, pLOI2323, pLOI2342, pLOI2348, pLOI2349, pLOI2350, pLOI2352, pLOI2353, pLOI2354, pLOI2355, pLOI2356, pLOI2357, pLOI2358, or pLOI2359.

In one embodiment, the host is *Klebsiella oxytoca* strain P2 (pCPP2006), *Klebsiella oxytoca* strain SZ6 (pCPP2006), *Klebsiella oxytoca* strain SZ21 (pCPP2006), or *Klebsiella oxytoca* strain SZ22 (pCPP2006).

In an eleventh aspect, the invention provides a method for degrading an oligosaccharide by obtaining a first endoglucanase having a first degrading activity, obtaining a second endoglucanase having a second degrading activity, and contacting an oligosaccharide with the first and second endoglucanases, where the first and second degrading activities are present in a ratio such that the degrading of the oligosaccharide by the first and second endoglucanases is synergized.

In a twelfth aspect, the invention provides a method for enhancing the degrading of an oligosaccharide by contacting an oligosaccharide with a first endoglucanase having a first degrading activity and a second endoglucanase having a second degrading activity, where the first and second degrading activities are present in a ratio such that the degrading of the oligosaccharide by the first and second endoglucanases is synergized and thereby enhanced.

In a related aspect, the invention provides a method for degrading, and/or for enhancing the degrading of, an oligosaccharide by contacting an oligosaccharide with a first endoglucanase having a first degrading activity and a second endoglucanase having a second degrading activity, where the first and second degrading activities are present in a ratio such that the degrading of the oligosaccharide by the first and second endoglucanases results in a change in viscosity, preferably, a reduction in viscosity, more preferably by an amount of at least, e.g., 5 centopoise, 10 centopoise, 20 centopoise, 50 centopoise, 100 centopoise, 500 centopoise, or 1000 centopoise or more, or within a range thereof.

In a preferred embodiment, the oligosaccharide is cellulose, e.g., amorphous cellulose or crystalline cellulose and may be from a source such as, e.g., paper, pulp, or plant fiber.

In a thirteenth aspect, the invention provides a recombinant host cell suitable for degrading an oligosaccharide containing a first heterologous polynucleotide segment encoding a first endoglucanase; and a second heterologous polynucleotide segment encoding a second endoglucanase.

In a related aspect, the host cell is suitable for reducing the viscosity of an oligosaccharide by comprising a first heterologous polynucleotide segment encoding a first endoglucanase; and a second heterologous polynucleotide segment encoding a second endoglucanase.

In one embodiment, the first heterologous polynucleotide segment is under the transcriptional control of a surrogate promoter, and the second heterologous polynucleotide segment is under the transcriptional control of a surrogate promoter.

In another embodiment, the cell is a bacterial cell, preferably selected from the family Enterobacteriaceae, more preferably from the genus *Escherichia* or *Klebsiella*.

In another embodiment, the first endoglucanase is encoded by celZ and the second endoglucanase is encoded by celY, and celZ and celY are derived from *Erwinia*.

In another embodiment, the first endoglucanase is EGZ and said second endoglucanase is EGY.

In a fourteenth aspect, the invention provides a recombinant host strain of *Klebsiella axytoca* strain P2 (pCPP2006) represented by a deposit with the American Type Culture Collection designated as deposit number ATCC PTA-3468.

In a fifteenth aspect, the invention provides a recombinant host strain of *Klebsiella axytoca* strain SZ6 (pCPP2006) represented by a deposit with the American Type Culture Collection designated as deposit number ATCC PTA-3464.

In a sixteenth aspect, the invention provides a recombinant host strain of *Klebsiella axytoca* strain SZ21 (pCPP2006) represented by a deposit with the American Type Culture Collection designated as deposit number ATCC PTA3465.

In a s venteenth aspect, the invention provides a recombinant host strain of *Klebsiella oxytoca* strain SZ22 (pCPP2006) represented by a deposit with the American Type Culture Collection designated as deposit number ATCC PTA-3467.

In a eighteenth aspect, the invention provides a recombinant cell containing a first heterologous polynucleotide segment encoding a first endoglucanase; and a second heterologous polynucleotide segment encoding a second endoglucanase, where the first polynucleotide segment encoding a first endoglucanase or the second polynucleotide segment encoding a second endoglucanase, or both are sufficiently homologous in an amino acid alignment to either the gene product of celY or celZ from *Erwinia* as to share the functional activity of being capable of degrading a polysaccharide.

In nineteenth aspect, the invention provides an extract or composition derived from a host cell of the invention, e.g., a secreted polypeptide, a lysate or broth, or a pure, semi-pure, or unpurified enzymatic extract or polypeptide which is suitable for degrading and/or reducing the viscosity of a oligosaccharide when contacted thereto.

Other features and advantages of the invention will be apparent from the following detailed description and claims.

BRIEF DESCRIPTION OF THE DRAWINGS

FIG. 5 shows the partial nucleotide sequence (SEQ ID NO: 1) of the *Z. mobilis* DNA fragment in the pLOI2183 plasmid that functions as a surrogate promoter. The full sequence has been assigned GenBank Accession Number AF109242 (SEQ ID NO: 2). Indicated are two transcriptional start sites (#) -35 and -10 regions, the Shine-Delgarno site (bold), partial vector and celZ sequence (lowercase), and the celZ start codon (atg indicated in bold).

FIG. 14 is a depiction of transcriptional initiation sites and putative promoter regions for the celY promoter in DH5α (pLOI12323). Transcriptional starts for celY were identified by primer extension analysis. Four promoters (SEQ ID NOS 18–21, respectively in order of appearance) were identified. Upstream sequences of these promoters with similarity to E. coli -35 and -10 regions are marked with underlines. RNA start sites are bolded. Putative promoters are numbered in parenthesis adjacent to the start site in descending order from the strongest. Differences in intensities were small, within 2-fold.

DETAILED DESCRIPTION OF THE INVENTION

Figure 1:
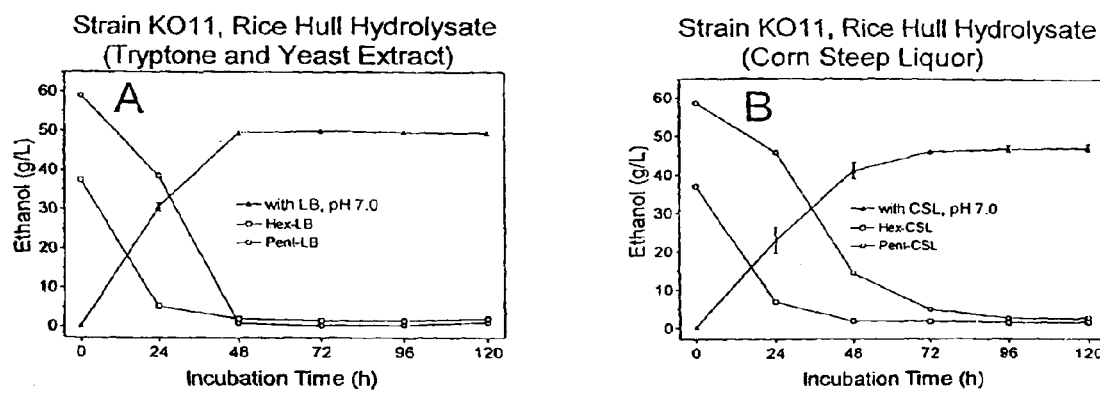
FIG. 1 shows fermentation rates for the ethanologenic recombinant host *E. coli* KO11 using rice hull substrates pretreated with dilute acid and supplemented with two different media.

In order for the full scope of the invention to be clearly understood, the following definitions are provided.

I. Definitions

As used herein the term "recombinant host" is intended to include a cell suitable for genetic manipulation, e.g., which can incorporate heterologous polynucleotide sequences, e.g., which can be transfected. The cell can be a microorganism or a higher eukaryotic cell. The term is intended to include progeny of the cell originally transfected. In preferred embodiments, the cell is a bacterial cell, e.g., a Gram-negative bacterial cell, and this term is intended to include all facultatively anaerobic Gram-negative cells of the family Enterobacteriaceae such as *Escherichia, Shigella, Citrobacter, Salmonella, Klebsiella, Enterobacter, Erwinia, Kluyvera, Serratia, Cedecea, Morganella, Hafnia, Edwardsiella, Providencia, Proteus,* and *Yersinia*. Particularly preferred recombinant hosts are *Escherichia coli* or *Klebsiella oxytoca* cells.

The term "ratio" is intended to include the relationship between the amounts (measured, e.g., by activity or in moles) of two enzymes in a predetermined combination where, preferably, the ratio is not naturally occurring and, more preferably, results in synergistic enzyme activity.

The terms "a first endoglucanase having a first degrading activity" and "a second endoglucanase having a second degrading activity" are intended to include, respectively, an endoglucanase with an activity that can be distinguished from another endoglucanase (e.g., a second endoglucanase) with a second activity functionally (e.g., by its activity on a particular substrate; synergism with another enzyme), by source of origin (e.g., host cell strain, including naturally occurring strains or genetically modified strains expressing a clone expressing an endoglucanase), or by biochemical properties using art recognized techniques (e.g., molecular weight determination or purification characteristics). The degrading activity, e.g., the enzymatic hydrolysis of an oligosaccharide, can also comprise a change in the viscosity of the oligosaccharide.

The terms "synergism," "synergistic activity," and "synergized" are intended to describe the interaction between distinguishable polypeptides or polypeptide activities wherein the effect of the total activity of the polypeptides taken together are greater than the sum of the effects of the individual activities. The polypeptides may be, for example, endoglucanases, exoglucanases, cellobiohydrolases, β-glucosidases, endo-1,4-β-xylanases, α-xylosidases, α-glucuronidases, α-L-arabinofuranosidases, acetylesterases, acetylxylanesterases, α-amylases, β-amylases, glucoamylases, pullulanases, β-glucanases, hemicellulases, arabinosidases, mannanases, pectin hydrolases, pectate lyases, or any combination thereof. An activity of a polypeptide includes the degradation (e.g., hydrolysis) of an oligosaccharide but may also include a change in the viscosity of the oligosaccharide. The synergized degrading of an oligosaccharide is preferably by a factor of about 1.1, 1.2, 1.3, 1.4, 1.5, 1.6, 1.7, 1.8, 1.9, or more preferably about 2.0, with a typical factor being about 1.8.

The term "heterologous polynucleotide segment" is intended to include a polynucleotide segment that encodes one or more polypeptides or portions or fragments of polypeptides. A heterologous polynucleotide segment may be derived from any source, e.g., eukaryotes, prokaryotes, virii, or synthetic polynucleotide fragments.

The terms "polysaccharase," "cellulase," or "glucanase" are used interchangeably herein and are intended to include a polypeptide capable of catalyzing the degradation or depolymerization of any linked sugar moiety, e.g., disaccharides, trisaccharides, oligosaccharides, including, complex carbohydrates, also referred to herein as complex sugars, e.g., cellooligosaccharide and lignocellulose, which comprises cellulose, hemicellulose, and pectin. The terms are intended to include cellulases such as glucanases, including preferably, endoglucanases but also including, e.g., exoglucanase, β-glucosidase, cellobiohydrolase, endo-1,4-β-xylanase, β-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase, or a combination of any of these cellulases.

The term "endoglucanase" is intended to include a cellulase which typically hydrolyses internal β1–4 glucosyl linkages in polymeric substrates and does not preferentially hydrolyze linkages located at the ends of the chain.

The term "surrogate promoter" is intended to include a polynucleotide segment that can transcriptionally control a gene-of-interest that it does not transcriptionally control in nature. In a preferred embodiment, the transcriptional control of a surrogate promoter results in an increase in expression of the gene-of-interest. In a preferred embodiment, a surrogate promoter is placed 5' to the gene-of-interest. A surrogate promoter may be used to replace the natural promoter, or may be used in addition to the natural promoter. A surrogate promoter may be endogenous with regard to the host cell in which it is used or it may be a heterologous polynucleotide sequence introduced into the host cell, e.g., exogenous with regard to the host cell in which it is used. Other promoters suitable for use in bacteria include, e.g., lacZ, T7, and SP6 (see, e.g., Ausubel et al. infra).

The terms "oligosaccharide source," "oligosaccharide," "complex cellulose," "complex carbohydrate," and "complex sugar," and "polysaccharide" are used essentially interchangeably and are intended to include any carbohydrate source comprising more than one sugar molecule. These carbohydrates may be derived from any unprocessed plant material or any processed plant material. Examples are wood, paper, pulp, plant derived fiber, or synthetic fiber comprising more than one linked carbohydrate moiety, i.e., one sugar residue. One particular oligosaccharide source is lignocellulose, which represents approximately 90% of the dry weight of most plant material and contains carbohydrates, e.g., cellulose, hemicellulose, pectin, and aromatic polymers, e.g, lignin. Cellulose makes up 30%–50% of the dry weight of lignocellulose and is a homopolymer of cellobiose (a dimer of glucose). Similarly, hemicellulose, makes up 20%–50% of the dry weight of lignocellulose and is a complex polymer containing a mixture of pentose (xylose, arabinose) and hexose (glucose, mannose, galactose) sugars which contain acetyl and glucuronyl side chains. Pectin makes up 1%–20% of the dry weight of lignocellulose and is a methylated homopolymer of glucuronic acid. Other oligosaccharide sources include carboxymethyl cellulose (CMC), amorphous cellulose (e.g., acid-swollen cellulose), and the cellooligosaccharides cellobiose, cellotriose, cellotetraose, and cellopentaose. Cellulose, e.g., amorphous cellulose may be derived from a paper or pulp source (including, e.g., fluid wastes thereof) or, e.g., agricultural byproducts, e.g., corn stalks, soybean solubles, or beet pulp. Any one or a combination of the above carbohydrate polymers are potential sources of sugars for depolymerization and subsequent bioconversion to ethanol by fermentation according to the products and methods of the present invention.

The term "gene/s" or "polynucleotide segment" is intended to include nucleic acid molecules, e.g., polynucleotides which include an open reading frame encoding a polypeptide, and can further include non-coding regulatory sequences, and introns. In addition, the terms are intended to include one or more genes that map to a functional locus, e.g., the out or pul genes of *Erwinia* and *Klebsiella*, respectively, that encode more than one gene product, e.g., a secretory polypeptide. In addition, the terms are intended to include a specific gene for a selected purpose. The gene may be endogenous to the host cell or may be recombinantly introduced into the host cell, e.g., as a plasmid maintained episomally or a plasmid (or fragment thereof) that is stably integrated into the genome. In a preferred embodiment, the gene of polynucleotide segment is involved in at least one step in the bioconversion of a carbohydrate to ethanol. Accordingly, the term is intended to include any gene encoding a polypeptide such as an alcohol dehydrogenase, a pyruvate decarboxylase, a secretory protein/s, or a polysaccharase, e.g., a glucanase, such as an endoglucanase or exoglucanase, a cellobiohydrolase, β-glucosidase, endo-1,4-β-xylanase, β-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase, or a combination thereof.

The term "simultaneous saccharification and fermentation" or "SSF" is intended to include the use of one or more recombinant hosts (or extracts thereof, including purified or unpurified extracts) for the contemporaneous degradation or depolymerization of a complex sugar and bioconversion of that sugar residue into ethanol by fermentation.

The term "transcriptional control" is intended to include the ability to modulate gene expression at the level of transcription. In a preferred embodiment, transcription, and thus gene expression, is modulated by replacing or adding a surrogate promoter near the 5' end of the coding region of a gene-of-interest thereby resulting in altered gene expression. In a most preferred embodiment, the transcriptional control of one or more gene is engineered to result in the optimal expression of such genes, e.g., in a desired ratio. The term also includes inducible transcriptional control as recognized in the art.

The term "expression" is intended to include the expression of a gene at least at the level of mRNA production.

The term "expression product" is intended to include the resultant product of an expressed gene, e.g., a polypeptide.

The term "increased expression" is intended to include an alteration in gene expression at least at the level of increased mRNA production and preferably, at the level of polypeptide expression.

The term "increased production" is intended to include an increase in the amount of a polypeptide expressed, in the level of the enzymatic activity of the polypeptide, or a combination thereof.

The terms "activity" and "enzymatic activity" are used interchangeably and are intended to include any functional activity normally attributed to a selected polypeptide when produced under favorable conditions. The activity of an endoglucanase (e.g., EGY or EGZ) is, for example, the ability of the polypeptide to enzymatically depolymerize a complex saccharide. Typically, the activity of a selected polypeptide encompasses the total enzymatic activity associated with the produced polypeptide. The polypeptide produced by a host cell and having enzymatic activity may be located in the intracellular space of the cell, cell-associated, secreted into the extracellular milieu, or a combination thereof. Techniques for determining total activity as compared to secreted activity are described herein and are known in the art.

The term "secreted" is intended to include an increase in the secretion of a polypeptide into the periplasmic space or into the extracellular milieu, e.g., a heterologous polypeptide, preferably a polysaccharase. Typically, the polypeptide is secreted at an increased level that is in excess of the naturally-occurring amount of secretion. More preferably, the term "secreted" refers to an increase in secretion of a given polypeptide that is at least 10% and more preferably, at least about 100%, 200%, 300%, 400%, 500%, 600%, 700%, 800%, 900%, 1000%, or more, as compared to the naturally-occurring level of secretion.

The term "secretory polypeptide" is intended to include any polypeptide/s, alone or in combination with other polypeptides, that facilitate the transport of another polypeptide from the intracellular space of a cell to the extracellular milieu. In one embodiment, the secretory polypeptide/s encompass all the necessary secretory polypeptides sufficient to impart secretory activity to a Gram-negative host cell. Typically, secretory proteins are encoded in a single region or locus that may be isolated from one host cell and transferred to another host cell using genetic engineering. In a preferred embodiment, the secretory polypeptide/s are derived from any bacterial cell having secretory activity. In a more preferred embodiment, the secretory polypeptide/s are derived from a host cell having Type II secretory activity. In another more preferred embodiment, the host cell is selected from the family Enterobacteriaceae. In a most preferred embodiment, the secretory polypeptide/s are one or more gene products of the out or pul genes derived from, respectively, *Erwinia* or *Klebsiella*. Moreover, the skilled artisan will appreciate that any secretory protein/s derived from a related host that is sufficiently homologous to the out or pul gene/s described herein may also be employed (Pugsley et al., (1993) *Microbiological Reviews* 57:50–108; Lindeberg et al., (1996) *Mol. Micro.* 20:175–190; Lindeberg et al., (1992) *J. of Bacteriology* 174:7385–7397; He et al., (1991) *Proc. Natl. Acad. Sci. USA*, 88:1079–1083).

The term "derived from" is intended to include the isolation (in whole or in part) of a polynucleotide segment from an indicated source or the purification of a polypeptide from an indicated source. The term is intended to include, for example, direct cloning, PCR amplification, or artificial synthesis from, or based on, a sequence associated with the indicated polynucleotide source.

The term "ethanologenic" is intended to include the ability of a microorganism to produce ethanol from a carbohydrate as a primary fermentation product. The term includes but is not limited to naturally occurring ethanologenic organisms, organisms with naturally occurring or induced mutations, and organisms that have been genetically modified.

The term "Gram-negative bacteria" is intended to include the art recognized definition of this term. Typically, Gram-negative bacteria include, for example, the family Enterobacteriaceae which comprises, among others, the species *Escherichia* and *Klebsiella*.

The term "sufficiently homologous" is intended to include a first amino acid or nucleotide sequence which contains a sufficient or minimum number of identical or equivalent amino acid residues or nucleotides, e.g., an amino acid residue which has a similar side chain, to a second amino acid or nucleotide sequence such that the first and second amino acid or nucleotide sequences share common structural domains and/or a common functional activity. For example, amino acid or nucleotide sequences which share common structural domains have at least about 40% homology, preferably 50% homology, more preferably 60%, 70%, 80%, or 90% homology across the amino acid sequences of the domains and contain at least one, preferably two, more preferably three, and even more preferably four, five, or six structural domains, are defined herein as sufficiently homologous. Furthermore, amino acid or nucleotide sequences which share at least 40%, preferably 50%, more preferably 60%, 70%, 80%, or 90% homology and share a common functional activity are defined herein as sufficiently homologous.

In one embodiment, two polynucleotide segments, e.g., promoters, are "sufficiently homologous" if they have substantially the same regulatory effect as a result of a substantial identity in nucleotide sequence. Typically, "sufficiently homologous" sequences are at least 50%, more preferably at least 60%, 70%, 80%, or 90% identical, at least in regions known to be involved in the desired regulation. More preferably, no more than five bases differ. Most preferably, no more than five consecutive bases differ.

To determine the percent identity of two polynucleotide segments, or two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*CABIOS*, 4:11–17 (1989)) which has been incorporated into the ALIGN program (version 2.0), using a PAM120 weight residue table, a gap length penalty of 12 and a gap penalty of 4.

The polynucleotide and amino acid sequences of the present invention can further be used as a "query sequence" to perform a search against public databases to, for example, identify other family members or related sequences, e.g., promoter sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to polynucleotide molecules of the invention. BLAST protein searches can be performed with the XBLAST program, score=50, wordlength=3 to obtain amino acid sequences homologous to polypeptide molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

II. Synergism Between Endoglucanases

The present invention is based, at least in part, on the discovery that endoglucanases act synergistically in degrading complex sugars. This invention is based, also in part, on the functional integration and expression of two endoglucanases (e.g., EGY and EGZ) by an ethanologenic host cell (e.g., *K. oxytoca* P2) to effect synergistic degradation of oligosaccharides (e.g., crystalline cellulose) and increase the production of ethanol by simultaneous saccharification and fermentation (SSF).

In one embodiment, an endoglucanase is derived from *E. chrysanthemi* and is the endoglucanase EGZ, which is encoded by the celZ gene (Boyer, et al. (1987) *Eur. J. Biochem.* 162:311–316). In another embodiment, an endoglucanase is derived from *E. chrysanthemi* and is the endoglucanase EGY, which is encoded by the celY gene (Guiseppi et al., (1991) *Gene* 106:109–114). *E. chrysanthemi* EGY and EGZ are endoglucanases that have high activities in the degradation of carboxymethyl cellulose (CMC) and belong to, respectively, Type IV and Type II secretion groups (Hueck et al. (1998) *Micro and Mol Biol Rev* 62:379–433). EGY and EGZ differ in substrate range and function synergistically during the hydrolysis of CMC and amorphous cellulose, indicating a potential need for both enzymes for optimal cellulase activity. Specifically, EGZ hydrolyzes cellotriose, cellotetraose, cellopentaose, amorphous cellulose, and CMC. EGY hydrolyses polymeric substrates to products of approximately 10 glucosyl residues.

In another embodiment, the endoglucanases (e.g., EGY and EGZ) are purified separately and combined in a ratio sufficient for the synergistic degradation of an oligosaccharide substrate to occur and this may be determined using the assays disclosed herein. These assays allow for a determination and optimization of a ratio between, e.g., two given glucanases, e.g., endoglucanases. Typically the ratios range from about 9 to 1 to about 19 to 1. In one embodiment, the ratio can be about 9 to 1 or 19 to 1 for EGZ to EGY. In a preferred embodiment, optimum synergy is observed with a high ratio of EGZ to EGY, similar to that produced by *E. chrysanthemi* and by SZ21, a *K. oxytoca* recombinant which expresses celY and celZ (See example 4).

In yet another embodiment, the endoglucanases can be combined concurrently with the oligosaccharide substrate. In yet another embodiment, the endoglucanases can be added to the oligosaccharide substrate sequentially. In a preferred embodiment, EGZ is sequentially added to the substrate following the addition of EGY, after heat inactivation of EGY activity. Example 3 describes, in detail, the synergistic effect of various ratios of endoglucanases (e.g., EGY and EGZ), the synergistic effect of sequential addition of endoglucanases (e.g., EGY and EGZ) (See Table 12), and the effect of various substrate concentrations (See Table 11) and incubation times on the synergistic activity of the endoglucanases.

In yet another embodiment, the synergistic degradation of the oligosaccharide is of a factor of about 1.1, 1.2, 1.3, 1.4, 1.5, 1.6, 1.7, 1.8, 1.9, or 2.0 with a more preferable factor being about 1.8. The synergistic factor is calculated as the observed degradation divided by the sum of predicted contributions from EGY alone and EGZ alone (Riedel, et al. (1997) *FEMS Microbiol. Lett.* 147:239–243). In one embodiment, the endoglucasases are EGY and EGZ. The predicted contribution of EGY alone is about 10% of the total activity, and the predicted contributions of EGZ alone are about 90% of the total activity.

In another aspect of the invention, at least one of the endoglucanases is derived from a cell extract. The cell may be recombinantly engineered to produce at least one endoglucanase. In a preferred embodiment, the cell is recombinantly engineered to produce two endoglucanases (e.g., EGY and EGZ). For example, the cell can be a bacterial cell. The recombinant cell comprises at least one heterologous polynucleotide segment, or, preferably, two or more heterolgous polynucleotides segments, encoding a polypeptide/s under the transcriptional control of one or more heterologous surrogate promoter/s. The heterologous polynucleotide and surrogate promoter may be plasmid based or integrated into the genome of the organism (as described in the examples). In a preferred embodiment, the host cell is used as a source of a desired polypeptide for use in the bioconversion of a complex sugar to ethanol, or a step thereof. In another preferred embodiment, the heterologous polynucleotide segment encodes one or more endoglucanases (e.g., EGY or EGZ) which are expressed at higher levels than are naturally occurring in the host. In one embodiment, the endoglucanases are purified separately from different recombinant cells and subsequently combined to synergistically degrade a substrate (e.g. an oligosaccharide). In another embodiment, one recombinant host cell can produce two or more endoglucanases concurrently and can act synergistically to degrade a substrate.

In another aspect of the invention, the recombinant bacterial host cell is an ethanologenic bacterium such as, for example, *K. oxytoca* P2, an ethanologic derivative of M5A1 (Wood, et al. (1992) *Appl. Environ. Microbiol.* 58:2103–2110). In one embodiment, the ethanologenic bacterium contains at least one heterologous polynucleotide segment (e.g., celY or celZ derived from *Erwinia*) encoding at least one endoglucanase (e.g., EGY or EGZ). In a preferred embodiment, the recombinant ethanologenic bacteria contains more than one heterologous polynucleotide segments which encode endoglucanases. For example, as described in detail in Example 4, celY and celZ can be functionally integrated, expressed, and secreted from the ethanologic strain *K. oxytoca* P2 concurrently to produce ethanol from an oligosaccharide substrate (e.g., crystalline cellulose).

In another embodiment, the recombinant host is a Gram-negative bacterium. In yet another embodiment, the recombinant host is from the family Enterobacteriaceae. The ethanologenic hosts of U.S. Pat. No. 5,821,093, hereby incorporated by reference, for example, are suitable hosts and include, in particular, *E. coli* strains KO4 (ATCC 55123), KO11 (ATCC 55124), and KO12 (ATCC 55125), and *Klebsiella oxytoca* strain P2 (ATCC 55307). Alternatively, a non-ethanologenic host of the present invention may be converted into an ethanologenic host (such as the above-mentioned strains) by introducing, for example, ethanologenic genes from an efficient ethanol producer like *Zymomonas mobilis*. This type of genetic engineering, using standard techniques, results in a recombinant host capable of efficiently fermenting sugar into ethanol. In addition, the LY01 ethanol tolerant strain (ATCC 11303) may be employed as described in published PCT international application WO 98/45425 and this published application is hereby incorporated by reference (see also, e.g., Yomano et al. (1998) *J. of Ind. Micro. & Bio.* 20:132–138).

In another preferred embodiment, the invention makes use of a non-ethanologenic recombinant host, e.g., *E. coli* strain B, *E. coli* strain DH5α, or *Klebsiella oxytoca* strain M5A1. These strains may be used to express at least one desired polypeptide, e.g., an endoglucanase, using techniques described herein. In addition, these recombinant hosts may be used in conjunction with another recombinant host that expresses yet another desirable polypeptide, e.g., a different endoglucanase. For example, a recombinant host producing EGZ can be combined with a recombinant host producing EGY to produce a synergistic effect. In addition, the non-ethanologenic host cell/s may be used in conjunction with an ethanologenic host cell. For example, the use of a non-ethanologenic host/s for carrying out, e.g., the synergistic depolymerization of a complex sugar may be followed by the use of an ethanologenic host for fermenting the depolymerized sugar. Accordingly, it will be appreciated that these reactions may be carried out serially or contemporaneously using, e.g., homogeneous or mixed cultures of non-ethanologenic and ethanologenic recombinant hosts.

In a preferred embodiment, one or more genes for fermenting a sugar substrate into ethanol are provided on a plasmid or integrated into the host chromosome. More preferably, genes for fermenting a sugar substrate into ethanol, e.g., pyruvate decarboxylase (e.g., pdc) and/or alcohol dehydrogenase (e.g., adh) are introduced into the host of the invention using an artificial operon such as the PET operon as described in U.S. Pat. No. 5,821,093, hereby incorporated by reference. Indeed, it will be appreciated that the present invention, in combination with what is known in the art, provides techniques and vectors for introducing multiple genes into a suitable host (see, e.g., *Current Protocols in Molecular Biology*, eds. Ausubel et al., John Wiley & Sons (1992), Sambrook, J. et al., *Molecular Cloning: A Laboratory Manual. 2nd, ed., Cold Spring Harbor Laboratory*, Cold Spring Harbor Laboratory Press, Cold Spring Harbor, N.Y. (1989), and *Bergey's Manual of Determinative Bacteriology*, Kreig et al., Williams and Wilkins (1984), hereby incorporated by reference).

Accordingly, using the methods of the invention, a single genetic construct can encode all of the necessary gene products (e.g., a glucanase, an endoglucanase, an exoglucanase, a secretory protein/s, pyruvate decarboxylase, alcohol dehydrogenase) for performing simultaneous saccharification and fermentation (SSF). For example, Example 4 describes, in detail, the simultaneous saccharification and fermentation (SSF) of crystalline cellulose (Sigmacell 50)

by bacterial cellulases EGY and EGZ produced by ethanologenic *K. oxytoca*, with added commercial cellulase (Spezyme®). The endoglucanases produced by ethanologenic *K. oxytoca* and the commercial cellulase (Spezyme®) function synergistically to increase ethanol production (7% to 22%) from crystalline cellulose (Sigmacell 50). The beneficial effect is attributed almost exclusively to EGY, despite the fact that EGY activities were low in comparison to EGZ. Activity of the ethanologenic *K. oxytoca* strain SZ22, which expresses EGY, was nearly equivalent to the activity of the ethanologenic *K. oxytoca* strain SZ2 1, which expresses both EGY and EGZ activities. *K. oxytoca* strain SZ6, which expresses only EGZ showed little benefit from the production of over 20,000 U of endoglucanase activity per liter.

In one embodiment, the composition of two endoglucanases which act synergistically to degrade an oligosaccharide also includes at least one additional enzymatic activity. This additional activity may be a glucanase activity selected from the group consisting of endoglucanase, exoglucanase, cellobiohydrolase, β-glucosidase, endo-1,4-β-xylanase, α-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase, or a combination thereof. In another embodiment, this additional enzymatic activity may be derived from a fungus, for example *T. longibranchiatum*. Fungi such as *T. longibranchiatum* produce multiple endoglucanase activities, which are presumed to function together with exoglucanases during the hydrolysis of crystalline cellulose (Nidetzky, et al. (1995) *Synergistic interaction of cellulases from Trichoderma reesei during cellulose degradation* p.90–112. In J. N. Saddler and M. E. Himmel (ed.). *Enzymatic degradation of insoluble carbohydrates* ACS symposium series 618, American Chemical Society, Washington, D.C.; Tomme, et al. (1995) *Adv. Microbiol. Physiol.* 37:1–81; Woodward, J. (1991) *Bioresource Technol.* 36:67–75).

In contrast to EGZ, EGY does not hydrolyze soluble cellobiosides but preferentially acts on longer chain substrates, producing ends, which can function as new sites for exoglucanase activity. In the absence of fungal cellulase additions, EGY and EGZ function synergistically to degrade amorphous cellulose. In nature, lignocellulosic substrates are depolymerized by mixtures of extracellular enzymes produced by consortia of fungi and bacteria. Thus, a mixture of *E. chrysanthemi* enzymes and enzymes from the fungus *T. reesei* can improve the digestion of lignocellulosic substrates during bioconversion to ethanol.

It will also be appreciated that a recombinant host may be further manipulated, using methods known in the art, to have mutations in any endogenous gene/s (e.g., recombinase genes) that would interfere with the stability, expression, function, and secretion of the introduced genes. Further, it will also be appreciated that the invention is intended to encompass any regulatory elements, gene/s, or gene products, i.e., polypeptides, that are sufficiently homologous to the ones described herein.

For effective degradation of oligosaccharides, the glucanase (e.g., EGY or EGZ) is preferably secreted into the extracellular millieu. Accordingly, in another embodiment of the invention, the host cell has been engineered to express a secretory protein/s to facilitate the export of the desired polypeptide from the cell. In one embodiment, the secretory protein or proteins are derived from a Gram-negative bacterial cell, e.g., a cell from the family Enterobacteriaceae. In another embodiment, the secretory protein/s are from *Erwinia* and are encoded by the out genes. In another embodiment, the secretory proteins are the pul genes derived from *Klebsiella*. The introduction of one or more of these secretory proteins is especially desirable if the host cell is an enteric bacterium, e.g., a Gram-negative bacterium having a cell wall. Representative Gram-negative host cells of the invention are from the family Enterobacteriaceae and include, e.g., *Escherichia* and *Klebsiella*. In one embodiment, the introduction of one or more secretory proteins into the host results in an increase in the secretion of the selected protein, e.g., a glucanase, as compared to naturally-occurring levels of secretion. Preferably, the increase in secretion is at least about 10% and more preferably, 100%, 200%, 300%, 400%, 500%, 600%, 700%, 800%, 900%, 1000%, or more, as compared to naturally-occurring levels of secretion. In a preferred embodiment, the addition of secretion genes allows for the glucanase polypeptide to be produced at higher levels. In a preferred embodiment, the addition of secretion genes allows for the glucanase polypeptide to be produced with higher enzymatic activity. In a most preferred embodiment, the glucanase is produced at higher levels and with higher enzymatic activity. Preferably, an increase in glucanase activity of at least about 10%, more preferably about 20%, 30%, 40%, 50%, 60%, 70%, 80%, 90%, or 100% is observed. Most preferably, an increase in glucanase activity of several fold is obtained, e.g., about 200%, 300%, 400%, 500%, 600%, 700%, 800%, 900%, or 1000%, as compared to cells without secretion genes (e.g., cells that either lack or do not express secretion genes at a sufficient level). The techniques and methods for introducing such genes and measuring increased output of a desired polypeptide such as, e.g., a glucanase, are described in further detail in the examples. Other equivalent methods are known to those skilled in the art.

EGY and EGZ are secreted by different mechanisms. As described in Example 4, approximately 70% of the EGZ produced was secreted as an extracellular product when the *E. chrysanthemi* out genes were added on a plasmid (pCPP2006) consistent with a Type II secretion system (Hueck, C. J. (1998) *Microbiol. Mol. Biol. Rev.* 62:379–433). Half of the EGY activity was secreted in the presence or absence of the out genes consistent with a Type IV secretion system (Hueck, C. J. supra).

Methods for screening strains having the introduced genes (e.g., endoglucanase encoding genes such as celY and celZ and alcohol dehydrogenase genes) are routine and may be facilitated by visual screens that can identify cells expressing either the alcohol dehydrogenase (ADH) or glucanase (e.g., EGZ or EGY) gene product. The ADH gene product produces acetaldehyde that reacts with the leucosulfonic acid derivative of p-roseaniline to produce an intensely red product. Thus, ADH-positive clones can be easily screened and identified as bleeding red colonies. Methods for screening for a polysaccharase activity (e.g., an endoglucanase, such as EGZ or EGY), also results in a clear visual phenotype as described below and in the examples.

Methods for screening for synergism between two endoglucanases are described in detail in the examples. EGY and EGZ can be purified separately from recombinant host cells transformed with a plasmid containing the celY gene or the celZ gene. The cell-free culture broth can be used to determine extracellular endoglucanase activity. Broth containing cells disrupted by ultrasound can be used to determine total activity. Hydrolysis of cellooligosaccharides can be analyzed by thin layer chromatography. Additionally, endoglucanase activity using CMC as a substrate can be determined in vitro by analyzing samples for reducing sugars. Reducing sugars can be measured using 3,5-dinitrosalicyclic acid reagent with glucose as a standard. Synergy is calculated as the observed activity divided by the sum of predicted contributions from EGY alone (10%) plus EGZ alone (90%).

Alternatively, recombinant host cells can be transformed with a plasmid containing both endoglucanases to produce both endoglucanases concurrently. Synergy can be determined as described above. Simultaneous saccharification and fermentation (SSF) can be carried out to observe ethanol production from a substrate (as described in Example 4). In SSF experiments with added commercial cellulase, two of the K. oxytoca recombinants containing at least one E. chrysanthemi endoglucanase produced more ethanol than the parent K. oxytoca strain which lacked the E. chrysanthemi endoglucanases. Both of these strains also produced ethanol levels equivalent to the best yeast SSF experiments (Cho, et al. (1999) J. Microbiol. Biotechnol. 9:340–345) using approximately one-third of the amount of added commercial cellulase (500 FPU/g cellulose versus 18 FPU/g cellulose for recombinant yeast).

Recombinant bacteria expressing, for example, the PET operon typically grow to higher cell densities in liquid culture than the unmodified parent organisms due to the production of neutral rather than acidic fermentation products (Ingram et al., (1988) Appl. Environ. Microbiol. 54:397–404). On plates, ethanologenic clones are readily apparent as large, raised colonies which appear much like yeast. These traits have been very useful during the construction of new strains and can provide a preliminary indication of the utility of new constructs. Rapid evaluations of ethanol producing potential can also be made by testing the speed of red spot development on aldehyde indicator plates (Conway et al., (1987) J. Bacteriol. 169:2591–2597). Typically, strains which prove to be efficient in sugar conversion to ethanol can be recognized by the production of red spots on aldehyde indicator plates within minutes of transfer.

In a most preferred embodiment of the invention, a single host cell is ethanologenic, that is, has all the necessary genes, either naturally occurring or artificially introduced or enhanced (e.g., using a surrogate promoter and/or genes from a different species or strain), such that the host cell has the ability to produce and secrete two glucanases, preferably, an endoglucanase, more preferably at least two endoglucanases sufficient to, degrade a complex sugar, and ferment the degraded sugar into ethanol. Accordingly, such a host is suitable for simultaneous saccharification and fermentation.

Moreover, the present invention takes into account that the native E. coli fermentation pathways produce a mixture of acidic and neutral products (in order of abundance): lactic acid, hydrogen+carbon dioxide (from formate), acetic acid, ethanol, and succinate. However, the Z. mobilis PDC (pyruvate decarboxylase) has a lower Km for pyruvate than any of the competing E. coli enzymes. By expressing high activities of PDC, carbon flow is effectively redirected from lactic acid and acetyl-CoA into acetyaldehyde and ethanol. Small amounts of succinate can be eliminated by deleting the fumarate reductase gene (frd) (Ingram et al., (1991) U.S. Pat. No. 5,000,000; Ohta et al., (1991) Appl. Environ. Microbiol. 57:893–900). Additional mutations (e.g., in the pfl or ldh genes) may be made to completely eliminate other competing pathways (Ingram et al., (1991) U.S. Pat. No. 5,000,000). Additional mutations to remove enzymes (e.g., recombinases, such as recA) that may compromise the stability of the introduced genes (either plasmid-based or integrated into the genome) may also be introduced, selected for, or chosen from a particular background.

In addition, it should be readily apparent to one skilled in the art that the ability conferred by the present invention, to transform genes coding for a protein or an entire metabolic pathway into a single manipulable construct, is extremely useful. Envisioned in this regard, for example, is the application of the present invention to a variety of situations where genes from different genetic loci are placed on a chromosome. This may be a multi-cistronic cassette under the control of a single promoter or separate promoters may be used.

Exemplary E. coli strains that are ethanologenic and suitable for further improvement according to the methods of the invention include, for example, KO4, KO11, and KO12 strains, as well as the LY10 strain, an ethanol-tolerant mutant of the E. coli strain KO11. Ideally, these strains may be derived from the E. coli strain ATCC 11303, which is hardy to environmental stresses and can be engineered to be ethanologenic and secrete a polysaccharase/s. In addition, recent PCR investigations have confirmed that the ATCC 11303 strain lacks all genes known to be associated with the pathogenicity of E. coli (Kuhnert et al., (1997) Appl. Environ. Microbiol. 63:703–709).

Another preferred ethanologenic host for improvement according to the methods of the invention is the E. coli KO11 strain which is capable of fermenting hemicellulose hydrolysates from many different lignocellulosic materials and other substrates (Asghari et al., (1996) J. Ind. Microbiol. 16:42–47; Barbosa et al., (1992) Current Microbiol. 28:279–282; Beall et al., (1991) Biotechnol Bioeng. 38:296–303; Beall et al., (1992) Biotechnol. Lett. 14:857–862; Hahn-Hagerdal et al., (1994) Appl. Microbiol. Biotechnol. 41:62–72; Moniruzzaman et al., (1996) Biotechnol. Lett. 18:955–990; Moniruzzaman et al, (1998) Biotechnol. Lett. 20:943–947; Grohmann et al., (1994) Biotechnol. Lett. 16:281–286; Guimaraes et al., (1992) Biotechnol. Bioeng. 40:41–45; Guimaraes et al., (1992) Biotechnol. Lett. 14:415–420; Moniruzzaman et al., (1997) J. Bacteriol. 179:1880–1886). In FIG. 1, the kinetics of bioconversion for this strain are shown. In particular, this strain is able to rapidly ferment a hemicellulose hydrolysate from rice hulls (which contained 58.5 g/L of pentose sugars and 37 g/L of hexose sugars) into ethanol (Moniruzzaman et al., (1998) Biotechnol. Lett. 20:943–947). It was noted that this strain was capable of fermenting a hemicellulose hydrolysate to completion within 48 to 72 hours, and under ideal conditions, within 24 hours.

Another preferred host cell of the invention is the bacterium Klebsiella. In particular, Klebsiella oxytoca is preferred because, like E. coli this enteric bacterium has the native ability to metabolize monomeric sugars, which are the constituents of more complex sugars. Moreover, K. oxytoca has the added advantage of being able to transport and metabolize cellobiose and cellotriose, the soluble intermediates from the enzymatic hydrolysis of cellulose (Lai et al., (1996) Appl. Environ. Microbiol. 63:355–363; Moniruzzaman et al., (1997) Appl. Environ. Microbiol. 63:4633–4637; Wood et al., (1992) Appl. Environ. Microbiol. 58:2103–2110). The invention provides genetically engineered ethanologenic derivatives of K. oxytoca, e.g., strain M5A1 having the Z. mobilis pdc and adhB genes encoded within the PET operon (as described herein and in U.S. Pat. No. 5,821,093; Wood et al., (1992) Appl. Environ. Microbiol. 58:2103–2110).

Accordingly, the resulting organism, strain P2, produces ethanol efficiently from monomer sugars and from a variety of saccharides including raffinose, stachyose, sucrose, cellobiose, cellotriose, xylobiose, xylotriose, maltose, etc.

(Burchhardt et al., (1992) *Appl. Environ. Microbiol.* 58:1128–1133; Moniruzzaman et al., (1997) *Appl. Environ. Microbiol.* 63:4633–4637; Moniruzzaman et al., (1997) *J. Bacteriol.* 179:1880–1886; Wood et al., (1992) *Appl. Environ. Microbiol.* 58:2103–2110). These strains may be further modified according to the methods of the invention to express and secrete one or more polysaccharases (e.g., endoglucanases). Accordingly, this strain is suitable for use in the bioconversion of a complex saccharide in an SSF process (Doran et al., (1993) *Biotechnol. Progress.* 9:533–538; Doran et al., (1994) *Biotechnol. Bioeng.* 44:240–247; Wood et al., (1992) *Appl. Environ. Microbiol.* 58:2103–2110). In particular, the use of this ethanologenic P2 strain eliminates the need to add supplemental cellobiase, and this is one of the least stable components of commercial fungal cellulases (Grohmann, (1994) *Biotechnol. Lett.* 16:281–286).

Screen for Promoters Suitable for Use in Heterologous Gene Expression

While in one embodiment, the surrogate promoter of the invention is used to improve the expression of a heterologous gene, e.g., a polysaccharase (an endoglucanase for example), it will be appreciated that the invention also allows for the screening of surrogate promoters suitable for enhancing the expression of any desirable gene product. In general, the screening method makes use of the cloning vector described in Example 1 and depicted in FIG. 3 that allows for candidate promoter fragments to be conveniently ligated and operably-linked to a reporter gene. In one embodiment, the celZ gene encoding glucanase serves as a convenient reporter gene because a strong colorimetric change results from the expression of this enzyme (glucanase) when cells bearing the plasmid are grown on a particular media (CMC plates). Accordingly, candidate promoters, e.g., a particular promoter sequence or, alternatively, random sequences that can be "shotgun" cloned and operably linked to the vector, can be introduced into a host cell and resultant colonies are scanned, visually, for having increased gene expression as evidenced by a phenotypic glucanase-mediated colorimetric change on a CMC plate. Colonies having the desired phenotype are then processed to yield the transforming DNA and the promoter is sequenced using appropriate primers (see Example 1 for more details).

Figure 4:
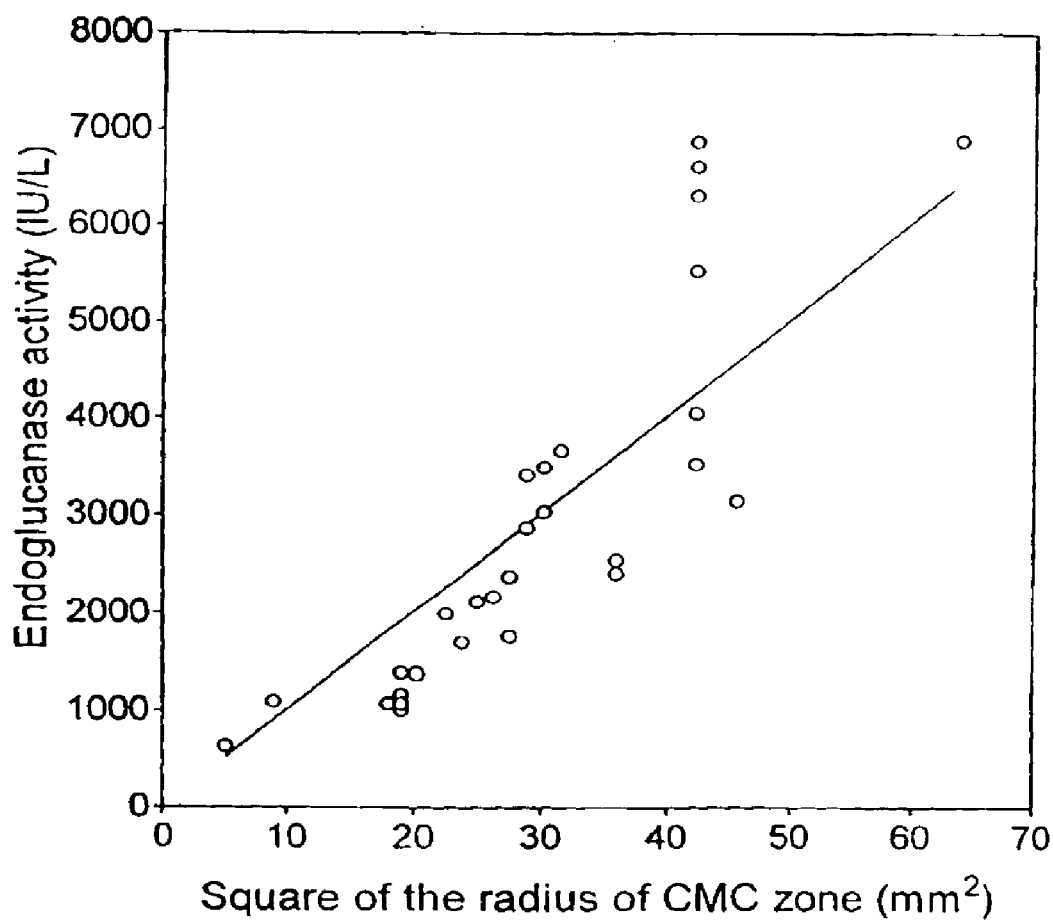
FIG. 4 is a graph showing the high correspondence between the size of the zone of clearance on CMC indicator plates (x-axis) measured for a transformed bacterial colony and the amount of glucanase activity expressed (y-axis).

The high correspondence between the glucanase-mediated colorimetric change on a CMC plate and expression levels of the enzyme is an excellent indication of the strength of a candidate promoter (FIG. 4). Hence, the methods of the invention provide a rapid visual test for rating the strength of candidate surrogate promoters. Accordingly, depending on the desired expression level needed for a specific gene product, a particular identified surrogate promoter can be selected using this assay. For example, if simply the highest expression level is desired, then the candidate promoter that produces the largest colorimetric change may be selected. If a lower level of expression is desired, for example, because the intended product to be expressed is toxic at high levels or must be expressed at equivalent levels with another product, a weaker surrogate promoter can be identified, selected, and used as described.

Figure 13:
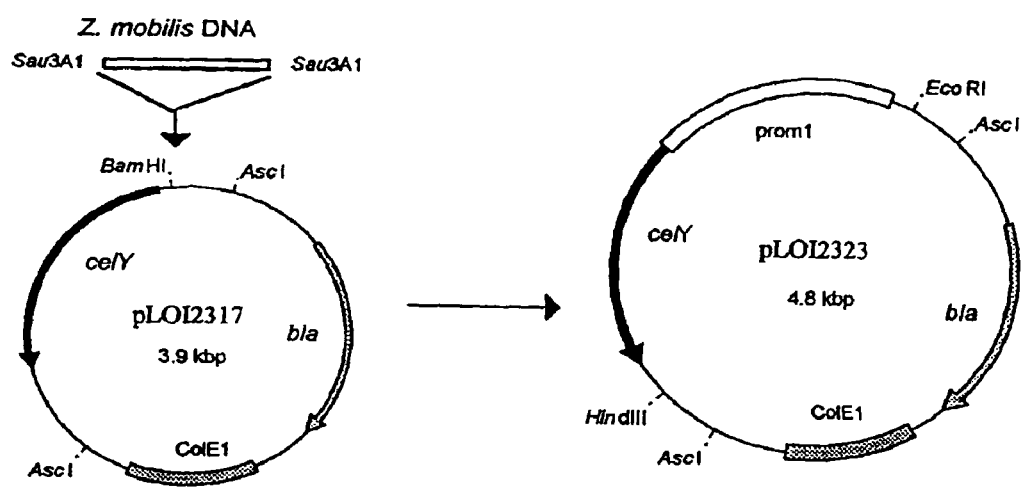
FIG. 13 is a schematic representation of the construction of a promoter-probe vector for celY Sau3AI fragments of Z. mobilis chromosomal DNA were ligated into the BamHI site of pLOI2317 to provide a strong, surrogate promoter for celY coding region (solid segments). Z. mobilis DNA fragments (promoter 1 and promoter 2) are shown as open segments. Replicons and antibiotic resistance genes are stippled; other vector DNA is shown as thin connecting lines. Arrows indicate direction of transcription.

The plasmid pLOI2311 contains the celY coding region under the control of the lac promoter and pLOI2316 was identified as a clone oriented to express celY from the lac promoter as determined by endoglucanase indicator plates. Replacement of the native promoter with the lac promoter increased celY expression by recombinant *E. coli* harboring this plasmid. In addition, to minimize problems associated with the expression of heterologous genes in industrial strains such as the ethanologenic *K. oxytoca* P2 strain, unregulated promoters were isolated from random fragments of *Z. mobilis* DNA using functional assays. Using this method, a plasmid containing a *Z. mobilis* Sau3A1 fragment as a heterlogous was constructed (pLOI2323) (see example 4 and FIGS. 13 and 14). In addition, high levels of EGZ were produced by *E. coli* harboring the plasmid pLOI1620. See examples 3 and 4 for more details concerning the construction of the plasmids and selection of heterologous promoters.

Figure 15:
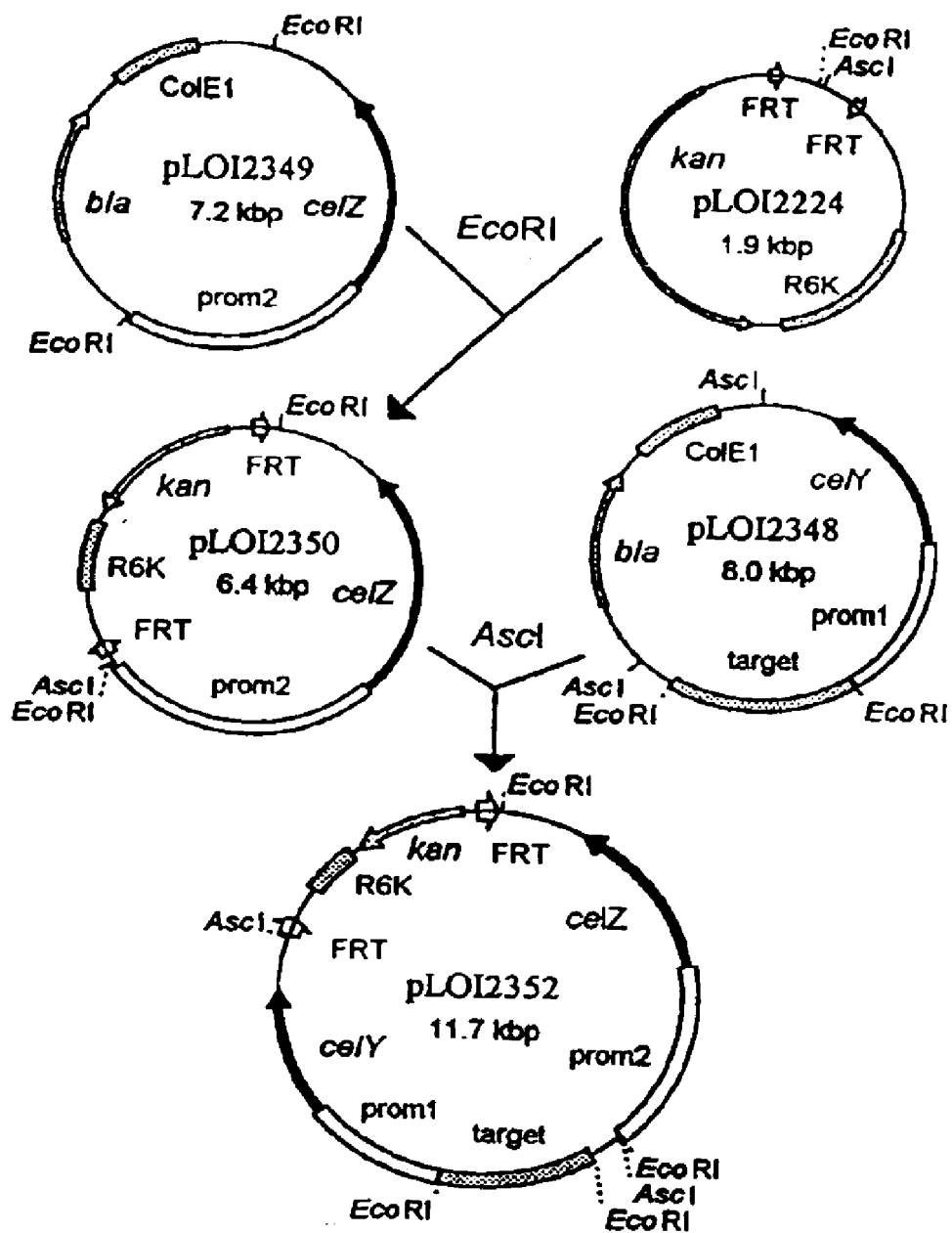
FIG. 15 is a schematic representation of the construction of pLOI2352 for the functional integration of celY and celZ into the chromosome of ethanologenic K. oxytoca P2. Coding regions for celY and celZ are shown as solid segments. Fragments of Z. mobilis DNA that serve as promoters (prom1 and prom2) are shown as open segments. Replicons and antibiotic resistance genes are stippled; other vector DNA is shown as a thin connecting line. Arrows on segments indicate the direction of transcription. The small open arrows represent the FRT sites, which are recognized by the flp recombinase. FRT sequences are asymmetrical and arranged to allow the deletion of plasmid DNA (replicon and selectable marker) after chromosomal integration.

Example 4 describes the construction of the celY, celZ integration vector with surrogate promoters (pLOI2352) (See FIG. 15). To ensure the stability of this plasmid, hybrid genes were integrated into the chromosome, and the antibiotic resistance markers used in construction were deleted using the FLP recombinase system (Martinez-Morales, et al. (1999) *J. Bacteriol.* 181:7143–7148) to facilitate further genetic modifications.

III. Methods of Use

Degrading or Depolymerizing a Complex Saccharide

In one embodiment, the host cell of the invention is used to degrade or depolymerize a complex sugar, e.g., lignocellulose or an oligosaccharide into a smaller sugar moiety. To accomplish this, the host cell of the invention preferably expresses one or more polysaccharases, e.g., endoglucanases, such as EGY and EGZ and these polysaccharases may be liberated naturally from the producer organism. Alternatively, the polysaccharase is liberated from the producer cell by physically disrupting the cell. Various methods for mechanically (e.g., shearing, sonication), enzymatically (e.g., lysozyme), or chemically disrupting cells, are known in the art, and any of these methods may be employed. Once the desired polypeptide is liberated from the inner cell space it may be used to degrade a complex saccharide substrate into smaller sugar moieties for subsequent bioconversion into ethanol. The liberated polysaccharase may be purified using standard biochemical techniques known in the art. Alternatively, the liberated polysaccharase need not be purified or isolated from the other cellular components and can be applied directly to the sugar substrate.

Accordingly, it will be appreciated by the skilled artisan that one or more polysaccharases can be selected for their activity and a composition may be formulated having an optimized activity, preferably synergistic activity, for degrading a complex sugar. The composition may take e.g., the form of an unpurified, semi-purified, or purified endoglucanase activity which is mixed with one or more endoglucanase activities in a ratio that provides optimal degrading of a complex sugar. Alternatively, each enzyme activity may be separately formulated with instructions for use, i.e., mixing or applying in a preferred order and/or ratio, in order to achieve optimal degrading of a complex sugar.

In another embodiment, a host cell is employed that coexpresses one or more polysaccharases and a secretory protein/s such that the polysaccharases are secreted into the growth medium. This eliminates the above-mentioned step of having to liberate the polysaccharases from the host cell. When employing this type of host, the host may be used directly in an aqueous solution containing an oligosaccharide.

In another embodiment, a host cell of the invention is designed to express more than one polysaccharase or is mixed with another host expressing a different polysaccharase in a ratio sufficient for the synergistic degradation of an oligosaccharide to occur. For example, one host cell could express a heterologous endoglucanase (e.g., EGY) while another host cell could express another endoglucanase (e.g., EGZ), and these cells could be combined to form a heterogeneous culture having synergistic activity in the degradation of oligosaccharides. Alternatively, in a preferred embodiment, a single host strain is engineered to produce all of the above polysaccharases. In either case, a culture of recombinant host/s is produced having high expression of the desired polysaccharases for application to an oligosaccharide. If desired, this mixture can be combined with an additional cellulase, e.g., an exogenous cellulase, such as a fungal cellulase. This mixture is then used to degrade a complex substrate. Alternatively, prior to the addition of the complex sugar substrate, the polysaccharase/s are purified from the cells and/or media using standard biochemical techniques and used as a pure enzyme source for depolymerizing a sugar substrate.

It will be appreciated by the skilled artisan, that the ethanol-producing bacterial strains of the invention are superior hosts for the production of recombinant proteins because, under anaerobic conditions (e.g., in the absence of oxygen), there is less opportunity for improper folding of the protein (e.g., due to inappropriate disulfide bond formation). Thus, the hosts and culture conditions of the invention potentially result in the greater recovery of a biologically active product.

Fermenting a Complex Saccharide

In a preferred embodiment of the present invention, the host cell having the above mentioned attributes is also ethanologenic. Accordingly, such a host cell can be applied in synergistically degrading or depolymerizing a complex saccharide into a monosaccharide. Subsequently, the cell can catabolize the simpler sugar into ethanol by fermentation. This process of concurrent complex saccharide depolymerization into smaller sugar residues followed by fermentation is referred to as simultaneous saccharification and fermentation (SSF).

Typically, fermentation conditions are selected that provide an optimal pH and temperature for promoting the best growth kinetics of the producer host cell strain and catalytic conditions for the enzymes produced by the culture (Doran et al., (1993) *Biotechnol. Progress.* 9:533–538). For example, for *Klebsiella*, e.g., the P2 strain, optimal conditions were determined to be between 35–37° C. and pH 5.0–pH 5.4. Under these conditions, even exogenously added fungal endoglucanases and exoglucanases are quite stable and continue to function for long periods of time. Other conditions are discussed in the Examples. Moreover, it will be appreciated by the skilled artisan, that only routine experimentation is needed, using techniques known in the art, for optimizing a given fermentation reaction of the invention.

Currently, the conversion of a complex saccharide such as lignocellulose, is a very involved, multi-step process. For example, the lignocellulose must first be degraded or depolymerized using acid hydrolysis. This is then followed by steps that separate liquids from solids and these products are subsequently washed and detoxified to result in cellulose that can be further depolymerized (using added cellulases) and finally, fermented by a suitable ethanologenic host cell. In contrast, the fermenting of corn is much simpler in that amylases can be used to break down the corn starch for immediate bioconversion by an ethanologenic host in essentially a one-step process.

Accordingly, it will be appreciated by the skilled artisan that the recombinant hosts and methods of the invention afford the use of a similarly simpler and more efficient process for fermenting lignocellulose. For example, the method of the invention is intended to encompass a method that avoids acid hydrolysis altogether. Moreover, the hosts of the invention have the following advantages, 1) efficiency of pentose and hexose co-fermentation; 2) resistance to toxins; 3) production of enzymes for complex saccharide depolymerization; and 4) environmental hardiness. Therefore, the complexity of depolymerizing lignocellulose can be simplified using an improved biocatalyst of the invention. Indeed, in one preferred embodiment of the invention, the reaction can be conducted in a single reaction vessel and in the absence of acid hydrolysis, e.g., as an SSF process.

Potential Substrates for Bioconversion into Ethanol

Figure 2:
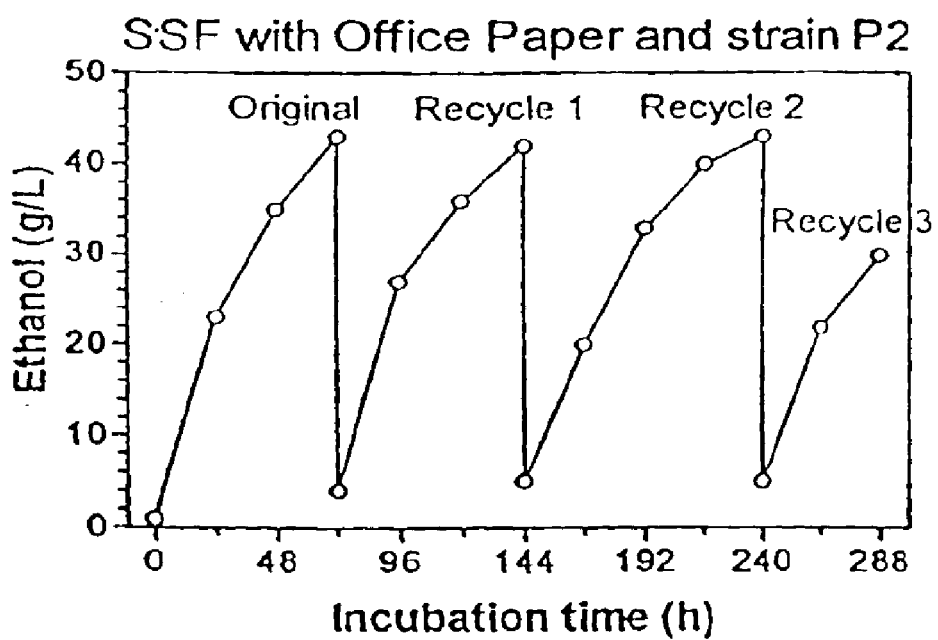
FIG. 2 shows simultaneous saccharification and fermentation (SSF) rates for the ethanologenic recombinant host strain *K. oxytoca* P2 using mixed waste office paper. Insoluble residues from SSF were recycled as a source of bound cellulase enzymes and substrate during subsequent fermentations.

One advantage of the invention is the ability to use a saccharide source that has been, heretofore, underutilized. Consequently, a number of complex saccharide substrates may be used as a starting source for depolymerization and subsequent fermentation using the host cells and methods of the invention. Ideally, a recyclable resource may be used in the SSF process. Mixed waste office paper is a preferred substrate (Brooks et al., (1995) *Biotechnol. Progress.* 11:619–625; Ingram et al., (1995) U.S. Pat. No. 5,424,202), and is much more readily digested than acid pretreated bagasse (Doran et al., (1994) *Biotech. Bioeng.* 44:240–247) or highly purified crystalline cellulose (Doran et al. (1993) *Biotechnol. Progress.* 9:533–538). Glucanases, both endoglucanases and exoglucanases, contain a cellulose binding domain, and these enzymes can be readily recycled for subsequent fermentations by harvesting the undigested cellulose residue using centrifugation (Brooks et al., (1995) *Biotechnol. Progress.* 11:619–625). By adding this residue with bound enzyme as a starter, ethanol yields (per unit substrate) were increased to over 80% of the theoretical yield with a concurrent 60% reduction in fungal enzyme usage (FIG. 2). Such approaches work well with purified cellulose, although the number of recycling steps may be limited with substrates with a higher lignin content. Other substrate sources that are within the scope of the invention include any type of processed or unprocessed plant material, e.g., lawn clippings, husks, cobs, stems, leaves, fibers, pulp, hemp, sawdust, newspapers, etc.

This invention is further illustrated by the following examples, which should not be construed as limiting.

EXAMPLE 1

Methods for Making Recombinant *Escherichia* Hosts Suitable for Fermenting Oligosaccharides into Ethanol In this example, methods for developing and using *Escherichia* hosts suitable for fermenting oligosaccharides into ethanol are described. In particular, a strong promoter is identified which can be used to increase the expression of a polysaccharase (e.g., glucanase). In addition, genes from *Erwinia chrysanthemi* are employed to facilitate polysaccharase secretion thereby eliminating the need for cell disruption in order to release the desired polysaccharase activity.

Throughout this example, the following materials and methods are used unless otherwise stated.

Materials and Methods

Organisms and Culture Conditions

The bacterial strains and plasmids used in this example are listed in Table 1, below.

For plasmid constructions, the host cell *E. coli* DH5α was used. The particular gene employed encoding a polysaccharase (e.g., glucanase) was the celZ gene derived from

*Erwinia chrysanthemi* P86021 (Beall, (1995) Ph.D. Dissertation, University of Florida; Wood et al., (1997) *Biotech. Bioeng.* 55:547–555). The particular genes used for improving secretion were the out genes derived from *E. chrysanthemi* EC16 (He et al., (1991) *Proc. Natl. Acad. Sci. USA.* 88:1079–1083).

binant or integrant host cells containing resistance markers. Constructs containing plasmids with a temperature conditional pSC101 replicon (Posfai et al., (1997) *J. Bacteriol.* 179:4426–4428) were grown at 30° C. and, unless stated otherwise, constructs with pUC-based plasmids were grown at 37° C.

TABLE 1

Strains and Plasmids Used

| Strains/Plasmids | Description | Sources/References |
|---|---|---|
| Strains | | |
| *Z. mobilis* CP4 | Prototrophic | Osman, et al., (1985) J. Bact. 164: 173–180 |
| *E. coli* strain DH5α | lacZ M15 recA | Bethesda Research Laboratory |
| *E. coli* strain B | Prototrophic | ATCC 11303 |
| *E. coli* strain HB 101 | RecA lacY recA | ATCC 37159 |
| Plasmids | | |
| pUC19 | bla cloning vector | New England Biolabs |
| pST76-K | kan low copy number, temp. sensitive | Posfai, et al., (1997) J. Bacteriol. 179: 4426–4428 |
| pRK2013 | kan mobilizing helper plasmid (mob+) | ATCC |
| pCPP2006 | $Sp^r$, ca. 40 kbp plasmid carrying the complete out genes from *E. chrysanthemi* EC16 | He, et al,. (1991) P.N.A.S. 88: 1079–1083 |
| pLOI1620 | bla celZ | Beall, et al, (1995) Ph.D. Dissertation, U. of Florida |
| pLOI2164 | pLOI1620 with BamHI site removed (Klenow) | See text |
| pLOI2170 | NdeI-HindIII fragment (promoterless celZ) from pLOI2164 cloned into pUC19 | See text |
| pLOI2171 | BamHI-SphI fragment (promoterless celZ) from pLOI2170 cloned into pST76-K | See text |
| pLOI2173 | EcoRI-SphI fragment (celZ with native promoter) from pLOI2164 cloned into pST76-K | See text |
| pLOI2174 | EcoRI-BamHI fragment (gap promoter) cloned into pLOI2171 | See text |
| pLOI2175 | EcoRI-BamHI fragment (eno promoter) cloned into pLOI2171 | See text |
| pLOI2177 | Random Sau3A1 *Z. mobilis* DNA fragment cloned into pLOI2171 | See text |
| pLOI2178 | Random Sau3A1 *Z. mobilis* DNA fragment cloned into pLOI2171 | See text |
| pLOI2179 | Random Sau3A1 *Z. mobilis* DNA fragment cloned into pLOI2171 | See text |
| pLOI2180 | Random Sau3A1 *Z. mobilis* DNA fragment cloned into pLOI2171 | See text |
| pLOI2181 | Random Sau3A1 *Z. mobilis* DNA fragment cloned into pLOI2171 | See text |
| pLOI2182 | Random Sau3A1 *Z. mobilis* DNA fragment cloned into pLOI2171 | See text |
| pLOI2183 | Random Sau3A1 *Z. mobilis* DNA fragment cloned into pLOI2171 | See text |
| pLOI2184 | Random Sau3A1 *Z. mobilis* DNA fragment cloned into pLOI2171 | See text |
| pLOI2196 | pLOI2177 fused into pUC19 at the PstI site | See text |
| pLOI2197 | pLOI2180 fused into pUC19 at the PstI site | See text |
| pLOI2198 | pLOI2182 fused into pUC19 at the PstI site | See text |
| pLOI2199 | pLOI2183 fused into pUC19 at the PstI site | See text |
| pLOI2307 | EcoRI-SphI fragment from pLOI2183 cloned into pUC19 | See text |

Typically, host cell cultures were grown in Luria-Bertani broth (LB) (10 g $L^{-1}$ Difco® tryptone, 5 g $L^{-1}$ Difco® yeast extract, 5 g $L^{-1}$ sodium chloride) or on Luria agar (LB supplemented with 15 g $L^{-1}$ of agar). For screening host cells having glucanase celZ activity (EGZ), CMC-plates (Luria agar plates containing carboxymethyl cellulose (3 g $L^{-1}$)) were used (Wood et al., (1988) *Methods in Enzymology* 160:87–112). When appropriate, the antibiotics ampicillin (50 mg $L^{-1}$), spectinomycin (100 g $L^{-1}$), kanamycin (50 g $L^{-1}$) were added to the media for selection of recom- Genetic Methods Standard techniques were used for all plasmid constructions (Ausubel et al., (1987) *Current Protocols in Molecular Biology*, John Wiley & Sons, Inc.; Sambrook et al., (1989) *Molecular cloning: a laboratory manual*, $2^{nd}$ ed. C.S.H.L., Cold Spring Harbor, N.Y.). For conducting small-scale plasmid isolation, the TELT procedure was performed. For large-scale plasmid isolation, the Promega® Wizard Kit was used. For isolating DNA fragments from gels, the Qiaquick® Gel Extraction Kit from Qiagen® was employed. To isolate chromosomal DNA from *E. coli* and *Z.*

*mobilis* the methods of Cutting and Yomano were used (Cutting et al., (1990), Genetic analysis, pp. 61–74, In, Molecular biological methods for *Bacillus*, John Wiley & Sons, Inc.; Yomano et al., (1993) *J. Bacteriol.* 175:3926–3933).

To isolate the two glycolytic gene promoters (e.g., gap and eno) described herein, purified chromosomal DNA from *E. coli* DH5α was used as a template for the PCR (polymerase chain reaction) amplification of these nucleic acids using the following primer pairs: gap promoter, 5'-CGAATTCCTGCCGAAGTTTATTAGCCA-3' (SEQ ID NO: 3) and 5'-AAGGATCCTTCCACCAGCTATTTGTTAGTGA-3' (SEQ ID NO: 4); eno promoter, 5'-AGAATTCTGCCAGTTGGTTGACGATAG-3' (SEQ ID NO: 5) and 5'-CAGGATCCCCTCAAGTCACTAGTTAAACTG-3' (SEQ ID NO: 6). The out genes encoding secretory proteins derived from *E. chrysanthemi* (pCPP2006) were conjugated into *E. coli* using pRK2013 for mobilization (Figurski et al., (1979) *Proc. Natl. Acad. Sci. USA*. 76: 1648–1652; Murata et al., (1990) *J. Bacteriol.* 172:2970–2978).

To determine the sequence of various DNAs of interest, the dideoxy sequencing method using fluorescent primers was performed on a LI-COR Model 4000-L DNA Sequencer. The pST76-K-based plasmids were sequenced in one direction using a T7 primer (5'-TAATACGACTCACTATAGGG-3' (SEQ ID NO: 7)). The pUC18- and pUCI9-based plasmids were sequenced in two directions using either a forward primer (5'-CACGACGTTGTAAAACGAC-3' (SEQ ID NO: 8)) or a reverse primer (5'-TAACAATTTCACACAGGA-3' (SEQ ID NO: 9)). The extension reactions of the sequencing method were performed using a Perkin Elmer GeneAmp® PCR 9600 and SequiTherm Long-Read Sequencing Kit-LC®. Resultant sequences were subsequently analyzed using the Wisconsin Genetic Computer Group (GCG) software package (Devereux et al., (1984) *Nucleic Acids Rev.* 12:387–395).

To determine the start of transcriptional initiation in the above-mentioned promoters, primer extension analysis was performed using standard techniques. In particular, promoter regions were identified by mapping the transcriptional start sites using a primer finding correspondence within the celZ gene RNA that was isolated from cells in late exponential phase using a Qiagen RNeasy® kit. Briefly, cells were treated with lysozyme (400 µg/ml) in TE (Tris-HCl, EDTA) containing 0.2 M sucrose and incubated at 25° C. for 5 min prior to lysis. Liberated RNA was subjected to ethanol precipitation and subsequently dissolved in 20 µl of Promega™ AMV reverse transcriptase buffer (50 mM Tris-HCl, pH 8.3, 50 mM KCl, 10 mM $MgCl_2$, 0.5 mM spermadine, 10 mM DTT). An IRD41-labeled primer (5'-GACTGGATGGTTATCCGAATAAGAGAGAGG-3' (SEQ ID NO: 10)) from LI-Cor Inc. was then added and the sample was denatured at 80° C. for 5 min, annealed at 55° C. for 1 hr, and purified by alcohol precipitation. Annealed samples were dissolved in 19 µl of AMV reverse transcriptase buffer containing 500 µM dNTPs and 10 units AMV reverse transcriptase, and incubated for extension (1 h at 42° C.). Products were treated with 0.5 µg/ml DNase-free RNase A, precipitated, dissolved in loading buffer, and compared to parallel dideoxy promoter sequences obtained using the LI-COR Model 4000-L DNA sequencer.

Polysaccharase Activity

To determine the amount of polysaccharase activity (e.g., glucanase activity) resulting from expression of the celZ gene, a Congo Red procedure was used (Wood et al., (1988) *Methods in Enzymology* 160:87–112). In particular, selected clones were transferred to gridded CMC plates and incubated for 18 h at 30° C. and then stained and recombinant host cells expressing glucanase formed yellow zones on a red background. Accordingly, the diameters of these colorimetric zones were recorded as a relative measure of celZ expression.

Glucanase activity (EGZ) was also measured using carboxymethyl cellulose as a substrate. In this test, appropriate dilutions of cell-free culture broth (extracellular activity) or broth containing cells treated with ultrasound (total activity) were assayed at 35° C. in 50 mM citrate buffer (pH 5.2) containing carboxymethyl cellulose (20 g $L^{-1}$). Conditions for optimal enzyme release for 3–4 ml samples were determined to be 4 pulses at full power for 1 second each using a cell disruptor (Model W-220F, Heat System-Ultrasonics Inc., Plainview, N.Y.). To stop the enzyme reactions of the assay, samples were heated in a boiling water bath for 10 min. To measure reducing sugars liberated enzymatically by the glucanase, a dinitrosalicylic acid reagent was employed using glucose as a standard (Wood et al., (1988) *Methods in Enzymology* 160:87–112). The amount of enzyme activity (IU) was expressed as µmols of reducing sugar released per min or as a percentage of total activity from an average of two or more determinations.

Ultrastructural Analysis

To determine the ultrastructure of various recombinant host cells, fresh colonies from Luria agar plates were prepared for analysis by fixing in 2% glutaraldehyde in 0.2 M sodium cacodylate buffer (pH 7) followed by incubation in 1% osmium tetroxide and followed by 1% uranyl acetate in distilled water. Samples were dehydrated in ethanol, embedded in Spurr's plastic, and ultrathin sections were prepared and examined using a Zeiss® EM-IOCA electron microscope (Spur (1969)*J. Ultrastruct. Res.* 26:31).

Figure 3:
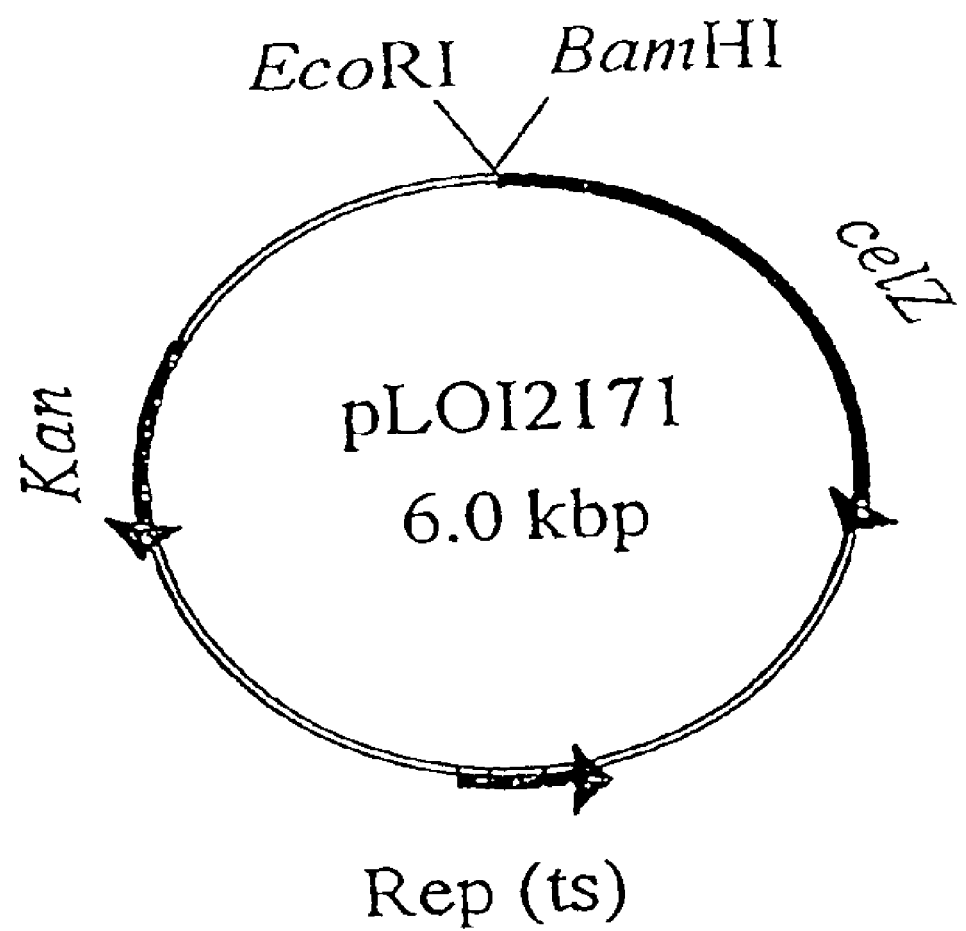
FIG. 3 shows the structure of the plasmid pLOI2171, a low copy promoter probe vector showing the orientation of the kanamycin resistance gene (kan) for selection, the temperature sensitive pSC101 replicon (Rep(ts)) for episomal maintenance of the plasmid, and the promoterless polysaccharase gene celZ encoding phospho-beta-glucosidase (EGZ).

Construction of a Low Copy Promoter Probe Vector Using celZ as the Reporter Gene To facilitate the isolation of strong promoters, a low copy vector was constructed with a pSC101 replicon and a BamHI site immediately preceding a promoterless celZ gene (pLOI2171). Accordingly, this promoterless plasmid was used as a negative control. The plasmid pLOI1620 was used as a source of celZ and is a pUC18 derivative with expression from consecutive lac and celZ promoters. The BamHI site in this plasmid was eliminated by digestion and Klenow treatment (pLOI2164). The celZ gene was isolated as a promoterless NdeI fragment after Klenow treatment. The resulting blunt fragment was digested with HindIII to remove downstream DNA and ligated into pUC19 (HindIII to HincII) to produce pLOI2170. In this plasmid, celZ is oriented opposite to the direction of lacZ transcription and was only weakly expressed. The BamHI (amino terminus)-SphI (carboxyl terminus) fragment from pLOI2170 containing celZ was then cloned into the corresponding sites of pST76-K, a low copy vector with a temperature sensitive replicon, to produce pLOI2171 (FIG. 3). Expression of celZ in this vector was extremely low facilitating its use as a probe for candidate strong promoters.

Analysis of celZ Expression from Two *E. coli* Glycolytic Promoters (gap and eno) Two exemplary promoters driving glycolytic genes (gap and eno) in *E. coli* were examined for their ability to drive the expression of the heterologous celZ gene encoding glucanase. Chromosomal DNA from the *E. coli* DH5α strain was used as a template to amplify the gap and eno promoter regions by the polymerase chain reaction. The resulting fragments of approximately 400 bp each were digested with EcoRI and BamHI and cloned into the corresponding sites in front of a promoterless celZ gene in pLOI2171 to produce pLOI2174 (gap promoter) and pLOI2175 (eno promoter). As a control, the EcoRI-SphI fragment from pLOI2164 containing the complete celZ gene and native *E. chrysanthemi* promoter was cloned into the corresponding sites of pST76-K to produce pLOI2173. These three plasmids were transformed into *E. coli* strains B and DH5α and glucanase activity (EGZ) was compared. For both strains of *E. coli*, glucanase activities were lower on CMC plates with *E. coli* glycolytic promoters than with pLOI2173 containing the native *E. chrysanthemi* promoter (Table 2). Assuming activity is related to the square of the radius of each zone (Fick's Law of diffusion), EGZ production with glycolytic promoters (pLOI2174 and pLOI2175) was estimated to be 33% to 65% lower than in the native promoter construct (pLOI2373). Accordingly, other candidate promoters for driving high levels of celZ gene expression were investigated.

Identifying and Cloning Random DNA Fragments Suitable for Use as Promoters for Heterologous Gene Expression Random fragments derived from *Z. mobilis* can be an effective source of surrogate promoters for the high level expression of heterologous genes in *E. coli*. (Conway et al., (1987) *J. Bacteriol.* 169:2327–2335; Ingram et al., (1988) *Appl. Environ. Micro.* 54:397–404). Accordingly, to identify surrogate promoters for *Erwinia* celZ expression, *Z. mobilis* chromosomal DNA was extensively digested with Sau3AI and resulting fragments were ligated into pLOI2171 at the BamHI site and transformed into *E. coli* DH5α to generate a library of potential candidate promoters. To rapidly identify superior candidate promoters capable of driving celZ gene expression in *E. coli*, the following biological screen was employed. Colonies transformed with celZ plasmids having different random candidate promoters were transferred to gridded CMC plates and stained for glucanase activity after incubation (Table 2). Approximately 20% of the 18,000 clones tested were CMC positive. The 75 clones which produced larger zones than the control, pLOI2173, were examined further using another strain, *E. coli* B.

TABLE 2

Evaluation of promoter strength for celZ expression in *E. coil* using CMC indicator plates.

| | *E. coli* DH5α host | | | *E. coli* B host | | |
|---|---|---|---|---|---|---|
| Plasmids | Number of Plasmids[a] | CMC zone diameter (mm)[b] | % of native promoter $(100*R^2_x/R^2_c)$[c] | Number of plasmids | CMC zone diameter (mm) | % of native promoter $(100*R^2_x/R^2_c)$ |
| pLOI2171 (promoterless) | 1 | 0 | — | — | — | — |
| pLOI2173 (native promoter) | 1 | 5.0 | 100 | 1 | 4.5 | 100 |
| pLOI2174 (gap promoter) | 1 | 4.0 | 77 | 1 | 3.5 | 60 |
| pLOI2175 (eno promoter) | 1 | 3.0 | 43 | 1 | 2.8 | 35 |
| *Z. mobilis* promoters | | | | | | |
| Group I | 5 | 13.0 | 676 | 4 | 10.8–11.3 | 570–625 |
| Group II | 14 | 9.0–11.0 | 324–484 | 17 | 9.0–10.5 | 445–545 |
| Group III | 56 | 6.0–9.0 | 144–324 | 54 | 5.0–8.8 | 125–375 |

[a] The number of clones which the indicated range of activities.
[b] The average size of the diameters from three CMC digestion zones.
[c] $R^2_x$ is the square of the radius of the clear zone with the test plasmid; $R^2_c$ is the square of the radius of the clear zone for the control (pLOI2173).

Thus, promoter strength for selected candidate promoters was confirmed in two different strains with, in general, recombinants of DHS5α producing larger zones (e.g., more glucanase) than recombinants of strain B. However, relative promoter strength in each host was similar for most clones. Based on these analyses of glucanase production as measured by zone size using CMC plates, four clones appeared to express celZ at approximately 6-fold higher levels than the construct with the original *E. chrysanthemi* celZ gene (pLOI2173), and at 10-fold higher levels than either of the *E. coli* glycolytic promoters. Accordingly, these and similarly strong candidate promoters were selected for further study.

Production and Secretion of Glucanase

Eight plasmid derivatives of pST76-K (pLOI2177 to pLOI2184) were selected from the above-described screen (see Group I and Group II (Table 2)) and assayed for total glucanase activity in *E. coli* strain B (Table 3). The four plasmids giving rise to the largest zones on CMC plates were also confirmed to have the highest glucanase activities (pLOI2177, pLOI2180, pLOI2182, and pLOI2183). The activities were approximately 6-fold higher than that of the unmodified celZ (pLOI2173), in excellent agreement with our estimate using the square of the radius of the cleared zone on CMC plates. FIG. 4 shows a comparison of activity estimates from CMC plates and in vitro enzyme assays for strain B containing a variety of different promoters, with and without the addition of out genes encoding secretory proteins. Although there is some scatter, a direct relationship is clearly evident which validates the plate method for estimating relative activity. The original construct in pUC18, a high copy plasmid, was also included for comparison (pLOI2164). This construct with consecutive lac and celZ promoters produced less EGZ activity than three of the low copy plasmids with surrogate promoters (pLOI2177, pLOI2182, and pLOI2183). Thus, to increase celZ expression of glucanase even more, the DNA fragment containing celZ and the most effective surrogate promoter was isolated from pLOI2183 (as a EcoRI-SphI fragment) and inserted into pUC19 with transcription oriented opposite to that of the lac promoter (pLOI2307). Accordingly, the above-identified strong surrogate promoter when incorporated into a high copy plasmid, further increased glucanase activity by 2-fold.

Engineering Increased Secretion of Glucanase

To further improve on the above-described results for increasing expression of celZ encoded glucanase, the above host cells were engineered for increased secretion.

Genes encoding secretory proteins (e.g., the out genes) derived from *E. chrysanthemi* EC16 were used for improving the export of the glucanase using the plasmid as described in He et al. that contains out genes (pCPP2006) (He et al., (1991) *Proc. Natl. Acad. Sci. USA.* 88:1079–1083). The increased secretion of EGZ in *E. coli* B was investigated and results are presented in Table 3.

Sequence Analysis of the Strongest Promoter Derived from *Z. mobilis*

The sequences of the four strongest surrogate promoters (pLOI2177, pLOI2180, pLOI2182, and pLOI2183) were determined. To facilitate this process, each was fused with pUC19 at the PstI site. The resulting plasmids, pLOI2196, pLOI2197, pLOI2198, and pLOI2199, were produced at high copy numbers (ColEI replicon) and could be sequenced in both directions using M13 and T7 sequencing primers. All four plasmids contained identical pieces of *Z. mobilis* DNA and were siblings. Each was 1417 bp in length and contained 4 internal Sau3AI sites. DNA and translated protein sequences (six reading frames) of each piece were compared to the current data base. Only one fragment (281 bp internal fragment) exhibited a strong match in a BLAST search (National Center for Biotechnology Information; http://www.ncbi.nlm.nih.gov/BLAST/) and this fragment was 99% identical in DNA sequence to part of the *Z. mobilis* hpnB gene which is proposed to function in cell envelope biosynthesis (Reipen et al., (1995) *Microbiology*

TABLE 3

Comparison of promoters for EGZ production and secretion in *E. coli* B

| Plasmids[a] | Without secretion genes | | With secretion genes (pCPP2006) | |
|---|---|---|---|---|
| | Total activity (IU/L)[b] | Extracellular[c] (%) | Total Activity (IU/L) | Extracellular[c] (%) |
| pLOI2173 | 620 | 17 | 1,100 | 43 |
| pLOI2177 | 3,700 | 10 | 5,500 | 44 |
| pLOI2178 | 2,200 | 9 | 3,500 | 49 |
| pLOI2179 | 2,000 | 10 | 3,000 | 50 |
| pLOI2180 | 2,900 | 8 | 6,300 | 39 |
| pLOI2181 | 1,800 | 11 | 4,100 | 46 |
| pLOI2182 | 3,500 | 7 | 6,600 | 38 |
| pLOI2183 | 3,400 | 7 | 6,900 | 39 |
| pLOI2184 | 2,100 | 12 | 2,400 | 39 |
| pLOI2164 | 3,200 | 20 | 6,900 | 74 |
| pLOI2307 | 6,600 | 28 | 13,000 | 60 |

[a]Plasmids pLOI2173 and pLOI2164 contain the celZ native promoter; pLOI2307 contains the strong promoter from pLOI2183. Plasmids pLOI2164 and pLOI2307 are pUC-based plasmids (high copy number). All other plasmids are derivatives of pST76-K (low copy number).
[b]Glucanase activities were determined after 16 h of growth at 30° C.
[c]Extracellular activity (secreted or released).

Recombinant hosts with low copy plasmids produced only 7–17% of the total EGZ extracellularly (after 16 hours of growth) without the additional heterologous secretory proteins (out proteins encoded by plasmid pCPP2006). A larger fraction of EGZ (20–28%) was found in the extracellular broth surrounding host cells with the high-copy pUC-based plasmids than with the low copy pST76-based plasmids containing the same promoters. However, in either case, the addition of out genes encoding secretory proteins (e.g., pCPP2006) increased the total level of expression by up to 2-fold and increased the fraction of extracellular enzyme (38–74%) by approximately 4-fold. The highest activity, 13,000 IU/L of total glucanase of which 7,800 IU/L was found in the cell-free supernatant was produced by strain B having both pLOI2307 encoding celZ driven by a strong surrogate promoter and pCPP2006 encoding out secretory proteins).

It has been reported that under certain conditions (pH 7, 37° C.), the specific activity for pure EGZ enzyme is 419 IU (Py et al., (1991) *Protein Engineering* 4:325–333) and it has been determined that EGZ produced under these conditions is 25% more active than under the above-mentioned conditions (pH 5.2 citrate buffer, 35° C.). Accordingly, assuming a specific activity of 316 IU for pure enzyme at pH 5.2 (35° C.), the cultures of *E. coli* B (containing pLOI2307 and pCPP2006, e.g., plasmids encoding glucanase and secretory proteins), produced approximately 41 mg of active EGZ per liter or 4–6% of the total host cell protein was active glucanase.

141:155–161). Primer extension analysis revealed a single major start site, 67 bp upstream from the Sau3AI/BamHI junction site with celZ, and a second minor start site further upstream (FIG. 5). Sequences in the -10 and -35 regions were compared to the conserved sequences for *E. coli* sigma factors (Wang et al., (1989) *J. Bacteriol.* 180:5626–5631; Wise et al., (1996) *J. Bacteriol.* 178:2785–2793). The dominant promoter region (approximately 85% of total start site) appears similar to a sigma$^{70}$ promoter while the secondary promoter site resembles a sigma$^{38}$ promoter.

Microscopic Analysis of Recombinant Host Cells Producing Glucanase

Figure 6:
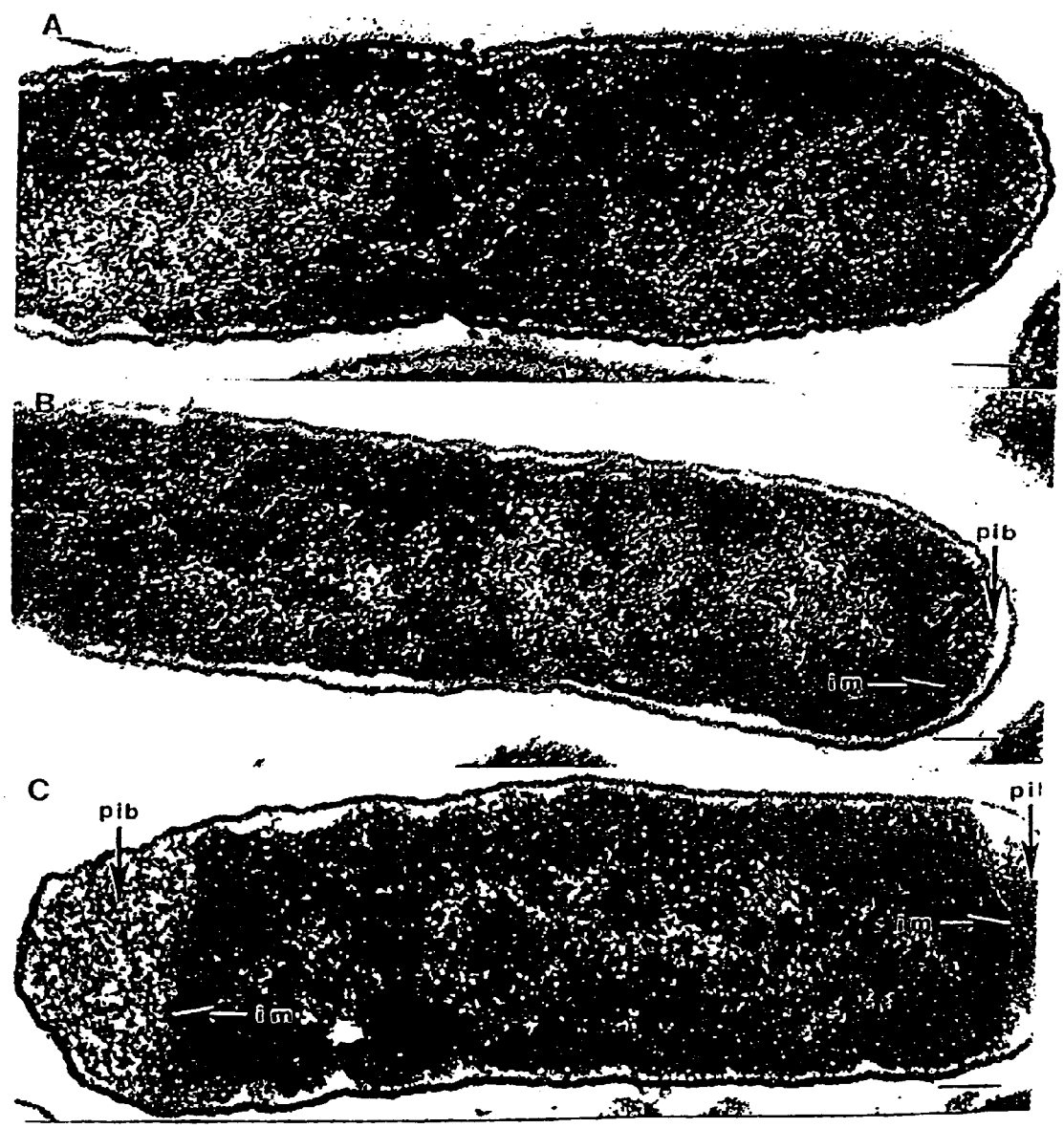
FIG. 6 represents electron micrographs of *E. coli* DH5α cells harboring different plasmids expressing little if any (pUC19; panel A), moderate (pLOI2164; panel B), and high levels (pLOI2307; panel C) of glucanase in the form of periplasmic inclusion bodies (pib) localized between the outer cell wall and the inner membrane (im). The bar shown represents 0.1 μm.

Little difference in cell morphology was observed between recombinants and the parental organism by light microscopy. Under the electron microscope, however, small polar inclusion bodies were clearly evident in the periplasm of strain B (pLOI2164) expressing high amounts of glucanase and these inclusion bodies were presumed to contain EGZ (FIG. 6). In the strain B (pLOI2307) that produced 2-fold higher glucanase activity the inclusion bodies were even larger and occupied up to 20% of the total cell volume. The large size of these polar bodies suggests that glucanase activity measurements may underestimate the total EGZ production. Typically, polar inclusion bodies were smaller in host cells also having constructs encoding the out secretory proteins, which allow for increased secretion of proteins from the periplasmic space. As expected, no periplasmic inclusion bodies were evident in the negative control strain B (pUC19) which does not produce glucanase.

EXAMPLE 2

Recombinant *Klebsiella* Hosts Suitable for Fermenting Oligosaccharides into Ethanol In this example, a recombinant *Klebsiella* host, suitable for use as a biocatalyst for depolymerizing and fermenting oligosaccharides into ethanol, is described.

Throughout this example, the following materials and methods are used unless otherwise stated.

Materials and Methods

Bacteria, Plasmids, and Culture Conditions

The strains and plasmids that were used in this exemplification are summarized in Table 4 below.

TABLE 4

Strains and Plasmids Used

| Strains/Plasmids | Properties | Sources/References |
|---|---|---|
| Strains | | |
| *Zymomonas mobilis* CP4 | Prototrophic | Ingram et al. (1988) Appl. Environ. Micro. 54: 397–404 |
| *Escherichia coli* | | |
| DH5α | lacZ M15 recA | Bethesda Research Laboratory |
| HB101 | recA lacY recA | ATCC 37159 |
| *Klebsiella oxytoca* | | |
| M5A1 | Prototrophic | Wood et al. (1992) Appl. Environ. Micro. 58: 2103–2110 |
| P2 | Pfl::pdc adhB cat | Wood et al. (1992) Appl. Environ. Micro. 58: 2103–2110 |
| SZ1 | pfl::pdc adhB cat; integrated celZ; tet | See text |
| SZ2 | pfl::pdc adhB cat; integrated celZ; tet | See text |
| SZ3 | pfl::pdc adhB cat; integrated celZ; tet | See text |
| SZ4 | pfl::pdc adhB cat; integrated celZ; tet | See text |
| SZ5 | pfl::pdc adhB cat; integrated celZ; tet | See text |
| SZ6 | pfl::pdc adhB cat; integrated celZ; tet | See text |
| SZ7 | pfl::pdc adhB cat; integrated celZ; tet | See text |
| SZ8 | pfl::pdc adhB cat; integrated celZ; tet | See text |
| SZ9 | pfl::pdc adhB cat; integrated celZ; tet | See text |
| SZ10 | pfl::pdc adhB cat; integrated celZ; tet | See text |
| Plasmids | | |
| pUC19 | bla cloning vector | New England Biolabs |
| pBR322 | bla tet cloning vector | New England Biolabs |
| pLOI1620 | bla celZ | Wood et al. (1997) Biotech. Bioeng. 55: 547–555 |
| pRK2013 | kan mobilizing helper plasmid (mob+) | ATCC |
| pCPP2006 | Sp$^r$, 40 kbp fragment containing out genes from *E. chrysanthemi* EC16 | He et al. (1991) P.N.A.S. 88: 1079–1083 |
| pST76-K | kan low copy vector containing temperature sensitive pSC101 replicon | Posfai et al. (1997) J. Bact. 179: 4426–4428 |
| pLOI2164 | bla celZ (BamHI eliminated from pLOI1620) | See text |
| pLOI2173 | kan celZ (native celZ promoter) | See text |
| pLOI2177 | kan celZ (surrogate promoter from *Z. mobilis*) | See text |
| pLOI2178 | kan celZ (surrogate promoter from *Z. mobilis*) | See text |
| pLOI2179 | kan celZ (surrogate promoter from *Z. mobilis*) | See text |
| pLOI2180 | kan celZ (surrogate promoter from *Z. mobilis*) | See text |
| pLOI2181 | kan celZ (surrogate promoter from *Z. mobilis*) | See text |
| pLOI2182 | kan celZ (surrogate promoter from *Z. mobilis*) | See text |
| pLOI2183 | kan celZ (surrogate promoter from *Z. mobilis*) | See text |
| pLOI2184 | kan celZ (surrogate promoter from *Z. mobilis*) | See text |
| pLOI2185 | kan celZ (surrogate promoter from *Z. mobilis*) | See text |
| pLOI2186 | kan celZ (surrogate promoter from *Z. mobilis*) | See text |
| pLOI2187 | kan celZ (surrogate promoter from *Z. mobilis*) | See text |
| pLOI2188 | kan celZ (surrogate promoter from *Z. mobilis*) | See text |

TABLE 4-continued

Strains and Plasmids Used

| Strains/Plasmids | Properties | Sources/References |
|---|---|---|
| pLOI2189 | kan celZ (surrogate promoter from Z. mobilis) | See text |
| pLOI2190 | kan celZ (surrogate promoter from Z. mobilis) | See text |
| pLOI2191 | kan celZ (surrogate promoter from Z. mobilis) | See text |
| pLOI2192 | kan celZ (surrogate promoter from Z. mobilis) | See text |
| pLOI2193 | kan celZ (surrogate promoter from Z. mobilis) | See text |
| pLOI2194 | kan celZ (surrogate promoter from Z. mobilis) | See text |
| pLOI2301 | AscI linker inserted into NdeI site of pUC19 | See text |
| pLOI2302 | AscI linker inserted into SapI site of pLOI2301 | See text |
| pLOI2303 | AvaI-EcoRI fragment from pBR322 inserted into PstI site of pLOI2302 after Klenow treatment | See text |
| pLOI2305 | EcoRI DNA fragment of K. oxytoca M5A1 genomic DNA (Ca. 2.5 kb) cloned into the SmaI site of pLOI2303 | See text |
| pLOI2306 | EcoRI-SphI fragment from pLOI2183 cloned into EcoRI site of pLOI2305 | See text |

The culture conditions used for cultivating E. coli and K. oxytoca M5A1 typically employed Luria-Bertani broth (LB) containing per liter: 10 g Difco® tryptone, 5 g yeast extract, and 5 g sodium chloride, or, alternatively, Luria agar (LB supplemented with 15 g of agar) (Sambrook et al., (1989), Molecular Cloning: A Laboratory Manual, C.S.H.L., Cold Spring Harbor, N.Y.).

For screening bacterial colonies under selective conditions, CMC-plates (Luria agar plates containing 3 g L$^{-1}$ carboxymethyl cellulose) were used to determine levels of glucanase activity expressed by a given bacterial strain (Wood et al. (1988) Enzymology, 160:87–112). For cultivating ethanologenic strains, glucose was added to solid media (20 g L$^{-1}$) and broth (50 g L$^{-1}$). In determining glucanase activity, the glucose in the growth media was replaced with sorbitol (50 g L$^{-1}$), a non-reducing sugar. For cultivating various strains or cultures in preparation for introducing nucleic acids by electroporation, a modified SOC medium was used (e.g., 20 g L$^{-1}$ Difco® tryptone, 5 g L$^{-1}$, Difco® yeast extract, 10 mM NaCl, 2.5 mM KCl, 10 mM MgSO$_4$, 10 mM MgCl$_2$, and 50 g L$^{-1}$ glucose). The antibiotics ampicillin (50 mg L$^{-1}$), spectinomycin (100 mg L$^-$), kanamycin (50 mg L$^{-1}$), tetracycline (6 or 12 mg L$^-$), and chloramphenicol (40, 200, or 600 mg L$^-$) were added when appropriate for selection of recombinant hosts bearing antibiotic resistance markers. Unless stated otherwise, cultures were grown at 37° C. Ethanologenic strains and strains containing plasmids with a temperature-sensitive pSC101 replicon were grown at 30° C.

Genetic Methods

Figure 7:
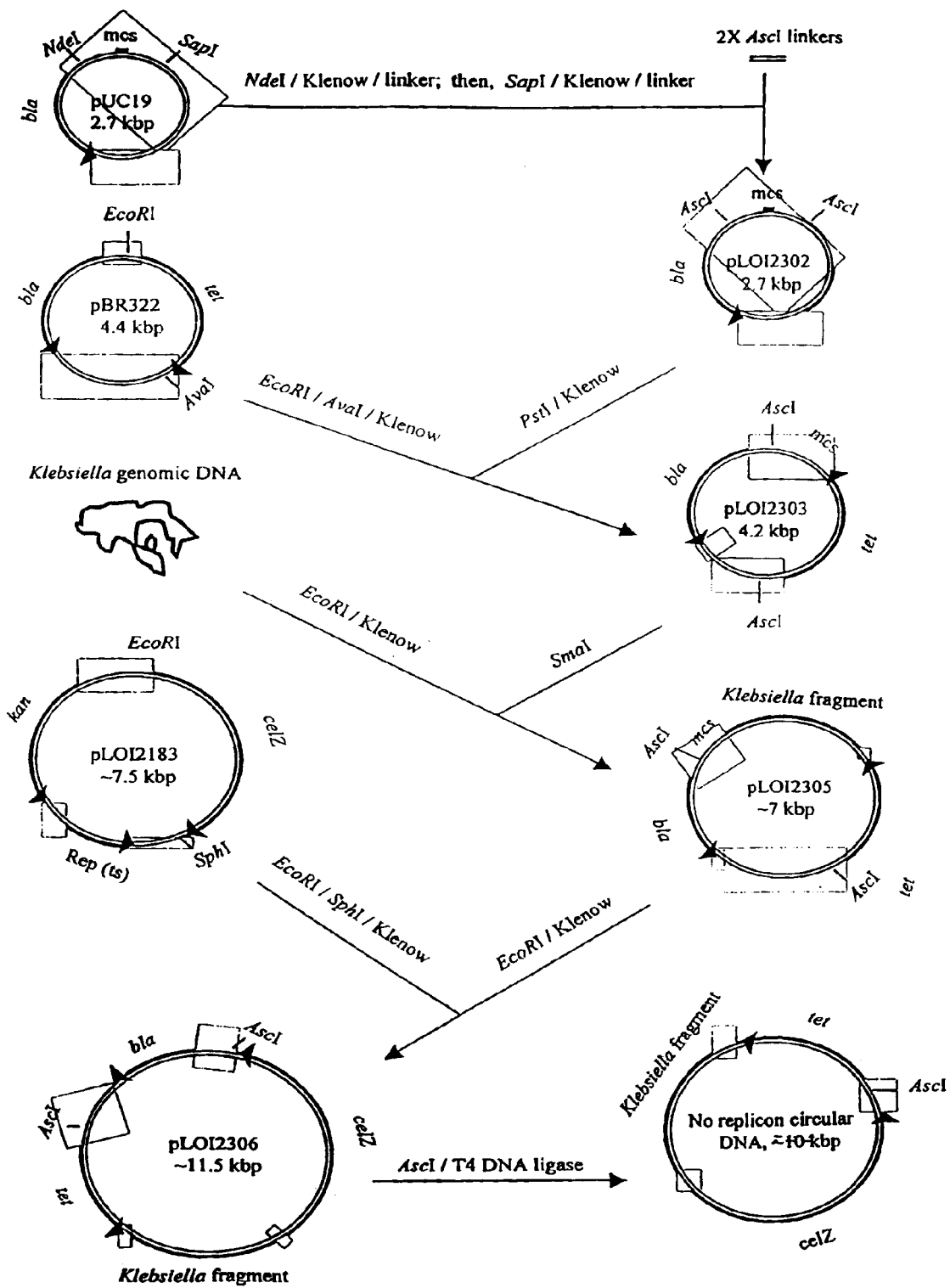
FIG. 7 shows a schematic detailing the cloning strategy used to construct the celZ integration vector pLOI2306, a genetic construct capable of being introduced into the genome of a recombinant host and conferring stable glucanase expression activity to the host.

For plasmid construction, cloning, and transformations, standard methods and E. coli DH5α hosts were used (Ausubel et al. (1987) Current Protocols in Molecular Biology. John Wiley & Sons, Inc.; Sambrook et al., (1989) Molecular Cloning: A Laboratory Manual, C.S.H.L., Cold Spring Harbor, N.Y.). Construction of the celZ integration vector, pLOI2306, was performed as shown in FIG. 7. A circular DNA fragment lacking a replicon from pLOI2306 (see FIG. 7) was electroporated into the ethanologenic K. oxytoca P2 using a Bio-Rad Gene Pulser using the following conditions: 2.5 kV and 25 μF with a measured time constant of 3.8–4.0 msec (Comaduran et al. (1998) Biotechnol. Lett. 20:489–493). The E. chrysanthemi EC 16 secretion system (pCPP2006) was conjugated into K. oxytoca using pRK2013 for mobilization (Murata et al. (1990) J. Bacteriol. 172:2970–2978). Small scale and large scale plasmid isolations were performed using the TELT procedure and a Promega Wizard Kit, respectively. DNA fragments were isolated from gels using a Qiaquick® Gel Extraction Kit from Qiagen® (Qiagen Inc., Chatsworth, Calif.). Chromosomal DNA from K. oxytoca M5A1 and Z. mobilis CP4 were isolated as described by Cutting and Yomano (see Example 1). The DNAs of interest were sequenced using a LI-COR Model 4000-L DNA sequencer (Wood et al. (1997) Biotech. Bioeng. 55:547–555).

Chromosomal Integration of celZ

Two approaches were employed for chromosomal integration of celZ, using selection with a temperature-conditional plasmid (pLOI2183) using a procedure previously described for E. coli (Hamilton et al., (1989) J. Bacteriol. 171:4617–4622) and direct integration of circular DNA fragments lacking a functional replicon. This same method was employed for chromosomal integration of Z. mobilis genes encoding the ethanol pathway in E. coli B (Ohta K et al., (1991) Appl. Environ. Microbiol. 57:893–900) and K. oxytoca M5A1 (Wood et al. (1992) Appl. Environ. Microbiol. 58:2103–2110). Typically, circular DNA was transformed into P2 by electroporation using a Bio-Rad Gene Pulser. Next, transformants were selected on solid medium containing tetracycline (6 mg L$^{-1}$) and grown on CMC plates to determine levels of glucanase activity.

Glucanase Activity

Glucanase activity resulting from expression of celZ gene product (i.e., glucanase) under the control of different test promoters was evaluated by staining CMC plates as described in Example 1. This colorimetric assay results in yellow zones indicating glucanase activity and the diameter of the zone was used as a relative measure of celZ polypeptide expression. Clones that exhibited the largest zones of yellow color were further evaluated for glucanase activity at 35° C. using carboxymethyl cellulose as the substrate (20 g L$^{-1}$ dissolved in 50 mM citrate buffer, pH 5.2) (Wood et al. (1988) *Methods in Enzymology* 160: 87–112). In order to measure the amount of intracellular glucanase, enzymatic activity was released from cultures by treatment with ultrasound for 4 seconds (Model W-290F cell disruptor, Heat System-Ultrasonics Inc., Plainview, N.Y.). The amount of glucanase activity expressed was measured and is presented here as µmol of reducing sugar released per min (IU). Reducing sugar was measured as described by Wood (Wood et al. (1988) *Methods in Enzymology* 160: 87–112) using a glucose standard.

Substrate Depolymerization

To further determine the amount of glucanase activity produced by various host cells, different carbohydrate substrates (20 g L$^{-1}$ suspended in 50 mM citrate buffer, pH 5.2) were incubated with various cell extracts. In one example, test substrates comprising acid-swollen and ball-milled cellulose were prepared as described by Wood (Wood et al. (1988) *Methods in Enzymology* 160: 87–112). A typical polysaccharase extract (i.e., EGZ (glucanase) from *K. oxytoca* SZ6 (pCPP2006)) was prepared by cultivating the host cells at 30° C. for 16 h in LB supplemented with sorbitol, a nonreducing sugar. Dilutions of cell-free broth were added to substrates and incubated at 35° C. for 16 h. Several drops of chloroform were added to prevent the growth of adventitious contaminants during incubation. Samples were removed before and after incubation to measure reducing sugars by the DNS method (see, Wood et al. (1988) *Methods in Enzymology* 160: 87–112). The degree of polymerization (DP) was estimated by dividing the total calculated sugar residues present in the polymer by the number of reducing ends.

Fermentation Conditions

Fermentations were carried out in 250 ml flasks containing 100 ml of Luria broth supplemented with 50 g L$^{-1}$ of carbohydrate. Test carbohydrates were sterilized separately and added after cooling. To minimize substrate changes, acid-swollen cellulose, ball-milled cellulose and xylan were not autoclaved. The antibiotic chloramphenicol (200 mg L$^{-1}$) was added to prevent the growth of contaminating organisms. Flasks were inoculated (10% v/v) with 24-h broth cultures (50 g L$^{-1}$ glucose) and incubated at 35° C. with agitation (100 rpm) for 24–96 h. To monitor cultures, samples were removed daily to determine the ethanol concentrations by gas chromatography (Dombek et al. (1986) *Appl. Environ. Microbiol.* 52:975–981).

Methods for Isolating and Identifying a Surrogate Promoter

In order to identify random fragments of *Z. mobilis* that would serve as surrogate promoters for the expression of heterologous genes in *Klebsiella* and other host cells, a vector for the efficient cloning of candidate promoters was constructed as described in Example 1 (see also, Ingram et al. (1988) *Appl. Environ. Microbiol.* 54:397–404).

Next, Sau3AI digested *Z. mobilis* DNA fragments were ligated into the BamHI site of pLOI2171 to generate a library of potential promoters. These plasmids were transformed into *E. coli* DH5α for initial screening. Of the 18,000 colonies individually tested on CMC plates, 75 clones produced larger yellow zones than the control (pLOI2173). Plasmids from these 75 clones were then transformed into *K. oxytoca* M5A1, re-tested, and found to express high levels of celZ in this second host.

Recombinant *Klebsiella* Hosts for Producing Polysaccharase

The high expressing clones (pLOI2177 to pLOI2194) with the largest zones on CMC plates indicating celZ expression were grown in LB broth and assayed for glucanase activity (Table 5).

TABLE 5

Evaluation of promoters for celZ expression and secretion in *K. oxytoca* M5A1

| Plasmids[a] | No secretion genes | | Secretion genes present (pCPP2006) | |
|---|---|---|---|---|
| | Total activity (IU L$^{-1}$)[b] | Secreted activity (IU L$^{-1}$) | Total activity (IU L$^{-1}$) | Secreted activity (IU L$^{-1}$) |
| PLOI2173 | 2,450 | 465 | 3,190 | 1,530 |
| PLOI2177 | 19,700 | 3,150 | 32,500 | 13,300 |
| PLOI2178 | 15,500 | 2,320 | 21,300 | 11,500 |
| PLOI2179 | 15,400 | 2,310 | 21,400 | 12,000 |
| PLOI2180 | 21,400 | 3,210 | 30,800 | 13,600 |
| PLOI2181 | 15,600 | 2,490 | 21,000 | 11,800 |
| PLOI2182 | 19,600 | 3,130 | 31,100 | 14,000 |
| PLOI2183 | 20,700 | 3,320 | 32,000 | 14,000 |
| PLOI2184 | 15,500 | 2,480 | 21,200 | 11,900 |
| PLOI2185 | 15,100 | 2,420 | 24,600 | 11,500 |
| PLOI2186 | 17,000 | 2,380 | 25,700 | 13,400 |
| PLOI2187 | 15,800 | 2,210 | 24,500 | 12,200 |
| PLOI2188 | 18,200 | 2,180 | 25,600 | 12,000 |
| PLOI2189 | 14,800 | 2,360 | 27,100 | 12,700 |
| PLOI2190 | 16,100 | 2,410 | 26,500 | 12,500 |
| PLOI2191 | 15,800 | 2,210 | 25,000 | 12,400 |
| PLOI2192 | 15,100 | 1,810 | 24,900 | 12,500 |
| PLOI2193 | 16,700 | 2,010 | 24,600 | 12,800 |
| PLOI2194 | 15,400 | 2,770 | 21,500 | 11,900 |

[a]pLOI2173 contains the celZ gene with the original promoter, all others contain the celZ gene with a *Z. mobilis* DNA fragment which serves as a surrogate promoter.
[b]Glucanase (CMCase) activities were determined after 16 h of growth at 30° C.

Activities with these plasmids were up to 8-fold higher than with the control plasmid containing the native celZ promoter (pLOI2173). The four plasmids which produced the largest zones (pLOI2177, pLOI2180, pLOI2182 and pLOI2183) also produced the highest total glucanase activities (approximately 30,000 IU L$^{-1}$). One of these plasmids, pLOI2183, was selected for chromosomal integration.

Chromosomal Integration of a Polysaccharase Gene

To stably incorporate a desirable polysaccharase gene into a suitable host cell, e.g., *Klebsiella* P2 strain, a novel vector (pLOI2306) was constructed to facilitate the isolation of a DNA fragment which lacked all replication functions but contained the celZ gene with surrogate promoter, a selectable marker, and a homologous DNA fragment for integration (FIG. 7). Two AscI sites were added to pUC19 by inserting a linker (GGCGCGCC; SEQ ID NO: 11) into Klenow-treated NdeI and SapI sites which flank the polylinker region to produce pLOI2302. A blunt fragment containing the tet resistance marker gene from pBR322 (excised with EcoRI and AvaI, followed by Klenow treatment) was cloned into the PstI site of pLOI2302 (cut with PstI, followed by Klenow treatment) to produce pLOI2303. To this plasmid was ligated a blunt fragment of *K. oxytoca* M5A1 chromosomal DNA (cut with EcoRI and made blunt with Klenow treatment) into the SmaI site of pLOI2303 to produce (pLOI2305). The EcoRI-SphI fragment (Klenow treated) containing the surrogate *Z. mobilis* promoter and celZ gene from pLOI2183 was ligated into the EcoRI site of pLOI2305 (EcoRI, Klenow treatment) to produce pLOI2306. Digestion of pLOI2306 with AscI produced two fragments, the larger of which contained the celZ gene with a surrogate promoter, tet gene, and chromosomal DNA fragment for homologous recombination. This larger fragment (10 kbp) was purified by agarose gel electrophoresis, circularized by self-ligation, and electroporated into the *Klebsiella* strain P2 and subsequently grown under selection for tetracycline resistance. The resulting 21 tetracycline-resistant colonies were purified and tested on CMC plates for glucanase activity. All were positive with large zones indicating functional expression of the celZ gene product.

Clones used to produce the recombinant strains were tested for the presence of unwanted plasmids by transforming DH5α with plasmid DNA preparations and by gel electrophoresis. No transformants were obtained with 12 clones tested. However, two of these strains were subsequently found to contain large plasmid bands which may contain celZ and these were discarded. Both strains with large plasmids contained DNA, which could be sequenced with T7 and M13 primers confirming the presence of multicopy plasmids. The remaining ten strains contain integrated celZ genes and could not be sequenced with either primer.

Figure 8:
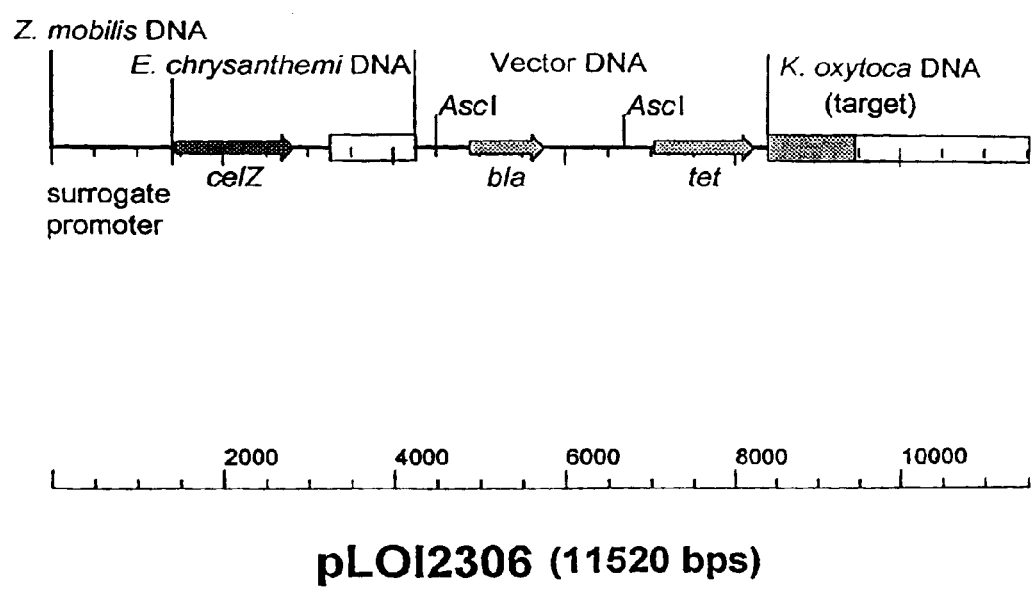
FIG. 8 shows a schematic representation of the celZ integration vector pLOI2306 (SEQ ID NO: 12) with the locations of the surrogate promoter from Z. mobilis, the celZ gene from E. chrysanthemi, resistance markers (bla and tet), and K. oxytoca target sequence indicated.

The structural features of the novel vector pLOI2306 are schematically shown in FIG. 8 and the nucleotide sequence of the vector, including various coding regions (i.e., of the genes celZ, bla, and tet), are indicated in SEQ ID NO: 12 of the sequence listing (the amino acid sequences are disclosed as SEQ ID NOS 22–24). Nucleotide base pairs 3282–4281, which represent non-coding sequence downstream of the celZ gene (obtained from *E. chrysanthemi*), and base pairs 9476–11544 which represent a portion of the non-coding target sequence obtained from *K. oxytoca* M5A1, remain to be sequenced using standard techniques (e.g., as described in Sambrook, J. et al., *T. Molecular Cloning: A Laboratory Manual*. 2nd, ed., Cold Spring Harbor Laboratory, Cold Spring Harbor Laboratory Press, Cold Spring Harbor, N.Y., (1989); *Current Protocols in Molecular Biology*, eds. Ausubel et al., John Wiley & Sons (1992)). For example, sufficient flanking sequence on either side of the aforementioned unsequenced regions of the pLOI2306 plasmid is provided such that sequencing primers that correspond to these known sequences can be synthesized and used to carry out standard sequencing reactions using the pLOI2306 plasmid as a template.

Alternatively, it will be understood by the skilled artisan that these unsequenced regions can also be determined even in the absence of the pLOI2306 plasmid for use as a template. For example, the remaining celZ sequence can be determined by using the sequence provided herein (e.g., nucleotides 1452–2735 of SEQ ID NO: 12) for synthesizing probes and primers for, respectively, isolating a celZ containing clone from a library comprising *E. chrysanthemi* sequences and sequencing the isolated clone using a standard DNA sequencing reaction. Similarly, the remaining target sequence can be determined by using the sequence provided herein (e.g., nucleotides 8426–9475 of SEQ ID NO: 12) for synthesizing probes and primers for, respectively, isolating a clone containing target sequence from a library comprising *K. oxytoca* M5A1 EcoRI fragments (e.g., of the appropriate size) and sequencing the isolated clone using a standard DNA sequencing reaction (a source of *K. oxytoca* M5A1 would be, e.g., ATCC 68564 cured free of any plasmid using standard techniques). The skilled artisan will further recognize that the making of libraries representative of the cDNA or genomic sequences of a bacterium and the isolation of a desired nucleic acid fragment from such a library (e.g., a cDNA or genomic library), are well known in the art and are typically carried out using, e.g., hybridization techniques or the polymerase chain reaction (PCR) and all of these techniques are standard in the art (see, e.g., Sambrook, J. et al., *T. Molecular Cloning: A Laboratory Manual*. 2nd, ed, Cold Spring Harbor Laboratory, Cold Spring Harbor Laboratory Press, Cold Spring Harbor, N.Y., (1989); *Current Protocols in Molecular Biology*, eds. Ausubel et al., John Wiley & Sons (1992); *Oligonucleotide Synthesis* (M. J. Gait, Ed. 1984); and *PCR Handbook Current Protocols in Nucleic Acid Chemistry*, Beaucage, Ed. John Wiley & Sons (1999) (Editor)).

Heterologous Gene Expression Using a Surrogate Promoter and Integrated or Plasmid-Based Constructs The ten integrated strains (SZ1–SZ10) were investigated for glucanase production in LB sorbitol broth (Table 6). All produced 5,000–7,000 $IUL^{-1}$ of active enzyme. Although this represents twice the activity expressed from plasmid pLOI2173 containing the native celZ promoter, the integrated strains produced only ⅓ the glucanase activity achieved by P2 (pLOI2183) containing the same surrogate *Z. mobilis* promoter (Table 5). The reduction in glucanase expression upon integration may be attributed to a decrease in copy number (i.e., multiple copy plasmid versus a single integrated copy).

Secretion of Glucanase EGZ

*K. oxytoca* contains a native Type II secretion system for pullulanase secretion (Pugsley (1993) *Microbiol. Rev.* 57:50–108), analogous to the secretion system encoded by the out genes in *Erwinia chrysanthemi* which secrete pectate lyases and glucanase (EGZ) (Barras et al. (1994) *Annu. Rev. Phytopathol*. 32:201–234; He et al. (1991) *Proc. Natl. Acad. Sci. USA*. 88: 1079–1083). Type II secretion systems are typically very specific and function poorly with heterologous proteins (He et al. (1991) *Proc. Natl. Acad. Sci. USA*. 88: 1079–1083; Py et al. (1991) *FEMS Microbiol. Lett.* 79:315–322; Sauvonnet et al. (1996) *Mol. Microbiol*. 22: 1–7). Thus as expected, recombinant celZ was expressed primarily as a cell associated product with either M5A1 (Table 5) or P2 (Table 6) as the host. About ¼ (12–26%) of the total recombinant EGZ activity was recovered in the broth. With *E. coli* DH5α, about 8–12% of the total extracellular EGZ was present. Thus the native secretion system in *K. oxytoca* may facilitate partial secretion of recombinant EGZ.

To further improve secretion of the desired products, type II secretion genes (out genes) from *E. chrysanthemi* EC16 were introduced (e.g., using pCPP2006) to facilitate secretion of the recombinant EGZ from strain P86021 in ethanologenic strains of *K. oxytoca* (Table 5 and Table 6). For most strains containing plasmids with celZ, addition of the out genes resulted in a 5-fold increase in extracellular EGZ and a 2-fold increase in total glucanase activity. For strains with integrated celZ, addition of the out genes resulted in a 10-fold increase in extracellular EGZ and a 4-fold increase in total glucanase activity. In both cases, the out genes facilitated secretion of approximately half the total glucanase activity. The increase in EGZ activity resulting from addition of the out genes may reflect improved folding of the secreted product in both plasmid and integrated celZ constructs. The smaller increase observed with the pUC-based derivatives may result from plasmid burden and competition for export machinery during the production of periplasmic β-lactamase from the bla gene on this high copy plasmid.

Two criteria were used to identify the best integrated strains of P2, growth on solid medium containing high levels of chloramphenicol (a marker for high level expression of the upstream pdc and adhB genes) and effective secretion of glucanase with the out genes. Two recombinant strains were selected for further study, SZ2 and SZ6. Both produced 24,000 IU L-1 of glucanase activity, equivalent to approximately 5% of the total cellular protein (Py et al. (1991) *Protein Engin.* 4:325–333).

Substrate Depolymerization

The substrate depolymerization of the recombinant EGZ was determined to be excellent when applied to a CMC source (Table 7). When applied to acid swollen cellulose, the activity of the glucanase was less than 10% of the activity measured for CMC activity. Little activity was noted when the polysaccharase was applied to Avicel® or xylan. However, when allowed to digest overnight, the EGZ polysaccharase resulted in a measurable reduction in average polymer length for all substrates. CMC and acid-swollen cellulose were depolymerized to an average length of 7 sugar residues. These cellulose polymers of 7 residues are marginally soluble and, ideally, may be further digested for efficient metabolization (Wood et al. (1992) *Appl. Environ. Microbiol.* 58:2103–2110). The average chain length of ball-milled cellulose and Avicel® was reduced to ⅓ of the original length while less than a single cut was observed per xylan polymer.

TABLE 6

Comparison of culture growth, glucanase production, and secretion from ethanologenic *K. oxytoca* strains containing integrated celZ

| | Growth on solid medium | Glucanase production and secretion (IU U$^{-1}$) | | | |
|---|---|---|---|---|---|
| | | No secretion system | | Adding secretion system (pCPP2006) | |
| Strains | (600 mg L$^{-1}$ CM) | Total activity | Secreted activity | Total activity | Secreted activity |
| P2 | ++++ | 0 | 0 | 0 | 0 |
| SZ1 | ++ | 6,140 | 1,600 | 26,100 | 14,300 |
| SZ2 | ++++ | 6,460 | 1,160 | 23,700 | 11,400 |
| SZ3 | +++ | 5,260 | 1,320 | 18,400 | 8,440 |
| SZ4 | +++ | 7,120 | 1,070 | 23,200 | 9,990 |
| SZ5 | + | 6,000 | 1,080 | 29,300 | 15,500 |
| SZ6 | ++++ | 7,620 | 1,520 | 24,300 | 11,900 |
| SZ7 | + | 6,650 | 1,330 | 28,800 | 15,500 |
| SZ8 | +++ | 7,120 | 854 | 28,700 | 14,900 |
| SZ9 | ++ | 7,530 | 1,130 | 26,700 | 12,800 |
| SZ10 | +++ | 4,940 | 939 | 17,000 | 6,600 |

Glucanase (CMCase) activities were determined after 16 h of growth at 30° C.

TABLE 7

Depolymerization of various substrates by EGZ from cell free broth of strain SZ6 (pCPP2006)

| | | Estimated degree of polymerization | |
|---|---|---|---|
| Substrates | Enzyme activity (IU/L) | Before digestion | After digestion |
| Carboxymethyl cellulose | 13,175 | 224 | 7 |
| Acid-Swollen cellulose | 893 | 87 | 7 |
| Ball-milled cellulose | 200 | 97 | 28 |

TABLE 7-continued

Depolymerization of various substrates by EGZ from cell free broth of strain SZ6 (pCPP2006)

| | | Estimated degree of polymerization | |
|---|---|---|---|
| Substrates | Enzyme activity (IU/L) | Before digestion | After digestion |
| Avicel ® | 41 | 104 | 35 |
| Xylan from oat spelts | 157 | 110 | 78 |

Strain SZ6 (pCPP2006) was grown in LB-sorbitol broth for 16 h as a source of secreted EGZ.

Saccharifcation and Fermentation Ability of a Biocatalyst

To be useful, addition of celZ and out genes to strain P2 must not reduce the fermentative ability of the resulting biocatalyst. A comparison was made using glucose and cellobiose (Table 8). All strains were equivalent in their ability to ferment these sugars indicating a lack of detrimental effects from the integration of celZ or addition of pCPP2006. These strains were also examined for their ability to convert acid-swollen cellulose directly into ethanol. The most active construct SZ6 (pCPP2006) produced a small amount of ethanol (3.9 g L$^{-1}$) from amorphous cellulose. Approximately 1.5 g L$^{-1}$ ethanol was present initially at the time of inoculation for all strains. This decreased with time to zero for all strains except SZ6 (pCPP2006). Thus the production of 3.9 g L$^{-1}$ ethanol observed with SZ6 (pCPP2006) may represent an underestimate of total ethanol production. However, at best, this represents conversion of only a fraction of the polymer present. It is likely that low levels of glucose, cellobiose, and cellotriose were produced by EGZ hydrolysis of acid swollen cellulose and fermented. These compounds can be metabolized by the native phosphoenolpyruvate-dependent phosphotransferase system in *K. oxytoca* (Ohta K et al., (1991) *Appl. Environ. Microbiol.* 57:893–900; Wood et al. (1992) *Appl. Environ. Microbiol.* 58:2103–2110).

TABLE 8

Ethanol production by strain SZ6 containing out genes (pCPP2006) and integrated celZ using various substrates (50 g L$^{-1}$)

| | Ethanol production (g L$^{-1}$) | | |
|---|---|---|---|
| Strains | Glucose | Cellobiose | Acid-swollen cellulose |
| P2 | 22.9 | 22.7 | 0 |
| P2 (pCPP2006) | 22.6 | 21.3 | 0 |
| SZ6 | 21.5 | 19.7 | 0 |
| SZ6 (pCPP2006) | 22.7 | 21.2 | 3.9 |

Initial ethanol concentrations at the time of inoculation were approximately 1.5 g L$^{-1}$ for all cultures. With acid swollen cellulose as a substrate, these levels declined to 0 after 72 h of incubation for all strains except SZ6 (pCP206).

EXAMPLE 3

Synergistic Hydrolysis of Carboxymethyl Cellulose and Acid-swollen Cellulose by Two Endoglucanases (EGZ and EGY) from *Erwinia chrysanthemi*

This example describes production of the endoglucanases EGY and EGZ by recombinant *E. coli* and the synergistic hydrolysis of carboxymethyl cellulose (CMC) and acid-swollen cellulose by these endoglucanases.

Throughout this example, the following materials and methods are used unless otherwise stated.

Materials and Methods
Bacteria, Plasmids and Culture Conditions

Bacterial strains and plasmids used in this study are listed in Table 9.

TABLE 9

Strains and plasmids used

| Strains/Plasmids | Descriptions | References/Sources |
|---|---|---|
| Strains | | |
| *Escherichia coli* | | |
| DH5α | lacZ M15 recA | Bethesda Research Laboratory |
| B | Prototrophic | ATCC11303 |
| HB101 | recA lacY recA | ATCC37159 |
| TOP10F' | This strain expresses the lac repressor (lacI$^q$ gene) from an F episome | Invitrogen |
| Plasmids | | |
| pCR2.1-TOPO | TOPO ™ TA Cloning vector, Ap$^r$, Km$^r$ | Invitrogen |
| pRK2013 | Km$^r$ mobilizing helper plasmid (mob$^+$) | ATCC |
| pCPP2006 | Sp$^r$, ca. 40 kbp plasmid carrying the complete out genes from *E. chrysanthemi* EC16 | He, et al. (1991) Proc. Natl. Acad Sci. USA 88: 1079–1083. |
| pLOI1620 | Ap$^r$, celZ gene and its native promoter from *E. chrysanthemi* P86021 | Beall, et al. (1993) J. Indust. Microbiol. 11: 151–155. |
| pMH18 | Ap$^r$, celY gene and its native promoter from *E. chrysanthemi* 3937 | Guiseppi, et al (1991) Gene 106: 109–114. |
| pLOI2311 | celY gene (without native promoter), cloned into pCR2.1-TOPO vector and oriented for expression from the lac promoter | See text |

*Escherichia coli* DH5α and TOPO10F' were used as hosts for plasmid constructions.

The celZ gene was cloned from *E. chrysanthemi* P86021 (Beall, et al. (1993) *J. Indust. Microbiol.* 11:151–155). The celY gene was cloned by Guiseppi et al. ((1991) *Gene* 106:109–114) from *E. chrysanthemi* 3937. The out genes were cloned by He et al. ((1991) *Proc. Acad. Sci. USA* 88:1079–1083) from *E. chrysanthemi* EC16.

*E. coli* cultures were grown at 37° C. in Luria-Bertani broth (LB) containing per liter: 10 g Difco tryptone, 5 g Difco® yeast extract, and 5 g sodium chloride or on solid LB medium containing agar (1.5%). Clones were screened for endoglucanase production using the Congo Red method (Wood, et al. (1989) *Biochem. J.* 260:37–43). Indicator plates were prepared by supplementing LB agar with low viscosity CMC (0.3%). Ampicillin (50 µg/ml), kanamycin (50 µg/ml) and spectinomycin (100 µg/ml) were added as appropriate for selection.

Genetic Methods

Standard methods were used for plasmid construction and analyses (Ausubel, et al. (1987) *Current Protocols in Molecular Biology*. New York: John Wiley and Sons, Inc). The coding region for celY was amplified by the polymerase chain reaction using pMH18 as the template with the following primer pairs: N-terminus 5' CTGTTCCGTTAC-CAACAC3 (SEQ ID NO:13)', C-terminus 5'GTGAATGG-GATCACGAGT3' (SEQ ID NO:14). The *E. chrysanthemi* out genes (pCPP2006) were transferred by conjugation using pRK2013 for mobilization (Zhou, et al. (1999) *B. Appl. Environ. Microbiol.* 65:2439–2445). DNA was sequenced by the dideoxy method using a LI-COR Model 4000-L DNA sequencer and fluorescent primers.

Enzyme Assay

Endoglucanase activity was determined in vitro using CMC as a substrate. Appropriate dilutions of cell-free culture broth (extracellular activity) or broth containing cells that had been disrupted by ultrasound (total activity) were assayed at 35° C. in 50 mM citrate buffer (pH 5.2) containing low viscosity CMC (20 g per liter). Reactions were terminated by heating in a boiling water bath for 10 min. Reducing sugars were measured using 3,5-dinitrosalicylic acid reagent with glucose as a standard (Wood, et al. (1988) *Methods Enzymology* 160:87–112). Enzyme activity (CMCase) is expressed as µmol reducing sugar released per min (IU). Results are an average of two or more determinations.

Synergism

Stationary phase cultures of DH5α(pLOI1620+pCPP2006) and DH5α(pLOI2311) were sonicated and centrifuged as described in Zhou, et al. (1999), supra, as a source of EGZ and EGY, respectively. These were diluted as necessary to provide equal CMCase activities. Mixtures of EGZ and EGY were tested for synergy at 35° C. in 50 mM citrate buffer (pH5.2) containing CMC (20 g/L) or acid swollen cellulose (20 g per liter). For tests with Avicel® (20 g per liter), enzyme preparations were mixed without prior dilution. Hydrolyzed samples of acid-swollen cellulose and Avicel® were centrifuged (10,000× g, 5 min) to remove insoluble material prior to the determination of reducing sugars.

The effect of sequential additions of EGZ and EGY was also investigated. Substrates were hydrolyzed with a single enzyme for 4 hours and then inactivated by boiling for 20 minutes. After cooling, the second enzyme was added and incubated for an additional 4 hours. Control experiments were conducted with both enzymes together (4 hours) and with each enzyme alone (4 hours). Samples were analyzed for reducing sugar. In some cases, products were also analyzed by thin layer chromatography.

The degree of synergism for enzyme mixtures was calculated as the observed activity divided by the sum of predicted contributions from EGY alone and EGZ alone (Riedel, et al. (1997) *FEMS Microbiol. Lett.* 147:239–243).

Hydrolysis of Cellooligosaccharides

Hydrolysis products from cellobiose, cellotriose, cellotetraose, cellopentaose, acid-swollen cellulose (Wood, et al. (1988), supra) and Avicel® were analyzed by thin layer chromatography. For these analyses, 15 μl of 1% substrate was mixed with 45 μl of crude enzyme (0.07 IU), incubated at 35° C. for 2 hours and terminated by heating in a boiling water bath. Hydrolysates were spotted on Whatman 250 μm Silica-gel 150A plates and developed for approximately 4 hours using the solvent system described by Kim, (1995) Appl. Environ. Microbiol. 61:959–965). By volume, this solvent contained 6 parts chloroform, 7 parts acetic acid, and 1 part water. Sugars were visualized by spraying of 6.5 mM N-(1-naphthyl) ethylenediamine dihydrochloride and heating at 100° C. for approximately 10 min (Bounias, (1980) Anal. Biochem. 106:291–295).

Materials and Chemicals

Tryptone and yeast extract were products of Difco (Detroit, Michigan). Antibiotics, low viscosity CMC, cellobiose, cellotriose, and cellotetraose were obtained from the Sigma Chemical Company (St. Louis, Mo.). Cellopentaose was obtained from V-Lab (Covington, La.). Avicel® was purchased from Fluka Chemika (Buchs, Switzerland).

Production of EGY and EGZ by Recombinant E. coli

Low levels of EGY activity were produced by native E. chrysanthemi 3937 and by recombinant E. coli harboring plasmid pMH18 (Boyer, et al. ((1987) Eur. J. Biochem. 162:311–316; Guiseppi, et al., supra). Poor expression from the high copy plasmid in E. coli was attributed to promoter function and a putative requirement for a celY activator protein (Guiseppi, et al., supra). A new clone was constructed to produce higher levels of EGY for our investigations of synergy. The EGY coding region (without promoter) was amplified using the polymerase chain reaction and cloned behind the lac promoter in pCR2.1-TOPO. The resulting plasmid, pLOI2311, was strongly positive on CMCase indicator plates. Replacement of the native promoter with the lac promoter increased celY expression by approximately 10-fold, from 165 IU/L to 1800 IU/L (See Table 10, below).

reported previously (Zhou, et al. (1999) Appl. Environ. Microbiol. 65:2439–2445). Unlike EGZ, however, EGY activity was not affected by the presence of out genes. Maximal EGY and EGZ activities were obtained from 24-hour cultures.

The supernatants from disrupted cultures of DH5α containing pLOI2311 or pLOI1620 and pCPP2006 (out genes) were used as a source of EGY and EGZ, respectively, for further investigations.

Synergistic Action of EGY and EGZ with CMC as a Substrate

Figure 9:
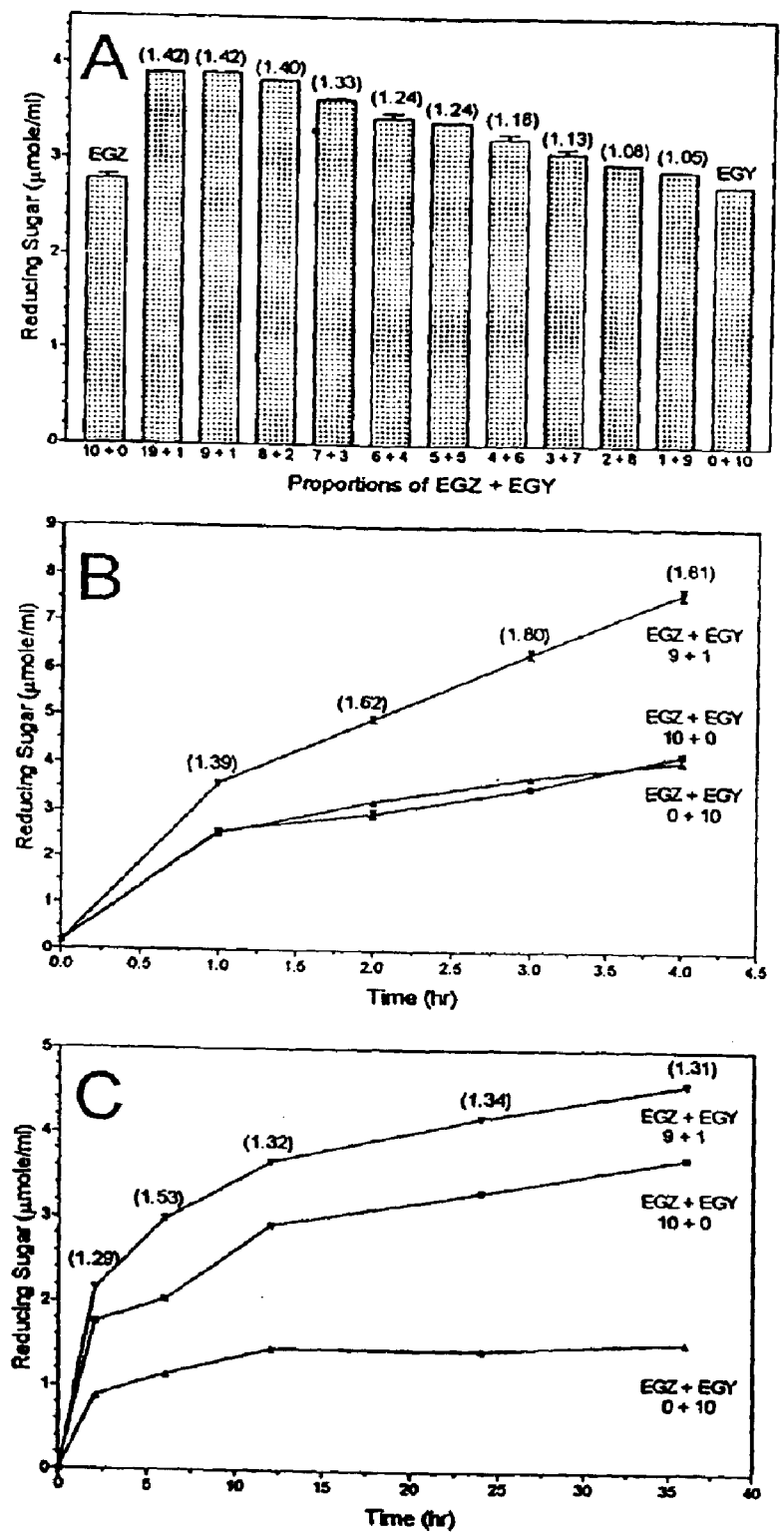
FIG. 9 shows graphical depictions of the synergistic action of EGY and EGZ. Both enzymes were diluted to equal CMCase activities (1.5 IU/ml) with calculated synergies shown in parenthesis. Panel A shows a graph depicting the effect of enzyme ratios on synergy. Different amounts of EGY and EGZ were combined to maintain a constant predicted activity (0.15 IU/ml) based on the contribution of individual enzymes. Assays were incubated with CMC for 1 hour at 35° C. and terminated by boiling. Numbers on the X axis indicate the proportions of EGZ and EGY. Synergy is shown above each bar. Panel B shows a graph depicting the hydrolysis of CMC by EGZ and EGY, alone and in combination (9 parts EGZ+1 part EGY). All assays contained equal total activities (0.15 IU/ml) based on the sum of individual EGY and EGZ activities. Synergy is shown above each point for the combination of both enzymes. Panel C shows a graph depicting the hydrolysis of acid-swollen cellulose by EGZ and EGY, alone and in combination. A 9 to 1 ratio of EGZ to EGY was used for the combined enzyme reaction. All assays contained 1.5 IU/ml based on the sum of individual EGY and EGZ activities. Synergy is shown above each point for the combination of both enzymes.

Initial studies examining the combined actions of EGY and EGZ were conducted with CMC (20 g per liter) for a single incubation time (FIG. 9). Disrupted cell preparations containing EGY and EGZ were each diluted to equal activities (CMCase) and combined in different proportions to maintain a constant sum of individual activities. EGY and EGZ were tested individually as controls. All mixtures of EGY and EGZ were significantly higher than either enzyme assayed alone indicating a synergistic interaction. The synergistic effect increased with the proportion of EGZ. Maximal synergy (1.42) was observed with a ratio of EGZ to EGY activities of 9 to 1 and 19 to 1.

Further experiments examined the effect of incubation time using CMC as the substrate and an activity ratio of 9 to 1 for EGZ and EGY, respectively (FIG. 9). EGZ and EGY alone were included as controls. The synergistic effect of combining EGZ and EGY was clearly evident as an increase in the rate and extent of hydrolysis. Calculated synergy increased with incubation time. At the end of the incubation (4 hours), the concentration of reducing sugars was 1.8-fold higher in the mixed enzyme preparation than predicted by the arithmetic sum of individual EGZ and EGY activities, i.e., synergistic activity.

Effect of Substrate (CMC) Concentration on Synergy

The effect of substrate concentration on the synergy between EGZ and EGY was also studied (See Table 11,

TABLE 10

Effect of E. chrysanthemi out genes on the expression and secretion of celY and celZ in E. coli DH5α

| Enzyme expressed | Promoter | Growth (hr) | No Out genes | | | out genes present (pCCP2006) | | |
|---|---|---|---|---|---|---|---|---|
| | | | Extracellular CMCase[a] (IU per liter) | Total CMCase (IU per liter) | Apparent secretion (%) | Extracellular CMCase[a] (IU per liter) | Total CMCase (IU per liter) | Apparent secretion (%) |
| EGY | Native promoter (pMH18) | 24 | 136 | 165 | 82 | 136 | 180 | 76 |
| | lac promoter (pLOI2311) | 8 | 208 | 266 | 78 | nd[b] | Nd | nd |
| | | 16 | 1,420 | 1,590 | 90 | nd | Nd | nd |
| | | 24 | 1,650 | 1,800 | 90 | 1,360 | 1,510 | 90 |
| EGZ | Native plus lac promoter (pLOI1620) | 8 | 130 | 1,320 | 10 | 6,710 | 7,4600 | 90 |
| | | 16 | 1,200 | 9,030 | 13 | 13,400 | 19,700 | 68 |
| | | 24 | 1,800 | 12,500 | 14 | 23,600 | 36,800 | 64 |

[a]Secreted or released CMCase activity in the culture supernatant.
[b]Abbreviation: nd, not determined.

Approximately 90% of EGY activity was found in the extracellular milieu. Expression of celZ was included for comparison (See Table 10). High levels of EGZ were produced by E. coli harboring plasmid pLOI1620. Extracellular EGZ and total EGZ activity were further increased by addition of the E. chrysanthemi out genes (pCPP2006) as below). Increasing the CMC concentration from 2.5 g per liter to 20 g per liter increased the observed synergy from 1.12 to 1.89. Based on the specific activities of EGZ and EGY and a maximal synergism of 1.89, the enzyme turnover rate for the combination was 8-fold that of purified EGY alone, and 1.5-fold that of purified EGZ alone.

TABLE 11

Effect of substrate concentration on synergy

| CMC Substrate (g/L) | Reducing sugar released (μmole/ml)[a] | | | |
|---|---|---|---|---|
| | EGZ (10)[b] | EGY (10)[b] | EGZ (9) + EGY (1)[b] | Synergy[a,c] |
| 20 | 3.98 ± 0.04 | 3.83 ± 0.04 | 7.51 ± 0.07 | 1.89 ± 0.02 |
| 10 | 4.53 ± 0.01 | 2.91 ± 0.07 | 5.38 ± 0.04 | 1.25 ± 0.01 |
| 5.0 | 2.87 ± 0.01 | 1.18 ± 0.04 | 2.92 ± 0.04 | 1.08 ± 0.02 |
| 2.5 | 1.42 ± 0.01 | 0.50 ± 0.04 | 1.49 ± 0.01 | 1.12 ± 0.01 |

[a]Average ± standard deviation.
[b]EGZ and EGY were diluted to equal CMCase activities. Reactions (0.15 IU/ml) contained 9 parts of EGZ and 1 part of EGY. As controls, EGZ (0.15 IU/ml) and EGY (0.15 IU/ml) were each tested individually.
[c]Synergy was calculated as the observed activity divided by the sum of predicted contributions from EGY alone (10%) plus EGZ alone (90%).

EGY was more sensitive to substrate concentration than EGZ. Increasing the CMC concentration resulted in an 8-fold increase in reducing sugar products with EGY but only a 3-fold increase with EGZ. Based on a double reciprocal plot of the data in Table 11, apparent Km values of 104, 12, and 38 g per liter were estimated for EGY, EGZ and the combination of both enzymes (9 parts EGZ+1 part EGY), respectively. The higher apparent Km for EGY is consistent with a requirement for longer substrate molecules.

The extent of CMC hydrolysis was also examined by determining the approximate size of hydrolysis products. CMC (1.25 g per liter) was incubated (4 hours, 0.75 IU CMCase/ml) with EGY, EGZ, and a combination of both enzymes (9 parts EGZ plus 1 part EGY). Chain length was estimated based on the reducing sugar assay before (250 glucosyl units) and after incubation. The average chain length was substantially reduced by all three enzyme preparations. EGZ was more effective in reducing chain length than EGY, 3.6 versus 10.7 glucosyl residues, respectively. The combination of both enzymes resulted in a synergistic action. Simultaneous hydrolysis with both enzymes reduced the average size of the hydrolysis products to 2.3 glucosyl residues, 36% lower than EGZ alone and 79% lower than EGY alone. These results confirm that EGZ readily hydrolyzes both large CMC polymers and smaller saccharides. The action of EGY appears more limited, primarily hydrolyzing large polymers with greater than 10 glucosyl units.

Sequential and Simultaneous Hydrolysis of CMC with EGZ and EGY

The mechanism of synergistic action between EGZ and EGY was further investigated by comparing the effects of sequential hydrolysis with individual endoglucanases to that of simultaneous hydrolysis by a mixture of both enzymes (See Table 12, below). Again synergy was observed for the simultaneous actions of both enzymes. No synergy was observed for the sequential hydrolysis of CMC when EGZ was used as the first enzyme, followed by digestion with EGY (after heat-inactivation of EGZ). In contrast, full synergy was retained when CMC was first treated with EGY, followed by EGZ (after heat-inactivation of EGY). These results indicate that synergy can be achieved by the independent activities of EGY and EGZ. Enzymatic modification of the substrate by EGY increased the rate and extent of subsequent hydrolysis by EGZ. These results provide further evidence that EGY and EGZ function quite differently. EGY appears to primarily reduce the chain length of large polymers while EGZ appears to act more randomly, hydrolyzing both large and small substrate molecules.

TABLE 12

Sequential and simultaneous hydrolysis of CMC by EGZ and EGY

| Enzyme (relative proportion)[a] | Measured reducing sugar released (μmole/ml)[b] | Predicted activity from the arithmetic sum of EGY and EGZ (μmole/ml)[c] | Synergy[b,d] |
|---|---|---|---|
| EGZ (10) + EGY (0) | 4.65 ± 0.08 | 4.65 | 1.00 ± 0.02 |
| EGZ (0) + EGY (10) | 4.14 ± 0.04 | 4.14 | 1.00 ± 0.01 |
| EGZ (9) + EGY (1). (simultaneously) | 8.28 ± 0.08 | 4.60 | 1.80 ± 0.02 |
| EGZ (9), then EGY (1). (sequential) | 4.86 ± 0.23 | 4.60 | 1.06 ± 0.05 |
| EGY (1), then EGZ (9). (sequential) | 8.75 ± 0.14 | 4.60 | 1.90 ± 0.03 |

[a]EGZ and EGY were diluted to equal CMCase activities. Both simultaneous and sequential hydrolysis reactions (0.15 IU/ml) were investigated using 9 parts of EGZ and 1 part of EGY. In the sequential hydrolysis experiments, the first enzyme was incubated with substrate for 4 hours and inactivated by boiling for 20 min. After cooling, the second enzyme was added and incubated for an additional 4 hours. All reactions were terminated by boiling.
[b]Average ± standard deviation (3 experiments).
[c]Calculated sum of individual EGY and EGZ activities.
[d]Synergy was calculated as the observed activity divided by the sum of predicted contributions from EGY alone (10%) plus EGZ alone (90%).

Synergistic Action on Acid-swollen and Crystalline Cellulose

Potential synergy was investigated using acid-swollen cellulose as the substrate and a 9 to 1 ratio of EGZ:EGY based on CMCase activities (FIG. 9). Since the activities of EGZ and EGY with acid-swollen cellulose are lower than those with CMC (Boyer, et al. (1987) Eur. J. Biochem. 162:311–316), enzyme loading (1.5 IU) and incubation times were increased. When assayed individually with acid-swollen cellulose, EGY was approximately ⅓ as active as EGZ. However, the combination of these two enzymes was significantly more active than the predicted arithmetic sum of individual activities at all time points. The degree of synergy was essentially constant (1.36±0.17) during the 36 hour period of incubation.

Figure 10:
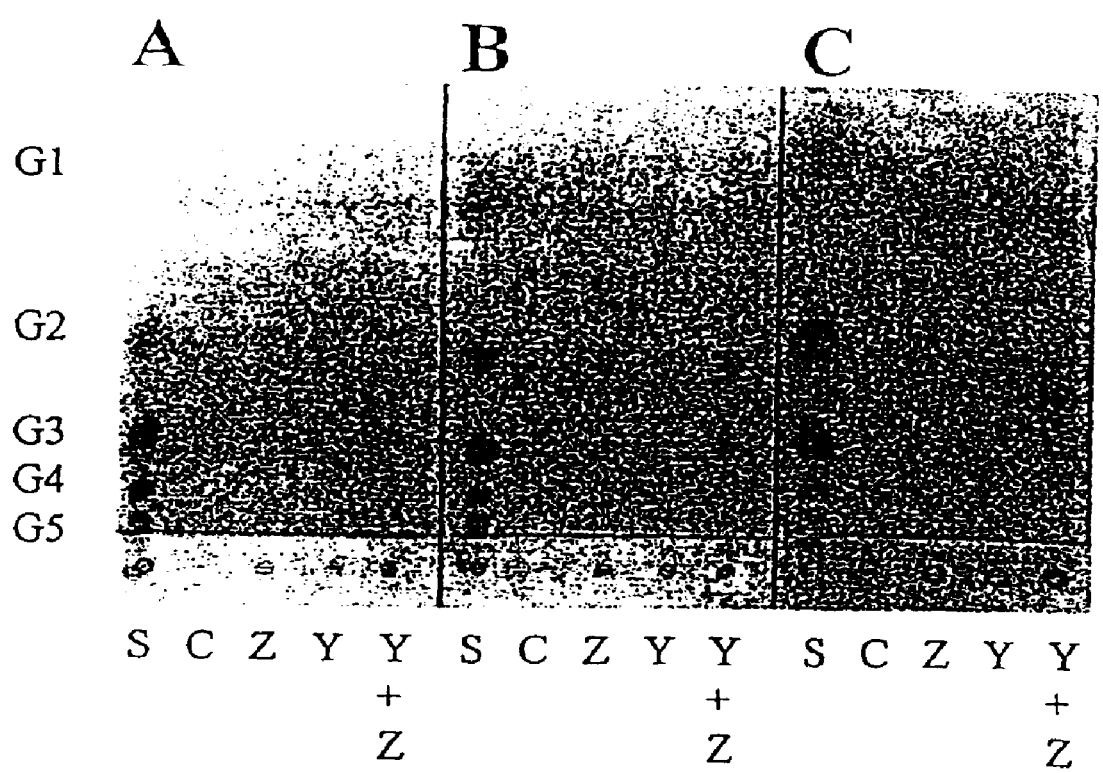
FIG. 10 represents a thin layer chromatography (TLC) analysis of the hydrolysis products from two complex sugars: acid-swollen cellulose and Avicel®. Approximately 1.5 IU and 25 IU of CMCase were used in reactions with acid-swollen cellulose and Avicel®, respectively. Abbreviations for Y axis: GI, glucose; G2, cellobiose; G3, cellotriose; G4, cellotetraose; and G5, cellopentaose. Lanes: S, mixed cellooligosaccharide standard; C, control lacking enzyme; Z, EGZ; Y, EGY, and Z+Y: EGZ+EGY. Panel A shows results with acid-swollen cellulose after a 6-hour incubation with CMCase (1 µl loading). Panel B shows results with acid-swollen cellulose after a 6-hour incubation with CMCase (2 µl loading). Panel C shows results with Avicel® after a 48-hour incubation with CMCase (10 µl loading).

The hydrolysis products from acid-swollen cellulose (6 hours) were analyzed by thin layer chromatography (FIG. 10). No soluble saccharides were observed after incubation with EGY alone. Cellobiose and cellotriose were the primary products from hydrolysis with EGZ alone and a combination of EGY and EGZ. With the combination of both enzymes, higher product levels were evident as darker and larger spots confirming a synergistic action.

The synergistic action of EGZ and EGY was also investigated with Avicel® (FIG. 10), a highly crystalline cellulose. Small amounts of cellobiose and cellotriose were observed as hydrolysis products with EGZ alone and with the mixture of EGY and EGZ. Due to low activity with Avicel®, high loadings (10 µl) were required on thin layer plates to visualize products. Note that this additional salt increased the relative migration of oligosaccharide products in comparison to the standards. No cellooligosaccharide spots were observed with EGY alone. Again synergism was evident with the combination of EGY and EGZ. Larger and more intense spots were observed corresponding to cellobiose, cellotriose, and cellotetraose with the combined activities than with EGZ alone. The low activity with Avicel® as a substrate and the relatively low levels of products are consistent with the hydrolysis of the amorphous rather than the crystalline regions of Avicel®. These results indicate that the synergistic action of EGZ and EGY is not limited to a model substrate such as CMC. Synergistic hydrolysis was also observed for acid-swollen cellulose and the amorphous regions of Avicel®.

Hydrolysis of Cellooligosaccharides

Figure 11:
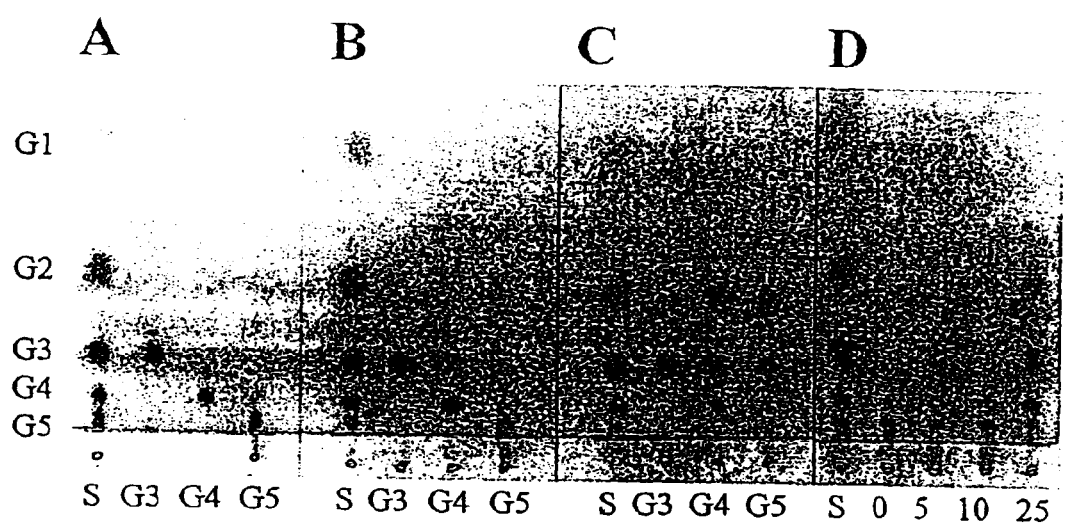
FIG. 11 represents a TLC analysis showing the hydrolysis of cellooligosaccharides by EGZ and EGY. Each test contained approximately 0.07 IU of CMCase per ml (2 hour incubation, 35° C.). Abbreviations: S, mixed cellooligosaccharides standard; G1, glucose; G2, cellobiose; G3, cellotriose; G4, cellotetraose; and G5, cellopentaose. Panel A shows the substrates before hydrolysis, Panel B shows the substrates after incubation with EGY, Panel C shows the substrates after incubation with EGZ, and Panel D shows EGZ hydrolysis of cellopentaose after different periods of incubation (0, 5, 10, and 25).
Figure 12:
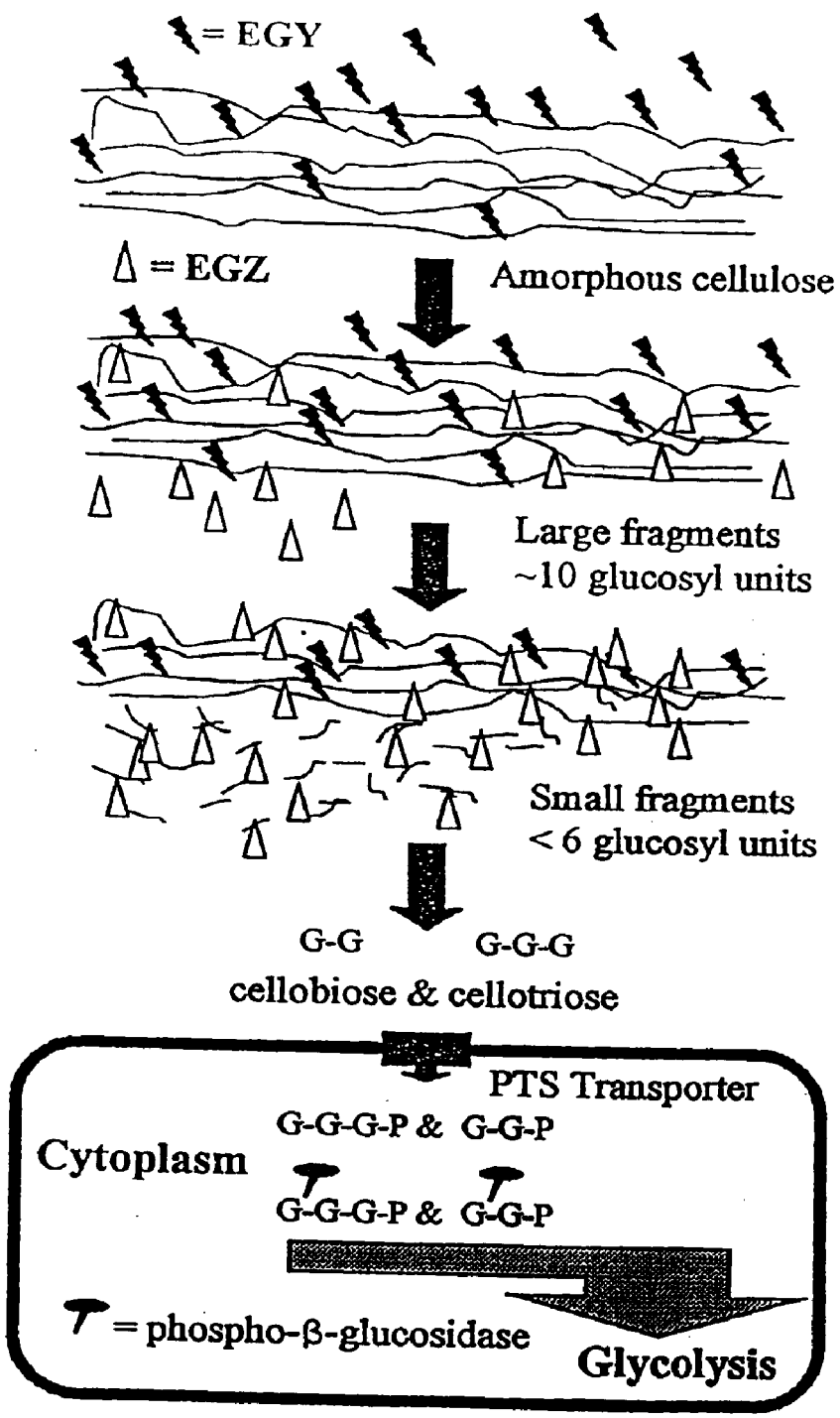
FIG. 12 is a model illustrating the utilization of amorphous cellulose by E. chrysanthemi. Three glucosidases are used for the catabolism of amorphous cellulose. Two of these, EGY and EGZ are extracellular endoglucanases, which function, together in a synergistic fashion. EGY requires large substrate molecules and hydrolyzes these into shorter, insoluble fragments. EGY does not hydrolyze soluble cellooligosaccharides (2 to 5 glucosyl residues). EGZ readily hydrolyzes soluble cellooligosaccharides (cellopentaose and cellotetraose) and amorphous fragments of intermediate length to produce cellobiose and cellotriose. Cellobiose and cellotriose are phosphorylated during cellular uptake by a phosphoenolpyruvate-dependent phosphotransferase system. Hydrolysis is completed intracellularly by a third enzyme, phospho-β-glucosidase. Resulting monomeric products (glucose and glucose-6-phosphate) are metabolized by glycolysis.

The substrate specificities of EGZ and EGY were further investigated using soluble cellooligosaccharides (cellobiose, cellotriose, cellotetraose, and cellopentaose). Hydrolysis products were analyzed by thin layer chromatography (FIG. 11). Cellobiose was not hydrolyzed by EGY, EGZ or a combination of both enzymes. None of the cellooligosaccharides was hydrolyzed by EGY alone (FIG. 11, Panel B). In contrast, EGZ hydrolyzed cellotetraose and cellopentaose but not cellotriose (FIG. 11, Panel C). EGZ hydrolysis products from cellotetraose were primarily cellobiose with lesser amounts of cellotriose and glucose. With cellopentaose as the substrate, EGZ produced approximately equal amounts of cellobiose and cellotriose indicating a preferential attack on the second or third glycosidic bond. This was further confirmed by examining samples at various times during the incubation of cellopentaose with EGZ (FIG. 11, Panel D). Cellobiose and cellotriose progressively accumulated during incubation with a corresponding reduction in cellopentaose. Thus in contrast to the requirement for large substrates by EGY, EGZ hydrolyzes soluble cellooligosaccharides containing four or more glucosyl units.

EXAMPLE 4

Integration, Expression, and Extracellular Secretion of *Erwinia chrysanthemi* Endoglucanase EGY (celY) and EGZ (celZ) in Ethanologenic *Klebsiella oxytoca* P2

In this example, the functional integration of both celY and celZ from *E. chrysanthemi* into the chromosome of *K. oxytoca* P2, is described. Also described is the synergism between recombinant EGY and EGZ and fungal cellulase (Spezyme CE®) during the fermentation of cellulose to ethanol using simultaneous saccharification and fermentation.

Throughout this example, the following materials and methods are used unless otherwise stated.

Materials and Methods

Bacteria, Plasmids and Culture Conditions

Strains and plasmids used in this example are listed in Table 13 below.

TABLE 13

Strains and Plasmids

| Strains/plasmids | Description | Sources/references |
|---|---|---|
| *E. coli* strains | | |
| DH5α | lacZ M15 recA | Bethesda Research Laboratory |
| TOP10F' | hsdR mcrA lacZΔM15 endA recA; F' tet lacI | Invitrogen |
| HB101 | recA lacY | ATCC37159 |
| S17-1 | thi pro recA hsdR RP4-2-tet::Mu aphA: Tn7 λpir | De Lorenzo, et al. (1990) J. Bacteriol. 172: 6568–6572. |
| *Z. mobilis* strain | | |
| CP4 | Prototrophic | Ingram, et al. (1999) Biotechnol. Prog. 15: 855–866. |
| *K. oxytoca* strains | | |
| M5A1 | Prototrophic | Wood, et al. (1992) Appl. Environ. Microbiol. 58: 2103–2110. |
| P2 | pfl::pdc adhB cat | Wood, et al. (1992) Appl. Environ. Microbiol. 58: 2103–2110. |
| SZ6 | pfl::pdc adhB cat; integrated celZ tet | |
| SZ12 | pfl::pdc adhB cat; integrated celZ celY kan | See text |
| SZ21 | pfl::pdc adhB cat; integrated celZ celY | See text |
| SZ22 | pfl::pdc adhB cat; integrated celY celZ::aac | See text |
| Plasmids | | |
| pUC18 | bla cloning vector | New England Biolabs |
| pUC19 | bla cloning vector | New England Biolabs |
| pCR2.1-TOPO | TA cloning vector, bla kan | Invitrogen |

TABLE 13-continued

Strains and Plasmids

| Strains/plasmids | Description | Sources/references |
|---|---|---|
| pMH18 | bla celY from *E. chrysanthemi* 3937 | Guiseppi, et al. (1991) Gene 106: 109–114. |
| pHPΩ45aaac | bla aac source of apramycin gene | Blondelet-Rouault, et al. (1997) Gene 190: 315–317. |
| pBR322 | bla tet cloning vector | New England Biolabs |
| pRK2013 | kan, mobilizing plasmid | ATCC |
| pCPP2006 | spm, Ca. 40 kbp fragment containing out genes from *E. chrysanthemi* EC16 | He, et al. (1991) Proc. Natl. Acad. Sci. USA 88: 1079–1083. |
| pFT-A | bla low copy vector containing flp recombinase gene and temperature conditional pSC101 replicon | Martinez-Morales, et al. (1999) J. Bacteriol. 181: 7143–7148. |
| pLOI2224 | kan integration vector containing conditional R6K replicon and two FRT sites | Martinez-Morales, et al. (1999) J. Bacteriol. 181: 7143–7148. |
| pLOI2307 | bla containing celZ gene and a surrogate promoter from *Z. mobilis* DNA | Zhou, et al. (1999) Appl. Environ. Microbiol. 65: 2439–2445. |
| pLOI2311 | PCR fragment containing celY gene cloned into pCR2.1-TOPO, expressed from lac promoter | Zhou, et al. (2000) J. Bacteriol. 182: 5676–5682. |
| pLOI2302 | pUC19 containing AscI linkers inserted into blunt NdeI and SapI sites | Zhou, et al. (1999) J. Indust. Microbiol. Biotechnol. 22: 600–607. |
| pLOI2316 | pUC18 containing the celY gene on a Klenow-treated EcoRI fragment from pLOI2311 inserted into a blunt HincII site, expressed from the lac promoter | See text |
| pLOI2317 | EcoRI-HindIII fragment from pLOI2316 inserted into the corresponding sites of pLOI2302 | See text |
| pLOI2318 | Sau3A1 fragment of *Z. mobilis* DNA fragment exhibiting promoter activity inserted into the BamHI site of pLOI2317 | See text |
| pLOI2319 | Sau3A1 fragment of *Z. mobilis* DNA exhibiting promoter activity inserted into the BamHI site of pLOI2317 | See text |
| pLOI2320 | Sau3A1 fragment of *Z. mobilis* DNA exhibiting promoter activity inserted into the BamHI site of pLOI2317 | See text |
| pLOI2323 | Sau3A1 fragment of *Z. mobilis* DNA exhibiting promoter activity inserted into the BamHI site of pLOI2317 | See text |
| pLOI2342 | Sau3A1 fragment of *Z. mobilis* DNA exhibiting promoter activity inserted into the BamHI site of pLOI2317 | See text |
| pLOI2348 | Random EcoRI fragment of *K. oxytoca* M5A1 DNA cloned into EcoRI site of pLOI2323 | See text |
| pLOI2349 | EcoRI linker inserted into the Klenow-treated SphI site of pLOI2307 | See text |
| pLOI2350 | EcoRI fragment (celZ and surrogate promoter) from pLOI2349 inserted into the EcoRI site of pLOI2224 | See text |
| pLOI2352 | AscI fragment (*K. oxytoca* fragment, *Z. mobilis* promoter fragment and celY) from pLOI2348 inserted into the AscI site of pLOI2350 | See text |
| pLOI2353 | EcoRI-AvaI fragment (tet gene) from pBR322 inserted into the ClaI site of pFT-A. | See text |
| pLOI2354 | pUC19 derivative in which the multiple cloning sites from HindIII to SmaI were deleted by digestion, Klenow-treatment, and self-ligation | See text |
| pLOI2355 | EcoRI fragment (celZ gene) from pLOI2349 inserted into the EcoRI site of pLOI2354. | See text |
| pLOI2356 | SmaI fragment containing the apramycin resistance gene (aac gene) from pHPΩ45aac inserted into the T4 polymerase-treated PstI site of pLOI2355, disrupting the celZ gene | See text |
| pLOI2357 | EcoRI fragment (aac and disrupted celZ) inserted into the EcoRI site of pLOI2224 | See text |
| pLOI2358 | Subclone of pLOI2323 in which the internal PstI fragment was deleted, used for sequencing | See text |
| pLOI2359 | Subclone of pLOI2323 in which the ClaI-HindIII fragment was deleted, used for sequencing | See text |

*Escherichia coli* DH5α and TOPO10F' were used as hosts during plasmid constructions. The celZ gene, celY gene, and out genes were cloned as described in Example 3.

*E. coli* cultures were grown at 37° C. in Luria-Bertani broth (LB) containing per liter: 10 g Difco® tryptone, 5 g Difco® yeast extract, and 5 g sodium chloride or on solid LB medium containing agar (1.5%). Sugar was always included in broth (5% glucose or sorbitol) and solid media (2% glucose) used for the growth of ethanologenic strains. Clones were screened for endoglucanase production using the Congo Red method (Wood et al. (1988) *Methods Enzymology* 160:87–112). Endoglucanse indicator plates were prepared by supplementing LB agar with 0.3% low viscosity carboxy methyl cellulose (CMC). Ampicillin (50 µg/ml), apramycin (100 µg/ml), kanamycin (50 µg/ml), chloramphenicol (40 µg/ml) and spectinomycin (100 µg/ml) were used for selection. Ethanologenic strains of *K. oxytoca* were maintained at 30° C. on solid LB medium containing glucose (2%) and chloramphenicol (600 µg/ml).

Genetic Methods

Standard methods were used for plasmid construction, analyses, and sequencing. The ribosome-binding site and promoterless coding region of celY were amplified by the polymerase chain reaction using pMH18 as the template with the following primer pairs: N-terminus 5'CTGTTC-CGTTACCAACAC3' (SEQ ID NO:13), C-terminus 5'GTGAATGGGATCACGAGT3' (SEQ ID NO:14). The *E. chrysanthemi* out genes (pCPP2006) were transferred by conjugation using pRK2013 for mobilization. Constructions were confirmed by sequencing using the dideoxy method and a LI-COR Model 4000-l. DNA sequencer with fluorescent primers. The *E. chrysanthemi* celY and celZ genes were introduced into *K. oxytoca* P2 by electroporation using a Bio-Rad Gene Pulser®. Recombinants were selected on solid medium containing kanamycin (50 mg/liter) as described in Martinez-Morales, et al. (1999) *J. Bacteriology* 181:7143–7148, and Zhou, et al. (1999) *Indust. Microbiol. Biotechnol.* 22:600–607.

Primer Extension Analysis

Promoter regions were identified by mapping the transcriptional start sites using a IRD41-labeled primer fluorescent primers within the coding regions: 5'-ACCATCAGCATCAACGCCCAACAACG-3' (SEQ ID NO: 15) for celY and 5'-GACTGGATGGTTATCCGAATAAGAGAGAGG-3' (SEQ ID NO: 16) for celZ. Extension products were dissolved in loading buffer and compared to parallel dideoxy sequences using the LI-COR Model 4000-L DNA sequencer (Lincoln, Nebr.).

Enzyme Assay

Endoglucanase activity was determined as described in Example 3.

Fermentation

Simultaneous saccharification and fermentation (SSF) tests were conducted in unbaffled, 500-ml flasks containing a 200 ml of broth. Flasks were fitted with a rubber stopper and vented with an 18 gauge needle. Fermentations were conducted at 35° C. (120 rpm) in LB medium containing 10% Sigmacell 50 (crystalline cellulose). Inocula were grown for 12 hours in LB containing 5% glucose. Cells were harvested by centrifugation and resuspended in LB. Each flask was inoculated to provide an initial density of 16 mg of cells (dry weight).

Materials and Chemicals

Tryptone and yeast extract were products of Difco (Detroit, Mich.). Antibiotics, low viscosity CMC, and Sigmacell 50® were obtained from the Sigma Chemical Company (St. Louis, Mo.). The IRD41-labeled fluorescent primers were purchased from LI-COR, Inc. (Lincoln, Nebr.).

Construction of a Promoter-probe Vector for celY

The celY gene from *E. chrysanthemi* is poorly expressed from its native promoter in *E. coli* (See Guiseppi, et al. (1991) *Gene* 106:109–114). Accordingly, to increase expression, a promoter-probe vector was constructed as follows using celY as the reporter (See FIG. 13). A promoterless celY coding region with ribosomal-binding site (1.2 kbp) was amplified by PCR using pMH18 as the template and randomly inserted into the topoisomerase vector, PCR2.1-TOPO. Functional expression of celY was confirmed using endoglucanase indicator plates. A clone oriented to express cely from the lac promoter was selected and designated pLOI2311 (5.2 kbp). An EcoRI fragment containing the promoterless celY gene was isolated from pLOI2311. The ends of this fragment were blunted using Klenow polymerase prior to ligation into the HincII site of pUC18. A clone oriented to express celY from the lac promoter was selected (3.9 kbp) and expression confirmed using endoglucanase indicator plates (pLOI2316). The promoterless celY gene was isolated from pLOI2316 as a 1.2 kbp fragment using EcoRI and HindIII and inserted into the corresponding sites of pLOI2302 (pUC19 derivative) to reverse the direction of the celY gene. As expected, the resulting construct DH5α(pLOI2317) was inactive on endoglucanase indicator plates due to the lack of a promoter. To facilitate the insertion of DNA fragments containing promoter regions, plasmid pLOI2317 (3.9 kbp) contains a BamHI site in the polylinker region, immediately upstream from the celY gene (See FIG. 13).

Construction of Plasmids with Increased Expression of celY in *E. coli* DH5α

Sau3A1 fragments of *Z. mobilis* chromosomal DNA were used to provide a heterologous promoter that would not be subject to native regulatory mechanisms in *K. oxytoca* or interfere with subsequent integration into the *K. oxytoca* chromosome (Zhou, et al. (1999) *J. Indust. Microbiol. Biotechnol.* 22:600–607).Fragments of 0.5–1.5 kbp were isolated and randomly ligated into the BamHI site of pLOI2317 to generate a library of surrogate promoters (See FIG. 13). Approximately 75,000 colonies were screened on endoglucanase indicator plates. One-third of the clones actively produced cely. The most active 100 colonies were identified by zone size, purified, and re-tested. The 30 clones with the largest zones of activity were grown overnight in LB and assayed for CMCase activity. The five most active are listed in Table 14 below, and exhibited approximately 7-fold higher activity than the original clone, pMH18. Plasmid pLOI2323 was selected for further investigation.

TABLE 14

Expression of celY in DH5α using fragments using Sau3A1 digestion products of *Z. mobilis* chromosomal DNA as surrogate promoters.

| Plasmids expressing celY or celZ | Endoglucanase activity (IU/L) | | |
|---|---|---|---|
| | Extracellular | Total | % Extracellular |
| pMH18 (native celY promoter) | 151 | 184 | 82 |
| pLOI2317 (promoterless celY vector) | 0 | 0 | 0 |
| celY expressed from surrogate promoters | | | |
| pLOI2318 | 1,123 | 1,257 | 89 |
| pLOI2319 | 888 | 1,023 | 87 |
| pLOI2320 | 1,023 | 1,056 | 97 |

TABLE 14-continued

Expression of celY in DH5α using fragments using Sau3A1 digestion products of Z. mobilis chromosomal DNA as surrogate promoters.

| Plasmids expressing celY or celZ | Endoglucanase activity (IU/L) | | |
|---|---|---|---|
| | Extracellular | Total | % Extracellular |
| pLOI2323 | 1,257 | 1,291 | 97 |
| pLOI2342 | 1,224 | 1,257 | 97 |
| pLOI2349 (celZ) | 3,414 | 16,234 | 21 |

All plasmids are pUC derivatives. Endoglucanase activity was measured using cultures grown at 37° C. for approximately 16 hours.

The Z. mobilis Sau3A1 fragment (937 bp) in pLOI2323 was sequenced in both directions (GenBank Accession No. AF305919). Based on a database comparison, this fragment appears to be derived from two pieces, a 882 bp fragment form Z. mobilis chromosome which corresponds to a previously sequenced region and a 55 bp fragment from the vector. A BLAST search (National Center for Biotechnology Information; http://www.ncbi.nlm.nih.gov/BLAST/) of the translated sequence did not reveal identity to known genes. Four sites of transcriptional initiation were identified in DH5α (pLOI2323) by primer extension analysis involving three different sigma factors, $\delta^{32}$, $\delta^{38}$, and $\delta^{70}$ (See FIG. 14). Although the differences in intensity were less than 2-fold, the sequence upstream from the most intense start site resembled the consensus for $\delta^{32}$ (rpoH), the heat shock promoter (Wang, et al. (1998) *J. Bacteriology* 180:5626–5631; Wise, et al. (1996) *J. Bacteriology* 178:2785–2793).

Construction of a Vector for the Integration of celY and celZ into the Chromosome of K. oxytoca P2

The plasmid pLOI2307 (7.2 kbp) was constructed and used to express celZ from a surrogate Z. mobilis promoter at high levels in recombinant E. coli DH5α (See Zhou, et al. (1999) *B.Appl. Environ. Microbiol.* 65:2439–2445) and K. oxytoca M5A1 (See Zhou, et al. (1999) *Indust. Microbiol. Biotechnol.* 22:600–607). To facilitate subcloning of this hybrid celZ gene and promoter (4.5 kbp), an EcoRI linker was inserted into the T4 polymerase-treated SphI site of pLOI2307 to provide flanking EcoRI sites for convenient excision (pLOI2349). Prior to constructing a plasmid containing celY and celZ, a random 3 kbp fragment of EcoRI-digested K. oxytoca M5A1 chromosomal DNA was inserted into pLOI2323 containing celY (and surrogate promoter) to serve as a guide for homologous recombination (pLOI2348; 8 kbp). This 3 kbp M5A1 fragment was partially sequenced and appears to encode the complete M5A1 glgP gene. In pLOI2348 (8 kbp), flanking AscI sites allowed the excision of a single 5.5 kbp fragment containing the M5A1 glgP gene, Z. mobilis surrogate promoter, and E. chrysanthemi celY.

FIG. 15 summarizes the construction of the celY, celZ integration vector from pLOI2349, pLOI2224, and pLOI2348. The recombinant celY and celZ genes containing surrogate promoters and the guide fragment were sequentially inserted into the core integration vector, pLOI2224 (Martinez-Moralez, et al., supra) using E. coli S17-1 as the host, to produce pLOI2352 (12 kbp). The 4.5 kbp EcoRI fragment from pLOI2349 containing cel/z was inserted into pLOI2224 using an EcoRI site to make pLOI2350 (6.4 kbp).

The 5.5 kbp AscI fragment from pLOI2348 containing celY was inserted into the AscI site of pLOI2350 to make pLOI2352 (12 kbp). The fragments containing cel genes were oriented such that expression from the surrogate promoters was divergent. The resulting vector contained a R6K replicon that does not function in DL5α or M5A1. The two FRT sites in pLOI2352 facilitate removal of the kanamycin gene and replicon after integration (Martinez-Moralez, et al., supra).

Functional Integration of celY and celZ into the K. oxytoca P2 Chromosome

Plasmid pLOI2352 was introduced into P2 by electroporation followed by selection for kanamycin resistance. Approximately 150 colonies were recovered and all were positive on endoglucanase indicator plates. Ten clones with the largest zones of activity were purified, grown in broth and assayed for endoglucanase activity. These produced 5–6 IU/ml of endoglucanase activity. One clone was selected for further study and designated as SZ12.

Due to the natural resistance of K. oxytoca to ampicillin, an additional antibiotic resistance marker (tet) was added to pFT-A plasmid containing the flp recombinase to facilitate selection. The tetracycline gene was isolated as a 1.4 kbp EcoRI to AvaI fragment from pBR322. After treatment with Klenow polymerase, this fragment was ligated into the Klenow-treated ClaI site of pFT-A to produce pLOI2353 (7.0 kbp). This plasmid encodes resistance to both ampicillin and tetracycline, the FLP recombinase (flp) under the control of the tetracycline promoter, and a temperature-conditional pSC101 replicon.

Plasmid pLOI2353 was transformed into SZ12 and plated at 30° C. with selection for tetracyline resistance. The presence of tetracycline also induced flp expression resulting in a deletion of the kanamycin gene and R6K replicon from chromosomally integrated pLOI2353. Of 307 tetracycline-resistant colonies tested, >99% retained expression of the endoglucanase genes and were sensitive to kanamycin. Clones were purified, grown in broth and assayed for endoglucanase activity. All were similar and one was designated SZ21(pLOI2353). The helper plasmid was eliminated from SZ21 by overnight growth at 37° C.

Construction of a celZ Knockout Mutation

Figure 16:
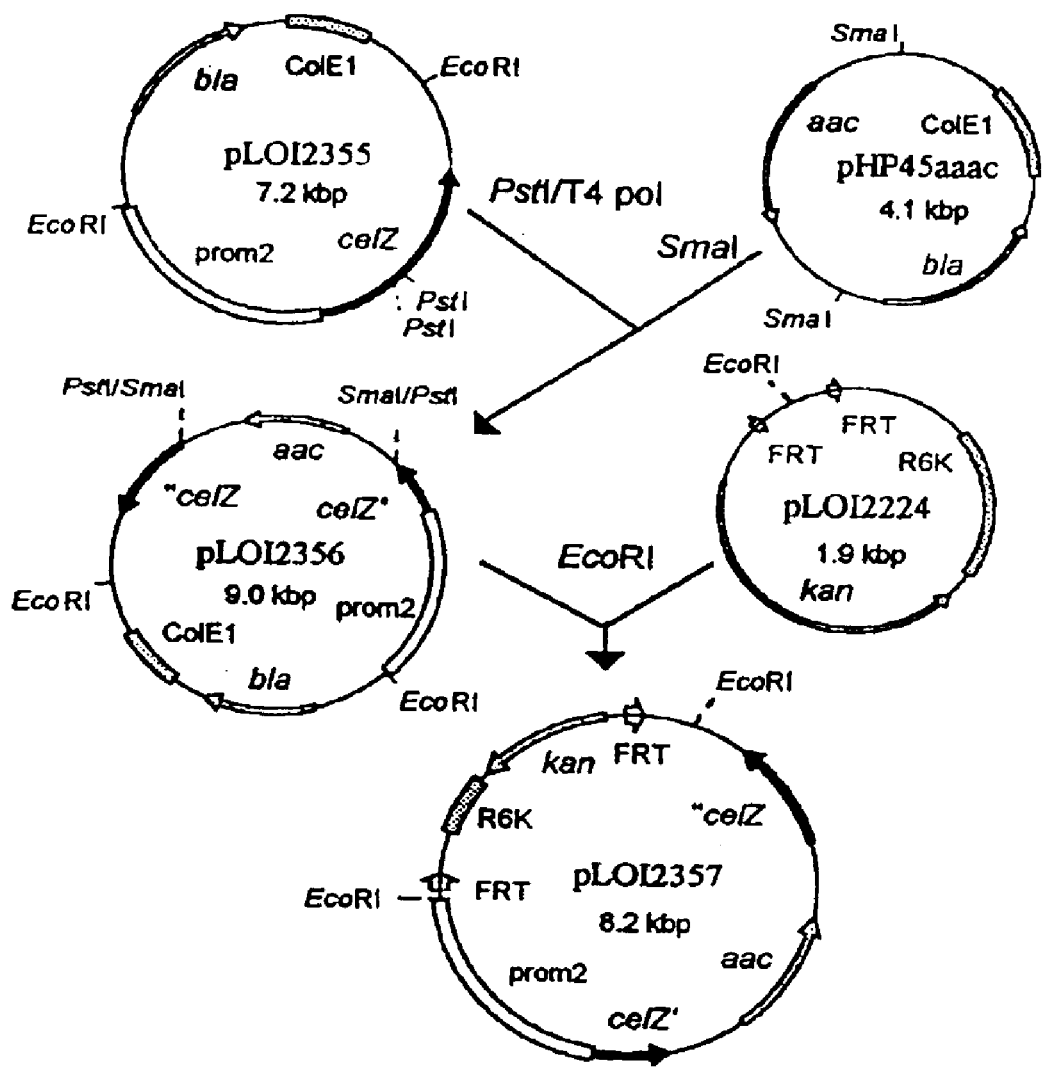
FIG. 16 is a schematic representation of the construction of pLOI2357 for the inactivation of celZ by double homologous recombination. Coding regions for celY are shown as solid segments. The fragment of Z. mobilis DNA that serves as a promoter (prom1) is shown as open segments. Replicons and antibiotic resistance genes are stippled; other vector DNA is shown as a thin connecting line. Arrows on segments indicate the direction of transcription. The small open arrows represent the FRT sites, which are recognized by the flp recombinase.

To confirm the presence of functional celY in SZ21, a knockout mutation of the chromosomally integrated celZ was constructed by double, homologous recombination using plasmid pLOI2357 (FIG. 16). Plasmid, pUC19 was digested with SmaI and HindIII, treated with Klenow polymerase, and self-ligated to eliminate many of the polylinker sites (pLOI2354). The remaining EcoRI site was used to insert a 4.5 kbp EcoRI fragment containing the promoter and celZ gene from pLOI2349 to make pLOI2355 (7.2 kbp). The 1.8 kbp SmaI fragment from pHPΩ45aac containing the apramycin resistance gene (aac) was then ligated into the central region of celZ, replacing a small internal PstI fragment (after blunting with T4 polymerase) to produce pLOI2356 (9.0 kbp). The 6.3 kbp EcoRI fragment from this plasmid was isolated and inserted into the core integration vector, pLOI2224, to produce pLOI2357 (8.2 kbp). This plasmid contains a conditional R6K replicon and kanamycin resistance gene in addition to a celZ gene that is interrupted by an apramycin resistance gene.

Plasmid pLOI2357 was electroporated into SZ21 with selection for apramycin. Approximately 10% of the recombinants were apramycin resistant and kanamycin sensitive indicating a double homologous recombination event. These clones exhibited low levels of endoglucanase production on indicator plates (See Table 15, below). One was selected and designated SZ22. Loss of EGZ and retention of EGY in SZ22 was confirmed by SDS-PAGE using the Pharmacia Phast Gel system.

It is interesting to note that cell clumping in liquid culture, typical of M5A1 and P2, was eliminated by the functional expression of celZ from integrated genes or from plasmids. Clumping was not affected by the functional expression of celY alone.

Transcriptional Initiation in *K. oxytoca* SZ21

Primer extension analysis of celY and celZ in SZ21 were similar to those observed in DH5α. A single major transcriptional start was identified for celZ that corresponded precisely to the most prominent start site in DH5α (pLOI2183) which contains the same promoter fragment (Zhou, et al. (1999) *J. Indust. Microbiol. Biotechnol.* 22:600–607; Zhou, et al. (1999) *B. Appl. Environ. Microbiol.* 65:2439–2445). DNA immediately upstream from this site resembles the recognition sequence for a $\sigma^{70}$ promoter (Wang, et al., supra and Wise, et al., supra). As observed with DH5α (pLOI2323) (See FIG. 14), primer extension analysis of celY indicated the presence of multiple putative transcriptional starts in SZ21. Although localized in the same regions as the start sites in DH5α(pLOI2323), all bands were of near equal intensities.

Effect of the *E. chrysanthemi* Out Genes (pCPP2006) on the Extracellular Secretion of EGY and EGZ in Derivatives of *K. oxytoca* P2

Table 7 summarizes the endoglucanase activities exhibited by cellulolytic derivatives of ethanologenic *K. oxytoca* P2. Strain SZ6 (Zhou, et al., (1999) *J. Indust. Microbiol. Biotechnol.* 22:600–607) contains a chromosomally integrated hybrid celZ gene with same promoter fragment used to construct SZ21. Despite the presence of two endoglucanase genes in SZ21, extracellular and total endoglucanase activities were 13% lower in this strain than in SZ6. Most of the endoglucanase activity produced by SZ21 can attributed to celZ. SZ22, a celZ mutant of SZ21, expressed only 11% of the endoglucanase produced by the parent containing functional celY and celZ genes. In strains SZ6 and SZ21 containing a functional celZ, most of the endoglucanase activity (primarily EGZ) was cell associated. In strain SZ22 containing a functional celY alone, half of the endoglucanase activity was extracellular.

The addition of the out genes (pCPP2006) to recombinant *E. coli* and *K. oxytoca* M5A1 harboring celZ can cause a dramatic increase in the functional expression of celZ and in the fraction of EGZ secreted into the extracellular milieu (Zhou, et al., (1999) *J. Indust. Microbiol. Biotechnol.* 22:600–607; Zhou, et al., (1999) *B. Appl. Environ. Microbiol.* 65:2439–2445). These same effects were observed for ethanologenic *K. oxytoca* SZ21 containing celZ and celY (See Table 14). Addition of the out genes to SZ22 (inactive celZ) had no effect on the functional expression of celY or the extent of EGY secretion. This celZ mutant, SZ22 (pCPP2006), produced only 3% of the total endoglucanase activity (EGY) produced by SZ21 (pCPP2006) containing functional cely and celZ genes. The secreted endoglucanase produced by SZ21 with the out genes was substantially higher than the sum of the individual activities expressed from the same respective promoters in SZ6 (EGZ) and SZ22 (EGY), consistent with synergism between these two enzymes. In this assay, synergy is estimated to be 1.4-fold the arithmetic sum of the individual activities (SZ6 (pCPP2006) and SZ22(pCPP2006)) for the combination of extracellular enzymes produced by SZ21(pCPP2006).

Synergism Between Recombinant *E. chrysanthemi* Endoglucanase (EGZ and EGY) and Fungal Cellulase (Spezyme CE®) during the Fermentation of Cellulose to Ethanol SSF tests in flasks were used without pH control to evaluate the combined effects of fungal cellulase (Spezyme®) and cellulase enzymes produced by the biocatalysts on ethanol production from Sigmacell 50®, a highly crystalline substrate. Results are indicated in Table 16, below.

TABLE 15

Effect of out genes (pCPP2006) on endoglucanase production by derivatives of *K. oxytoca* P2.

| Strains | CMC zone (mm) | $OD_{550}$ | CMCase Activity (IU/L)[a] | | |
|---|---|---|---|---|---|
| | | | Extracellular | Total | Secretion (%) |
| P2 | 0 | 10.5 | 0 | 0 | 0 |
| SZ6 | 8.5 | 11.0 | 1,920 | 8,800 | 22 |
| SZ21 | 6.7 | 11.0 | 1,620 | 7,800 | 21 |
| SZ22 | 2.0 | 10.0 | 480 | 879 | 55 |
| P2 (pCPP2006) | 0 | 10.0 | 0 | 0 | 0 |
| SZ6 (pCPP2006) | 10.8 | 9.6 | 13,800 | 22,300 | 62 |
| SZ21 (pCPP2006) | 11.5 | 10.2 | 20,100 | 26,900 | 75 |
| Spezyme CE ® (10 ml/liter)[b] | — | — | — | 27,000 | — |
| Spezyme CP ® (10 ml/liter)[b] | — | — | — | 33,400 | — |

[a] Endoglucanase activity was measured using cultures grown at 30° C. in LB containing 5% sorbitol for 24 h.
[b] Dilution equivalent to the highest Spezyme ® level used in fermentation experiments (Table 4).

TABLE 16

Maximum ethanol production

| Strain | Type | Genencor Spezyme ® Addition (ml/liter) | N | Fermentation[a] Ethanol ± SD (g/liter)[b] | % Control ± SD |
|---|---|---|---|---|---|
| P2 (pCPP2006) | none | 0 | 3 | 0.23 ± 0.01 | 100 ± 2.0 |
| SZ6(pCPP2006) | none | 0 | 3 | 0.28 ± 0.02* | 124 ± 8.5 |
| SZ21(pCPP2006) | none | 0 | 3 | 0.26 ± 0.02* | 116 ± 8.5 |
| SZ22(pCPP2006) | none | 0 | 3 | 0.24 ± 0.01 | 107 ± 1.0 |
| P2(pCPP2006) | CE | 5.0 | 6 | 13.7 ± 0.3 | 100 ± 2.0 |
| SZ6(pCPP2006) | CE | 5.0 | 6 | 13.8 ± 0.3 | 101 ± 2.4 |
| SZ21(pCPP2006) | CE | 5.0 | 6 | 16.0 ± 0.5** | 117 ± 3.5 |
| SZ22(pCPP2006) | CE | 5.0 | 6 | 15.2 ± 0.3** | 112 ± 1.5 |
| P2(pCPP2006) | CE | 10.0 | 6 | 20.7 ± 0.5 | 100 ± 2.1 |
| SZ6(pCPP2006) | CE | 10.0 | 6 | 21.2 ± 0.1 | 103.4 ± 0.4 |
| SZ21(pCPP2006) | CE | 10.0 | 6 | 24.6 ± 0.5** | 121 ± 2.3 |
| SZ22(pCPP2006) | CE | 10.0 | 6 | 25.2 ± 1.1** | 122 ± 5.0 |
| P2(pCPP2006) | CP | 5.0 | 6 | 15.2 ± 0.3 | 100 ± 1.7 |
| SZ21(pCPP2006) | CP | 5.0 | 6 | 17.8 ± 0.4** | 116 ± 2.2 |
| P2(pCPP2006) | CP | 10.0 | 6 | 25.3 ± 0.7 | 100 ± 2.6 |
| SZ21(pCPP2006) | CP | 10.0 | 6 | 27.2 ± 0.3** | 107 ± 1.2 |

[a] Cultures without added cellulose (100 g/liter) or Spezyme ® produced 0.22 ± 0.01 g/liter of ethanol. Spezyme ® contained approximately 100 FPU/ml. Addition of 5 ml and 10 ml of Spezyme ® corresponds to 5 FPU/g and 10 FPU/g cellulose, respectively.
[b] Student t-test shows that there is significant difference in ethanol production compared to the respective P2 controls at each Spezyme ® dilution. P value ≤0.001 is indicated by a two asterisks. P value ≤0.05 is indicated by a single asterisk.

Although very low levels of ethanol were produced by all strains in the absence of Spezyme®, strains SZ6(pCPP2006) and SZ21(pCPP2006) containing functional celZ genes produced higher levels of ethanol (p<0.05) than strain SZ22 (pCPP2006) containing only a functional celY gene and strain P2(pCPP2006) lacking endoglucanase genes. In the absence of both Spezyme® and Sigmacell 50®, all strains produced 0.22 g/L ethanol. The additional increment of ethanol produced by SZ6(pCPP2006) and SZ21(pCPP2006) during incubation with Sigmacell 50 is attributed to hydrolysis of the small fraction of amorphous cellulose in the substrate by EGZ (Zhou, et al. (1999) *J. of Industrial Microbiol. Biotechnol.* 22:600–607; Zhou, et al. (1999) *B. Appl. Environ. Microbiol.* 65:2439–2445; Zhou, S., et al. (2000) *J. Bacteriol.* 182:5676–5682). Digestion of amorphous cellulose by EGY produces saccharides that are too large to be transported and metabolized without further hydrolysis (Zhou, S., et al. (2000) *J. Bacteriol.* 182:5676–5682).

Spezyme CE® and Spezyme CP® contain a commercially optimized combination of endoglucanase, exoglucanase, and cellobiase activities (Beguin, et al. (1994) *FEMS Microbiol. Rev.* 13:25–58; Boyer, et al. (1987) *Eur. J. Biochem.* 162:311–316; Nieves, et al. (1998) *World Journal of Microbiology and Biotechnology* 14:310–314; Ohmiya, et al. (1997) *Biotechnol. Genetic Eng. Rev.* 14:365–414). Despite this optimization, Spezyme®-supplemented fermentations with two of the endoglucanase producing biocatalysts, SZ21(pCPP2006) and SZ22(pCPP2006), produced significantly higher levels of ethanol than the control P2(pCPP2006) which lacks endoglucanase genes. The combinations of Spezyme® and SZ21(pCPP2006) and SZ22 (pCPP2006) were synergistic in terms of ethanol production, up to 20% higher than the sum of ethanol produced by each individually (p≤0.005). Synergy was observed for both dilutions of Spezyme CE®, and for Spezyme CP®. This synergistic effect can be attributed primarily to EGY since this is the only endoglucanase produced by SZ22 (pCPP2006). No synergy was observed for SZ6(pCPP2006) which produces only EGZ.

EXAMPLE 5

Simultaneous Saccharification and Fermentation of Amorphous Cellulose to Ethanol by Recombinant *Klebsiella oxytoca* SZ21 without Supplemental Cellulase In this example, a derivative of *Klebsiella oxytoca* M5A1 containing chromosomally integrated genes for ethanol production from *Zymomonas mobilis* (pdc, adhB) and endoglucanase genes from *Erwinia chrysanthemi* (cely celZ) is demonstrated to produced over 20,000 U/L of endoglucanase activity during fermentation. In particular, this strain is demonstrated to, in combination with its native ability to metabolize cellobiose and cellotriose, ferment amorphous cellulose to ethanol (58–76% of theoretical yield) without the addition of cellulase enzymes from other organisms.

Throughout this example, the following materials and methods are used unless otherwise stated.
Materials and Methods
Bacteria, Plasmids and Culture Conditions Four ethanologenic derivatives of *Klebsiella oxytoca* M5A1 were used in this study. Strain P2 contains chromosomally integrated pdc and adhB genes from *Z. mobilis* for ethanol production (Wood et al., (1992) *Appl. Environ. Microbiol.* 58: 2103–2110). This strain was the parent organism for three strains that contain highly expressed, chromosomally integrated endoglucanase genes from *E. chrysanthemi* (Zhou et al. (2001) *Appl. Environ. Microbiol.* 67: 6–14). Strains SZ6, SZ22, and SZ21 contain celZ alone, celY alone, and both celY and celZ, respectively. Additional genes (approximately 15 out genes) were required for the efficient secretion of endoglucanase CelZ (He et al. (1991) *Proc. Natl. Acad. Sci. USA* 88:1079–1083; Pugsley et al., (1997) *Gene* 192: 13–19).and were supplied by plasmid pCPP2006. For consistency, this plasmid has been inserted into all strains. Recombinant *K. oxytoca* strains were grown in Luria broth (per liter: 10 g yeast extract, 5 g tryptone, 5 g NaCl) containing a carbohydrate. Spectinomycin (100 mg/L) was included to maintain plasmid pCPP2006. Seed cultures (5% glucose, 12–16 h) and fermentations were incubated at 35° C. (120 rpm) and were vented using a 22 gauge needle.

Assay of Endoglucanase Activity

Total endoglucanase activity (Cel Y and CelZ) was determined for cultures grown for 24 hours in Luria broth containing 5% sorbitol to minimize interference during the determination of reducing sugars (Zhou et al. (2000) *J. Bacteriol.* 182: 5676–5682). Cell suspensions in broth were briefly treated with ultrasound to release bound enzymes. Dilutions were assayed at 35° C. in 50 mM sodium citrate buffer (pH 5.2) using carboxymethyl cellulose as the substrate (2%). Reactions were terminated by heating (10 min, 100° C.). Activity was expressed as μmole per min of reducing sugar (U) using glucose as a standard.

Thin Layer Chromatography (TLC) Analysis of Cellobiosides

Cellobiosides were separated using Whatman LK5 silica gel plates (Cat. No. 4855-620). Plates were developed in solvent (6 parts chloroform, 7 parts acetic acid, and 1 part water), air-dried, and developed a second time in the same solvent. Saccharides were visualized by spraying with 6.5 mM N-(1-naphthyl)ethylenediamine dihydrochloride and heating to 100° C. for 10 min (Zhou et al. supra).

Preparation of Cellobiosides from Microcrystalline Cellulose

Cellulose was converted to cellobiosides based on the method of Pereira et al. (1988). Sigmacell type 50 cellulose (100 g; Cat. No. S-5504) was slowly added to 400 g of 72% $H_2SO_4$ (w/w) and allowed to hydrolyze at 22° C. with stirring for 18 hr. The digested slurry was precipitated by slowly adding to 2.5 L of cold ethanol (100%), centrifuged, and the pellet washed twice with 1 L of cold ethanol. The pellet was dissolved in 100 ml of $H_2O$, adjusted to pH 6, and centrifuged at 5000× g for 20 min to remove insoluble fibers. The supernatant containing cellobiosides was dried and analyzed.

HPLC Analysis of Cellobiosides

Cellobiosides were analyze using a Waters HPLC equipped with a refractive index monitor and digital integrator. Separations were performed at 65° C. using a BioRad HPX-42A column with distilled water as the mobile phase (0.6 ml/min).

Fermentation of Cellobiosides

Initial fermentations used cellobiosides purchased from the Sigma Chemical Company (Cat. No. C-8071). Seed cultures (112.5 μL) were typically combined with 37.5 μL of 4% cellobiosides in a 1.5-ml microcentrifuge tube and incubated for 36 h (35° C. and 120 rpm). Samples (50 μL each; 0 h, 10 h, and 36 h) were heated (100° C., 10 min) to inactivate enzymes and centrifuged (10,000× g, 5 min) to remove cell debris. Supernatants (4 μL) were then spotted on TLC plates for analysis.

Small fermentations (50-ml flasks, 5 ml broth volume) were conducted in a similar fashion with laboratory samples of cellobiosides prepared by sulfuric acid hydrolysis. Cellobiosides (6 g/L total for saccharides less than 7 glucosyl residues) were filter sterilized in Luria broth. Flasks were inoculated with pelleted cells (5,000× g, 10 min) from a seed culture (dry weight of 0.33 g/L) to eliminate ethanol produced from the glucose in seed media. Samples were removed initially, and then at 24-h intervals for the determination of the presence of ethanol by gas chromatography (Beall et al. (1991) *Biotechnol Bioeng.* 38: 296–303).

Preparation of Amorphous Cellulose

Phosphoric acid-swollen cellulose was prepared by a modification of the method described by Wood (1988). Approximately 20 g of Avicel (Cat. No. PH105, Fluka Chemika) was added slowly to 500 ml 85% $H_3PO_4$, stirred at room temperature overnight, poured into 4 L of ice cold water, and allowed to settle without agitation for 30 min. After decanting the upper liquid layer, 4 L of cold water was added and mixed thoroughly, and repeated 5 times with water, once with 1% $NaHCO_3$, and 5 more times with water (final pH 6–7). The cellulose suspension was concentrated by centrifugation (5000× g, 20 min) and used as a substrate for fermentation. This viscous suspension contained a mixture of crystalline and amorphous cellulose.

The fraction of amorphous cellulose present in the phosphoric acid-swollen cellulose was estimated by repeated digestion with CelY and CelZ endoglucanases. A 24-h culture of SZ21(pCPP2006) was sonicated briefly, centrifuged (5,000× g, 10 min), and the supernatant used as a source of endoglucanase (~20 U/ml). Approximately 1 g of the viscous, acid-swollen cellulose was weighed into each of 6 pre-weighed centrifuge tubes. Two served as controls (no enzyme) and were dried to determine initial dry weight and moisture content. Endoglucanase (9 ml) was added to 4 tubes and these were incubated at 35° C. for 12 h. Chloroform (2 drops) was added to each tube to retard microbial growth. After centrifugation (5,000× g, 20 min), this process was repeated with new enzyme preparations for a total of 6 successive treatments over a 72 h period. Tubes were removed at various times, centrifuged, washed once with distilled water to remove soluble products and salts, and dried to a constant weight at 70° C. Amorphous cellulose was calculated as the reduction in dry matter resulting from endoglucanase digestion.

Fermentation of Amorphous Cellulose

Acid swollen cellulose (40 g, unsterilized) was combined with 5 ml of a 10× concentrate of Luria broth and 5 ml of seed culture (cell dry weight of 0.33 mg/L) in a 125-ml flask. Both spectinomycin (100 μg/ml) and chloramphenicol (40 μg/ml) were added to eliminate contamination. The viscous mixture was initially mixed using an applicator stick, then incubated at 35° C. Due to the high initial viscosity, flasks were mixed at 200 rpm during the first 2 h and subsequently, at 120 rpm. Ethanol was measured by gas chromatography (Beall et al. (1991) *Biotechnol. Bioeng.* 38:296–303).

Viscosity

The viscosity of acid-swollen cellulose preparations was estimated at 22° C. by timing the flow through a vertical 10-ml glass pipette. Solutions of glycerol were used as standards. Flow times of 2 sec to 75 sec were observed for fermentation broths, corresponding to viscosities of 1 to 1,300 centipoise, respectively.

Results

Comparison of Endoglucanase Activities Produced by Ethanologenic Derivatives of *K. oxytoca*

Ethanologenic strains containing endoglucanase genes from *E. chrysanthemi* produced substantial levels of activity during glucose fermentation. The highest activity was produced by strain SZ21(pCPP2006) containing both celZ and celY, 29.3±1.6 U/ml of culture. Strain SZ6(pCPP2006) containing celZ alone produced 22.5±1.7 U/ml and strain SZ22(pCPP2006) containing celY(celZ deletion of strain SZ21) produced 1.0±0.1 U/ml. Approximately 60% of the activity was secreted by each strain, the balance being cell associated and readily released by mild sonication. No endoglucanase activity was detected in the parent, strain P2(pCPP2006).

Analysis of Cellobiosides

The presence of cellobiosides was analyzed by thin layer chromatography and by HPLC. Preparations from the Sigma Chemical Company and those prepared in our laboratory were similar. Lane 1 of both thin layer chromatograms (FIG. 17, panels A and B ) shows a representative separation of the Sigma product at the beginning of fermentation. Small amounts of glucose and cellobiose were present with intermediate amounts of cellotriose and cellohexaose, and larger amounts of cellotetraose and cellopentaose. The most intense region, however, remained at the origin. This region contains cellobiosides of greater than 6 residues and other uncharacterized compounds.

HPLC analyses were in agreement with thin layer chromatograms. The Sigma product contained 3% glucose, 3% cellobiose, 13% cellotriose, 25% cellotetraose, 22% cellopentaose, and 9% cellohexaose. Based on peak areas, approximately 25% of the saccharides were longer than 6 residues. Cellobiosides prepared in our laboratory contained 7% glucose, 6% cellobiose, 10% cellotriose, 15% cellotetraose, 12% cellopentaose, 19% cellohexaose, and 30% saccharides longer than 6 glucosyl residues.

Fermentation of Cellobiosides

Figure 17:
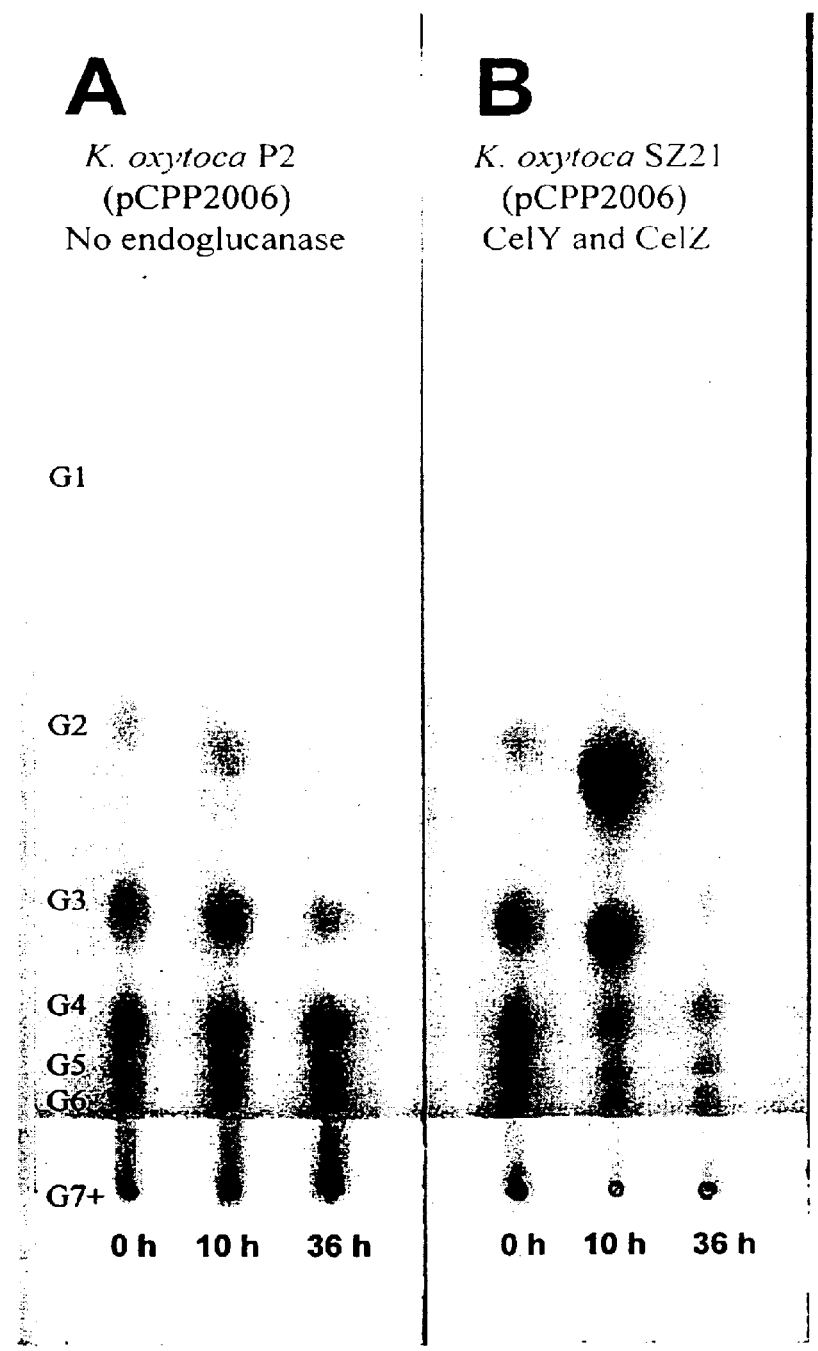
FIG. 17 shows a digital image of a thin layer chromatogram of fermentation broth illustrating the utilization of cellobiosides. The left panel (A) represents strain P2(pCPP2006), the parent lacking E. chrysanthemi endoglucanases, whereas the right panel (B) represents strain SZ21 (pCPP2006), the recombinant secreting high levels of CelY and CelZ endoglucanases. Approximately 4 µL of broth was spotted in each lane and labels G1 through G6 refer to the number of glucosyl residues in the adjacent spots. Lanes for both panels (A and B) are from left to right: 1, initial (0 h); 2, after 10 h; and 3, after 36 h of fermentation.

FIG. 17 shows a thin layer chromatogram comparing the fermentation of cellobiosides (Sigma Chemical Company) by strain P2(pCPP2006) and by SZ21(pCPP2006), a derivative which secretes both endoglucanases CelY and CelZ. Utilization of glucose, cellobiose, and cellotriose by strain P2 was confirmed and is particularly evident after 36 h. However, this strain was unable to metabolize longer cellobiosides. In contrast, strain SZ21 degraded and metabolized virtually all of the separated cellobiosides and a portion of the material at the origin. It is relevant to note that after 10 h, the levels of cellobiose and cellotriose in the SZ21 fermentation were several-fold higher than initially present. This increase was attributed to the hydrolysis of longer cellobiosides by secreted CelY and CelZ.

The effectiveness of secreted endoglucanases was also examined during ethanol production from laboratory cellobiosides (Table 17). Although only low levels of ethanol were produced due to the low substrate concentrations, the benefit of CelZ endoglucanase is clearly evident. The parent P2(pCPP2006) and strain SZ22(pCPP2006; CelY only) produced half as much ethanol as the two strains that secreted CelZ: SZ6(pCPP2006; CelZ only) and SZ21(pCPP2006; CelY and CelZ). Endoglucanase CelY was of no benefit using cellobiosides as substrates, consistent with the requirement for a long-chain substrate.

Ethanol yields were estimated based on cellobiosides containing less than 7 glucosyl residues (Table 17). An average of 62% of the theoretical yield was observed for the two strains producing endoglucanase CelZ. Higher yields (over 90%) were previously measured during the fermentation of 100 g/L cellobiose by strain P2 (Wood & Ingram 1992). It is likely that the lower yields observed with low concentrations of cellobiosides result in part from evaporative losses and the diversion of a larger fraction of carbon to cell growth.

Amorphous Cellulose Content of Phosphoric Acid Swollen Cellulose

Acid swollen cellulose partially recrystallizes during the removal of acid and storage due to extensive hydrogen bonding between cellulose ribbons. E. chrysanthemi Cel Y and Cel Z hydrolyze amorphous cellulose and carboxymethyl cellulose but are unable to hydrolyze crystalline cellulose. This resistance of crystalline cellulose to endoglucanase hydrolysis was used to estimate the fraction of washed, acid-swollen cellulose which remained amorphous as the loss of insoluble material (dry weight). Samples of amorphous cellulose were repeatedly incubated with fresh endoglucanase preparations (~20 U/ml). After an initial 12-h treatment, 28% of the dry weight was solubilized. After four successive treatments, 43% was solubilized and remained constant for the two final treatments. This value, 43%, represents an estimate of the fraction of cellulose that remained in the amorphous state. The actual fraction of amorphous cellulose may be somewhat lower since estimates also include losses of crystalline cellulose which may have occurred during centrifugation and washing.

Fermentation of Amorphous Cellulose

Figure 18:
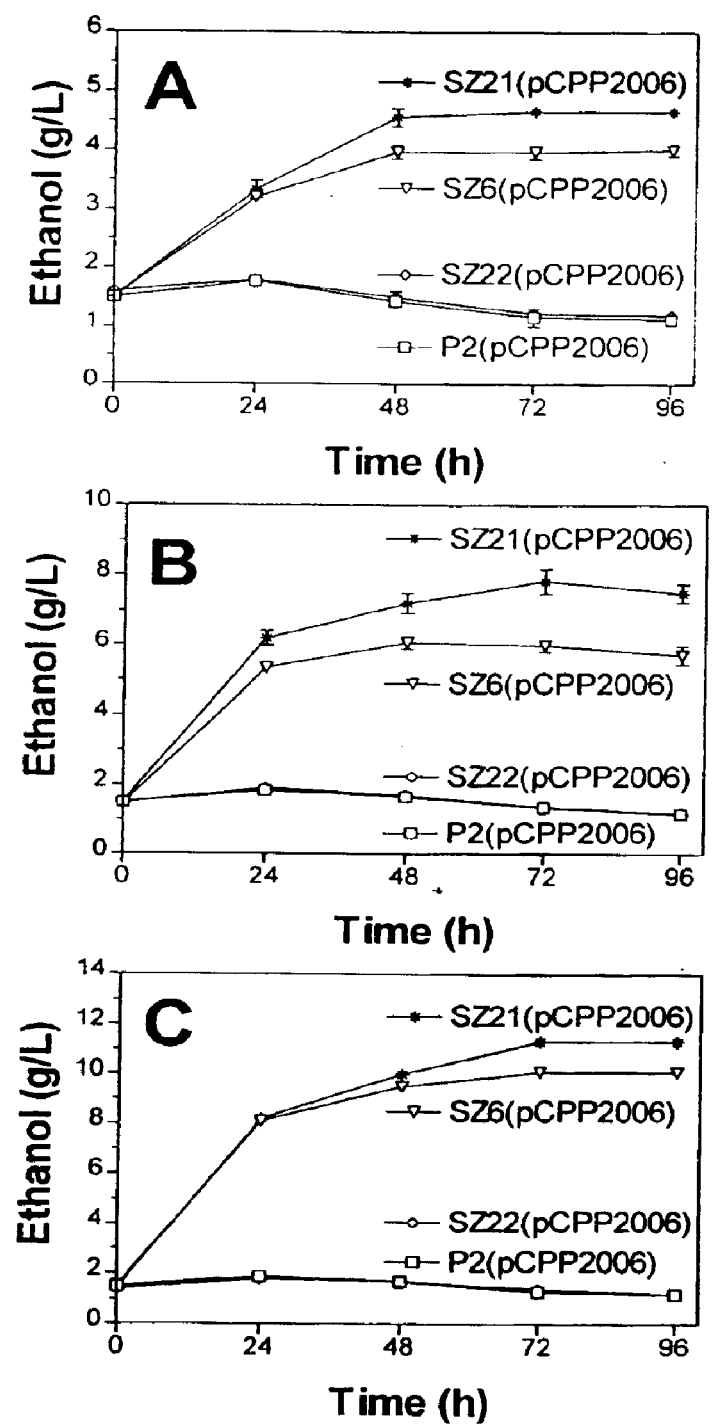
FIG. 18 shows a graphical depiction of the amount of ethanol production from amorphous cellulose by ethanologenic derivatives of K. oxytoca M5A1. Results shown in the top and middle panel (A and B) include standard deviations from three replicates; results shown in the bottom panel (C) represent single fermentations. The top panel (A) shows results from the fermentation of 6.85 g/L amorphous cellulose; the middle panel (B) shows results from the fermentation of 15.33 g/L amorphous cellulose; and the bottom panel (C) shows the fermentation of 28.96 g/L amorphous cellulose. Strain P2(pCPP2006) is the parental strain and lacks *E. chrysanthemi* endoglucanase genes. Strain SZ6 (pCPP2006) secretes CelZ endoglucanase; strain SZ21 (pCPP2006) secretes CelY and CelZ endoglucanases; strain SZ22(pCPP2006) secretes CelY endoglucanase.

The functional expression of high levels of endoglucanase is sufficient to permit the direct conversion of amorphous cellulose to ethanol by two derivatives of K. oxytoca P2 (Table 17; FIG. 18). Three concentrations of amorphous cellulose were tested with similar results.

The highest levels were produced by strain SZ21 (pCPP2006) which secretes a combination of CelY and CelZ endoglucanases. Lower levels of ethanol were produced by strain SZ6(pCPP2006) which secretes CelZ alone. A small amount of ethanol was produced from residual glucose in the seed media by the parent strain, P2(pCPP2006; no endoglucanase) and by strain SZ22(pCPP2006) which secreted only CelY. The combined effects of CelY and CelZ appears to be synergistic for ethanol production and ethanol yield despite the lack of efficacy of CelY alone. Ethanol yields for strain SZ21(pCPP2006; both enzymes) ranged from 58%–76% of the theoretical maximum. This synergistic effect on ethanol production may result from increased hydrolysis due to differences in substrate specificity.

Viscosity Changes During the Fermentation of Amorphous Cellulose

Pronounced viscosity changes were observed during the fermentation of amorphous cellulose by endoglucanase-secreting strains (FIG. 18). The largest reduction in viscosity was evident during the first 2 h of incubation for SZ6 (pCPP2006; CelZ alone) and SZ21(pCPP2006; CelY and CelZ), from a viscosity near that of pure glycerol to that near water. Less pronounced changes were observed with SZ22 (pCPP2006; CelY alone) and no change was evident with the parent strain P2(pCPP2006) which served as a control. Changes in viscosity were essentially complete after 12 h.

Differences in viscosity were quantified at the end of fermentation for Experiment 4 in Table 17 (FIG. 18, panel C). These varied by three orders of magnitude. The highest final viscosity was observed for P2(pCPP2006) which does not produce endoglucanase, 1,300 centipoise. Viscosity was reduced by half (500 centipoise) during fermentation with SZ22(pCPP2006) as a result of hydrolysis by endoglucanase CelY alone. At the end of fermentation, the viscosities of broths from both strains that secrete CelZ were essentially equivalent to that of water, 1 centopoise for SZ21 (pCPP2006; CelY and CelZ) and 2 centipoise for SZ6 (pCPP2006; CelZ alone). Clearly, CelZ alone was more effective than CelY alone. No further benefit was attributed to the production of CelY in combination with CelZ when compared at the end of fermentation (96 h) although both enzymes function synergistically in the production of ethanol (Table 17; FIG. 18) and during saccharification.

In summary, these results using, e.g., K. oxytoca strain SZ21, demonstrate an advancement toward the goal of producing sufficient cellulase enzymes for the direct bioconversion of cellobiosides and amorphous cellulose to ethanol without the addition of supplemental enzymes. Endoglucanase levels produced by this strain are over 10-fold over those previously reported for engineered strains of yeast and other bacteria during ethanol fermentation (Brestic-Goachet et al. 1989, Cho et al. 1999, Cho & Yoo 1999, Misawa et al. 1988, Su et al. 1993, Van Rensburg et al. 1996, 1998). Moreover, the level of endoglucanase produced by strain SZ21 is roughly equivalent to 1% of the endoglucanase activity present in commercial cellulase concentrates (Nieves et al. 1998, Tomme et al. 1995, Wilson et al. 1997).

The effectiveness of strain SZ21 in the hydrolysis of amorphous cellulose results from the combination of two endoglucanase enzymes E. chrysanthemi and function synergistically (Guiseppi et al. 1991, Zhou & Ingram 2000). Moreover, these secreted enzymes function with the phosphotransferase system in K. oxytoca which provides efficient uptake and metabolism of cellobiose and cellotriose (Wood & Ingram 1992, Lai et al. 1997).

TABLE 17

Production of ethanol from cellobiosides and from amorphous cellulose

| Expt. | Strain | Substrate | Substrate (g/L) [a] | N | Ethanol [b] (g/liter) | % Theoretical Yield [c] |
|---|---|---|---|---|---|---|
| 1 | P2 (pCPP2006) | cellobiosides [d] | 6.0 | 2 | 1.06 | 33 |
| 1 | SZ6(pCPP2006) | cellobiosides | 6.0 | 2 | 2.04 | 63 |
| 1 | SZ21(pCPP2006) | cellobiosides | 6.0 | 2 | 2.02 | 62 |
| 1 | SZ22(pCPP2006) | cellobiosides | 6.0 | 2 | 0.93 | 26 |
| 2 | P2(pCPP2006) | amorphous cellulose | 6.85 | 3 | 1.77 ± 0.06 | 0 |
| 2 | SZ6(pCPP2006) | amorphous cellulose | 6.85 | 3 | 3.97 ± 0.12** | 57 |
| 2 | SZ21(pCPP2006) | amorphous cellulose | 6.85 | 3 | 4.67 ± 0.06** | 76 |
| 2 | SZ22(pCPP2006) | amorphous cellulose | 6.85 | 3 | 1.80 ± 0.01 | 0 |
| 3 | P2 (pCPP2006) | amorphous cellulose | 15.34 | 3 | 1.85 ± 0.01 | 0 |
| 3 | SZ6(pCPP2006) | amorphous cellulose | 15.34 | 3 | 6.07 ± 0.18** | 49 |
| 3 | SZ21(pCPP2006) | amorphous cellulose | 15.34 | 3 | 7.84 ± 0.35** | 70 |
| 3 | SZ22(pCPP2006) | amorphous cellulose | 15.34 | 3 | 1.92 ± 0.02 | 0 |
| 4[e] | P2 (pCPP2006) | amorphous cellulose | 28.96 | 1 | 1.90 | 0 |
| 4 | SZ6(pCPP2006) | amorphous cellulose | 28.96 | 1 | 10.1** | 51 |
| 4 | SZ21(pCPP2006) | amorphous cellulose | 28.96 | 1 | 11.3** | 58 |
| 4 | SZ22(pCPP2006) | amorphous cellulose | 28.96 | 1 | 1.80 | 0 |

[a] Inocula for cellobioside fermentations were harvested by centrifugation to eliminate seed broth as a source of ethanol. An average of 1.85 g/L ethanol was produced from residual sugar in the seed broth used to inoculate the three fermentations of amorphous cellulose.
[b] **Indicates that the value is significantly different from that of the control strain (P2) lacking genes encoding E. chrysanthemi endoglucanases (p<0.001).
[c] Yields are calculated as a percentage of theoretical maxima, assumed to be 0.54 g ethanol per gram of cellobiose and 0.56 g ethanol per gram of amorphous cellulose. For amorphous cellulose, yields were computed after subtracting ethanol produced from sugar in the inocula.
[d] Cellobiosides (g/L) represents the sum of glucose plus cellobiosides containing fewer than 7 glucosyl residues.
[e] The highest coefficient of variation in Experiments No. 2 and No. 3 was 4.5% of the mean value. By assuming a similar coefficient of variation (5% of the measured value), significance was also estimated for Experiment No. 3.

Equivalents

Those skilled in the art will recognize, or be able to ascertain using no more than routine experimentation, many equivalents to the specific embodiments of the invention described herein. Such equivalents are intended to be encompassed by the following claims. Moreover, any number of genetic constructs, host cells, and methods described in U.S. Pat. Nos. 5,821,093; 5,482,846; 5,424,202; 5,028,539; 5,000,000; 5,487,989, 5,554,520, and 5,162,516, may be employed in carrying out the present invention and are hereby incorporated by reference.

---

What is claimed:

1. A recombinant host cell suitable for degrading an oligosaccharide comprising:
a first heterologous polynucleotide segment encoding a first endoglucanase having a first degrading activity, wherein said segment is under the transcriptional control of a surrogate promoter; and
a second heterologous polynucleotide segment encoding a second endoglucanase having a second degrading activity, wherein said segment is under the transcriptional control of a surrogate promoter, and
a polynuclcotide segment expressing an additional enzyme,
wherein said first endoglucanase and said second endoglucanase are expressed so that said first and said second degrading activities are present in a ratio such that the degrading of said oligosaccharide by said first and second endoglucanases is synergized and wherein said first endoglucanase is encoded by celZ and said sccond endoglucanase is encodcd by celY, and wherein celZ and celY comprise a polynuelcotide segment isolated from *Erwinia*.

2. The recombinant host cell of claim 1, wherein said first endoglucanase or said second endoglucanase, or both said first and said second endoglucanases are secreted.

3. The recombinant host cell of claim 1, wherein said host cell is a bacterial cell.

4. The recombinant host cell of claim 3, wherein said host cell is selected from the family Enterobacteriaceae.

5. The recombinant host cell of claim 4, wherein said host is *Escherichia* or *Klebsiella*.

6. The recombinant host cell of claim 5, wherein said host cell is selected from the group consisting of *E. coli* B, *E. coli* DH5α, and *Klebsiella oxytoca*.

7. The recombinant host cell of claim 1, wherein said additional enzyme is selected from the group consisting of glucanase, endoglucanase, exoglucanase, cellobiohydrolase, β-glucosidase, endo-1,4-β-xylanase, α-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase, or a combination thereof.

8. The recombinant host cell of claim 1, wherein said additional enzyme is an ethanologenic enzyme.

9. The recombinant host cell of claim 1, wherein said additional enzyme is an ethanologenic enzyme selected from the group consisting of pyruvate decarboxylase and alcohol dehydrogenase.

10. The recombinant host cell of claim 1, wherein said first endoglucanase is EGZ and said second endoglucanase is EGY.

11. The recombinant host cell of claim 1, wherein said additional enzyme is a secretory enzyme.

12. The recombinant host cell of claim 11, wherein said secretory enzyme is a pul or out gene product.

13. The recombinant host cell of claim 1, wherein said host cell is ethanologenic.

14. The recombinant host cell of claim 1, wherein said host cell is selected from the group comprising *E. coli* KO4 (ATCC 55123), *E. coli* KO11 (ATCC 55124), *E. coli* KO12 (ATCC 55125) and *E. coli* LY01 (ATCC 11303), and *K. oxytoca* P2 (ATCC 55307).

15. The recombinant host cell of claim 1, wherein said first and second endoglucanases comprise a polypeptide purified from *Erwinia*.

16. The recombinant host cell of claim 1, wherein said celZ and celY comprise a polynucleotide segment prepared by a process slected from the group consisting of direct cloning of a polynucleotide sequence isolated from *Erwinia*, PCR amplification of a polynucleotide sequence isolated from *Erwinia* and artificial synthesis using as template a polynucleotide sequence isolated from *Erwinia*.

* * * * *

UNITED STATES PATENT AND TRADEMARK OFFICE
CERTIFICATE OF CORRECTION

| | |
|---|---|
| PATENT NO. | : 7,026,152 B2 |
| APPLICATION NO. | : 09/885297 |
| DATED | : April 11, 2006 |
| INVENTOR(S) | : Lonnie O. Ingram et al. |

It is certified that error appears in the above-identified patent and that said Letters Patent is hereby corrected as shown below:

At Column 1, Line 25, after the period following the word "Florida" please add the following sentence:

--The Government has certain rights in the invention.--

Signed and Sealed this

Third Day of April, 2007

JON W. DUDAS
*Director of the United States Patent and Trademark Office*